United States Patent
Blagg et al.

(10) Patent No.: US 12,269,798 B2
(45) Date of Patent: **\*Apr. 8, 2025**

(54) SECOND GENERATION GRP94-SELECTIVE INHIBITORS

(71) Applicant: University of Kansas, Lawrence, KS (US)

(72) Inventors: Brian S. J. Blagg, Niles, MI (US); Vincent Matthew Crowley, Lawrence, KS (US)

(73) Assignee: University of Kansas, Lawrence, KS (US)

( * ) Notice: Subject to any disclaimer, the term of this patent is extended or adjusted under 35 U.S.C. 154(b) by 820 days.

This patent is subject to a terminal disclaimer.

(21) Appl. No.: 17/341,047

(22) Filed: Jun. 7, 2021

(65) Prior Publication Data

US 2021/0300872 A1    Sep. 30, 2021

Related U.S. Application Data

(63) Continuation of application No. 16/640,897, filed as application No. PCT/US2018/047820 on Aug. 23, 2018, now Pat. No. 11,028,041.

(60) Provisional application No. 62/550,292, filed on Aug. 25, 2017.

(51) Int. Cl.
| | |
|---|---|
| C07C 69/94 | (2006.01) |
| A61K 31/216 | (2006.01) |
| A61K 31/44 | (2006.01) |
| A61P 27/02 | (2006.01) |
| A61P 35/04 | (2006.01) |
| C07C 69/76 | (2006.01) |
| C07C 69/78 | (2006.01) |
| C07C 69/88 | (2006.01) |
| C07C 219/34 | (2006.01) |
| C07C 229/52 | (2006.01) |
| C07D 213/55 | (2006.01) |
| C07D 213/643 | (2006.01) |

(52) U.S. Cl.
CPC ............ *C07C 69/94* (2013.01); *A61K 31/216* (2013.01); *A61K 31/44* (2013.01); *A61P 27/02* (2018.01); *A61P 35/04* (2018.01); *C07C 69/76* (2013.01); *C07C 69/78* (2013.01); *C07C 219/34* (2013.01); *C07C 229/52* (2013.01); *C07D 213/55* (2013.01); *C07D 213/643* (2013.01)

(58) Field of Classification Search
None
See application file for complete search history.

(56) References Cited

U.S. PATENT DOCUMENTS

| | | | |
|---|---|---|---|
| 11,028,041 B2 * | 6/2021 | Blagg | ........... C07C 69/76 |
| 2010/0099865 A1 | 4/2010 | Blagg | |
| 2016/0272579 A1 | 9/2016 | Mazitschek et al. | |

OTHER PUBLICATIONS

Fritsch et al., "Synthesis and Gas Permeation Properties of Spirobischromane-Based Polymers of Intrinsic Microporosity," Macromolecular Chemistry and Physics, vol. 212, 2011, pp. 1137-1146, 2011 Wiley-VCH Verlag Gmbh & Co. KGaA, Weinheim . . . .
Crowley, Chemistry: A European Journal, 2017, 23, 15775-15782, p. 15776, figure 2.
Huard, ACS Chemical Biology, 2018, 13, 933-941, p. 936, table 1, compound 4.
International Preliminary Report on Patentability in International Patent Application No. PCT/US2018/047820 dated Apr. 1, 2020 (4 pages).
International Search Report and Written Opinion in International Patent Application No. PCT/US2018/047820 dated Nov. 26, 2018 (12 pages).
Notice of Allowance in U.S. Appl. No. 16/640,897 dated Mar. 3, 2021.
Office Action issued in CA Application No. 3,111,142, mailed Sep. 19, 2024, 3 pages.

\* cited by examiner

*Primary Examiner* — Noble E Jarrell
(74) *Attorney, Agent, or Firm* — Foley & Lardner LLP

(57) ABSTRACT

The present technology provides compounds selective for the Grp94 isoform, as well as compositions including such compounds, that are useful for treatment of multiple myeloma, melanoma, lung cancer, hepatocellular carcinoma, breast cancer, prostate cancer, and/or glaucoma. Methods using the compound are also provided.

24 Claims, 6 Drawing Sheets

SECOND GENERATION GRP94-SELECTIVE INHIBITORS

CROSS-REFERENCE TO RELATED APPLICATIONS

This application is a continuation of U.S. patent application Ser. No. 16/640,897, filed on Feb. 21, 2020, which is a U.S. National Phase Application under 35 U.S.C. § 371 of International Application No. PCT/US2018/047820, filed on Aug. 23, 2018, which claims the benefit of priority to U.S. Provisional Patent Application No. 62/550,292, filed on Aug. 25, 2017, the entire disclosure of each of which is herein incorporated by reference for any and all purposes.

U.S. GOVERNMENT RIGHTS

This invention was made with government support under EY024232 and CA212467 awarded by the National Institutes of Health. The government has certain rights in the invention.

SUMMARY

In an aspect, a compound of Formula I is provided

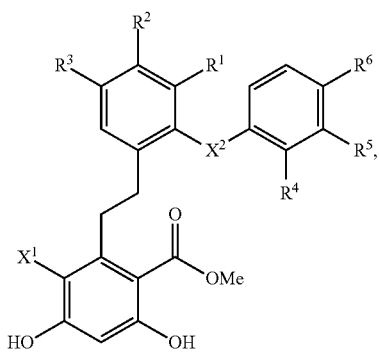

(I)

or a pharmaceutically acceptable salt thereof, wherein
$X^1$ is Cl or F;
$X^2$ is $CH_2$, O, S, or NH;
$R^1$, $R^2$, $R^4$, $R^5$, and $R^6$ are each independently H, alkoxy, hydroxyl, thiol, or halo, and
$R^3$ is H, alkoxy, amino, hydroxyl, thiol, or halo.
In an aspect, provided is a compound of Formula III

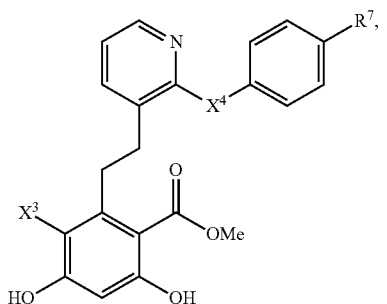

(III)

or a pharmaceutically acceptable salt thereof, wherein
$X^3$ is Cl or F;
$X^4$ is $CH_2$, O, S, or NH; and
$R^7$ is alkoxy, hydroxyl, thiol, or halo.

In another aspect, the present technology also provides compositions (e.g., pharmaceutical compositions) any of one of the embodiments of the compounds disclosed herein (or a pharmaceutically acceptable salt of any thereof) disclosed herein and a pharmaceutically acceptable carrier. The pharmaceutical composition may be for treating metastatic cancer and may include a pharmaceutically acceptable excipient. The pharmaceutical composition may be for treating glaucoma and may include a pharmaceutically acceptable excipient.

In a related aspect, a method for inhibiting cell motility of a cancer cell is provided, the method comprising contacting the cancer cell with a compound of any embodiment disclosed herein.

In a related aspect, a method of treating a patient or animal suffering from metastatic cancer is provided, the method comprising administration of an effective amount of a compound of any embodiment disclosed herein to the patient or animal suffering from the metastatic cancer.

In a related aspect, a method of inhibiting death of a cell exhibiting mutant myocilin is provided, the method comprising contacting the cell with a compound of any embodiment disclosed herein.

In a related aspect, a method of treating a patient or animal suffering from glaucoma is provided, the method comprising administration of an effective amount of a compound of any embodiment disclosed herein.

DETAILED DESCRIPTION

Figure 1:
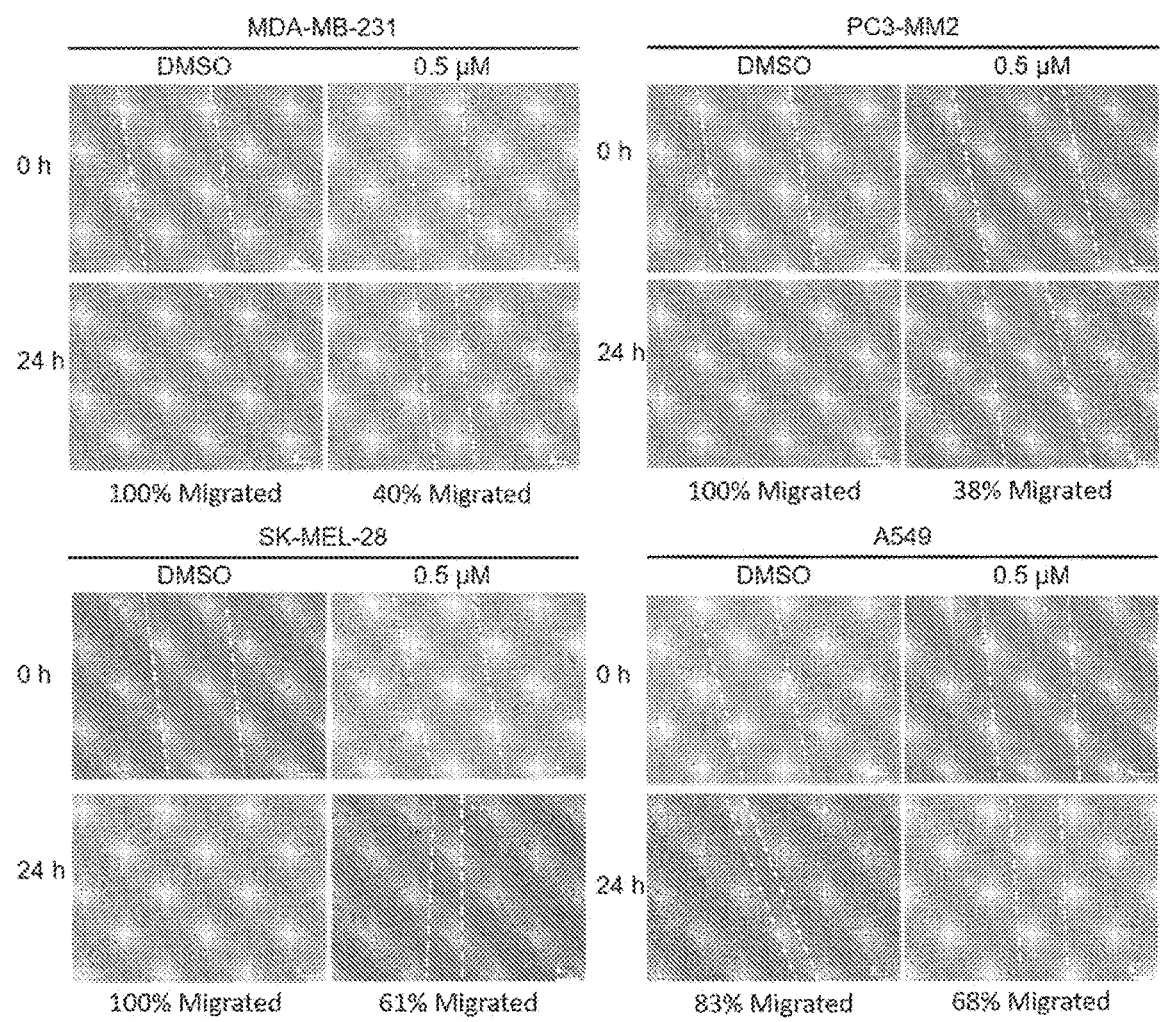
FIG. 1: Representative images of a wound healing scratch assay in different cancer cell lines after 24 h treatment with methyl 3-chloro-2-(2-(4-fluorobenzyl)phenethyl)-4,6-dihydroxybenzoate ("compound 30") of the present technology or vehicle (0.25% final concentration of DMSO), according to the working examples. Scale bar=100 μm.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes, hydroxylamines, alkoxyamines; aralkoxyamines; thiols; sulfides; sulfoxides; sulfones; sulfonyls; pentafluorosulfanyl (i.e., $SF_5$), sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

As used herein, $C_m$-$C_n$, such as $C_1$-$C_{12}$, $C_1$-$C_8$, or $C_1$-$C_6$ when used before a group refers to that group containing m to n carbon atoms.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Alkyl groups may be substituted or unsubstituted. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Cycloalkyl groups may be substituted or unsubstituted. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1] hexane, adamantyl, decalinyl, and the like. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. Cycloalkylalkyl groups may be substituted or unsubstituted. In some embodiments, cycloalkylalkyl groups have from 4 to 16 carbon atoms, 4 to 12 carbon atoms, and typically 4 to 10 carbon atoms. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Alkenyl groups may be substituted or unsubstituted. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, among others. Representative substituted alkenyl groups may be mono-substituted or substituted more than once, such as, but not limited to, mono-, di- or tri-substituted with substituents such as those listed above.

Cycloalkenyl groups include cycloalkyl groups as defined above, having at least one double bond between two carbon atoms. Cycloalkenyl groups may be substituted or unsubstituted. In some embodiments the cycloalkenyl group may have one, two or three double bonds but does not include aromatic compounds. Cycloalkenyl groups have from 4 to 14 carbon atoms, or, in some embodiments, 5 to 14 carbon atoms, 5 to 10 carbon atoms, or even 5, 6, 7, or 8 carbon atoms. Examples of cycloalkenyl groups include cyclohexenyl, cyclopentenyl, cyclohexadienyl, cyclobutadienyl, and cyclopentadienyl.

Cycloalkenylalkyl groups are alkyl groups as defined above in which a hydrogen or carbon bond of the alkyl group is replaced with a bond to a cycloalkenyl group as defined above. Cycloalkenylalkyl groups may be substituted or unsubstituted. Substituted cycloalkenylalkyl groups may be substituted at the alkyl, the cycloalkenyl or both the alkyl and cycloalkenyl portions of the group. Representative substituted cycloalkenylalkyl groups may be substituted one or more times with substituents such as those listed above.

Alkynyl groups include straight and branched chain alkyl groups as defined above, except that at least one triple bond exists between two carbon atoms. Alkynyl groups may be substituted or unsubstituted. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds Examples include, but are not limited to —C≡CH, —C≡CCH$_3$, —CH$_2$C≡CCH$_3$, —C≡CCH$_2$CH(CH$_2$CH$_3$)$_2$, among others. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups herein include monocyclic, bicyclic and tricyclic ring systems. Aryl groups may be substituted or unsubstituted. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. The phrase "aryl groups" includes groups containing fused rings, such as fused aromatic-aliphatic ring systems (e.g., indanyl, tetrahydronaphthyl, and the like). Representative substituted aryl groups may be mono-substituted (e.g., tolyl) or substituted more than once. For example, mono-substituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. Aralkyl groups may be substituted or unsubstituted in some embodiments, aralkyl groups contain 7 to 16 carbon atoms, 7 to 14 carbon atoms, or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indenyl-ethyl. Representative substituted aralkyl groups may be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. Heterocyclyl groups may be substituted or unsubstituted. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. The phrase includes heterocyclyl groups that have other groups, such as alkyl, oxo or halo groups, bonded to one of the ring members, referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups may be substituted or unsubstituted. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Heterocyclylalkyl groups may be substituted or unsubstituted. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, furan-2-yl-methyl, imidazol-4-yl-methyl, pyridin-3-yl-methyl, tetrahydrofuran-2-yl-ethyl, and indol-2-yl-propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Heteroaralkyl groups may be substituted or unsubstituted. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the present technology are not referred to using the "ene" designation. Thus, e.g., chloroethyl is not referred to herein as chloroethylene.

Alkoxy groups are hydroxyl groups (—OH) in which the bond to the hydrogen atom is replaced by a bond to a carbon atom of a substituted or unsubstituted alkyl group as defined above. Alkoxy groups may be substituted or unsubstituted. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "alkanoyl" and "alkanoyloxy" as used herein can refer, respectively, to C(O)-alkyl groups and —O—C(O)-alkyl groups, each containing 2-5 carbon atoms. Similarly, "aryloyl" and "aryloyloxy" refer to —C(O)-aryl groups and —O—C(O)-aryl groups.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "carboxylate" as used herein refers to a —COOH group.

The term "ester" as used herein refers to —COOR$^{70}$ and —C(O)O-G groups. R$^{70}$ is a substituted or unsubstituted alkyl, cycloalkyl, alkenyl, alkynyl, aryl, aralkyl, heterocyclylalkyl or heterocyclyl group as defined herein. G is a carboxylate protecting group. Carboxylate protecting groups are well known to one of ordinary skill in the art. An extensive list of protecting groups for the carboxylate group functionality may be found in Protective Groups in Organic Synthesis, Greene, T. W.; Wuts, P. G. M., John Wiley & Sons, New York, N.Y., (3rd Edition, 1999) which can be added or removed using the procedures set forth therein and which is hereby incorporated by reference in its entirety and for any and all purposes as if fully set forth herein.

The term "amide" (or "amido") includes C- and N-amide groups, i.e., —C(O)NR$^{71}$R$^{72}$, and —NR$^{71}$C(O)R$^{72}$ groups, respectively. R$^{71}$ and R$^{72}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) and formamide groups (—NHC(O)H). In some embodiments, the amide is —NR$^{71}$C(O)—(C$_{1-5}$ alkyl) and the group is termed "carbonylamino," and in others the amide is —NHC(O)-alkyl and the group is termed "alkanoylamino."

The term "nitrile" or "cyano" as used herein refers to the —CN group.

Urethane groups include N- and O-urethane groups, i.e., —NR$^{73}$C(O)OR$^{74}$ and —OC(O)NR$^{73}$R$^{74}$ groups, respectively. R$^{73}$ and R$^{74}$ are independently a substituted or unsubstituted alkyl, alkenyl, alkynyl, cycloalkyl, aryl, aralkyl, heterocyclylalkyl, or heterocyclyl group as defined herein. R$^{73}$ may also be H.

The term "amine" (or "amino") as used herein refers to —NR$^{75}$R$^{76}$ groups, wherein R$^{75}$ and R$^{76}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is NH$_2$, methylamino, dimethylamino, ethylamino, diethylamino, propylamino, isopropylamino, phenylamino, or benzylamino.

The term "sulfonamido" includes S- and N-sulfonamide groups, i.e., —SO$_2$NR$^{78}$R$^{79}$ and —NR$^{78}$SO$_2$R$^{79}$ groups, respectively. R$^{78}$ and R$^{79}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups (—SO$_2$NH$_2$). In some embodiments herein, the sulfonamido is —NHSO$_2$-alkyl and is referred to as the "alkylsulfonylamino" group.

The term "thiol" refers to —SH groups, while "sulfides" include —SR$^{80}$ groups, "sulfoxides" include —S(O)R$^{81}$ groups, "sulfones" include —SO$_2$R$^{82}$ groups, and "sulfonyls" include —SO$_2$OR$^{83}$. R$^{80}$, R$^{81}$, R$^{82}$, and R$^{83}$ are each independently a substituted or unsubstituted alkyl, cycloalkyl, alkenyl, alkynyl, aryl aralkyl, heterocyclyl or heterocyclylalkyl group as defined herein. In some embodiments the sulfide is an alkylthio group, —S-alkyl.

The term "urea" refers to —NR$^{84}$—C(O)—NR$^{85}$R$^{86}$ groups. R$^{84}$, R$^{85}$, and R$^{86}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to —C(NR$^{87}$)NR$^{88}$R$^{89}$ and —NR$^{87}$C(NR$^{88}$)R$^{89}$, wherein R$^{87}$, R$^{88}$, and R$^{89}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to —NR$^{90}$C(NR$^{91}$)NR$^{92}$R$^{93}$, wherein R$^{90}$, R$^{91}$, R$^{92}$ and R$^{93}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to —C(R$^{94}$)=C(R$^{94}$)NR$^{96}$R$^{97}$ and —NR$^{94}$C(R$^{95}$)=C(R$^{96}$)R$^{97}$, wherein R$^{94}$, R$^{95}$, R$^{96}$ and R$^{97}$ are each independently hydrogen, a substituted or unsubstituted alkyl, cycloalkyl, alkenyl, alkynyl, aryl aralkyl, heterocyclyl or heterocyclylalkyl group as defined herein.

The term "halogen" or "halo" as used herein refers to bromine, chlorine, fluorine, or iodine. In some embodiments, the halogen is fluorine. In other embodiments, the halogen is chlorine or bromine.

The term "hydroxyl" as used herein can refer to —OH or its ionized form, —O$^-$. A "hydroxyalkyl" group is a hydroxyl-substituted alkyl group, such as HO—CH$_2$—.

The term "imide" refers to —C(O)NR$^{98}$C(O)R$^{99}$, wherein R$^{98}$ and R$^{99}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to —CR$^{100}$(NR$^{101}$) and —N(CR$^{100}$R$^{101}$) groups, wherein R$^{100}$ and R$^{101}$ are each independently hydrogen or a substituted or unsubstituted alkyl, cycloalkyl, alkenyl, alkynyl, aryl aralkyl, heterocyclyl or heterocyclylalkyl group as defined herein, with the proviso that R$^{100}$ and R$^{101}$ are not both simultaneously hydrogen.

The term "nitro" as used herein refers to an —NO$_2$ group.

The term "trifluoromethyl" as used herein refers to —CF$_3$.

The term "trifluoromethoxy" as used herein refers to —OCF$_3$.

The term "azido" refers to —N$_3$.

The term "trialkyl ammonium" refers to a —N(alkyl)$_3$ group. A trialkylammonium group is positively charged and thus typically has an associated anion, such as halogen anion.

The term "isocyano" refers to —NC.

The term "isothiocyano" refers to —NCS.

The term "pentafluorosulfanyl" refers to —SF$_5$.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g. alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g. Na$^+$, Li$^+$, K$^+$, Ca$^{2+}$, Mg$^{2+}$, Zn$^{2+}$), ammonia or organic amines (e.g. dicyclohexylamine, trimethylamine, triethylamine, pyridine, picoline, ethanolamine, diethanolamine, triethanolamine) or basic amino acids (e.g. arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

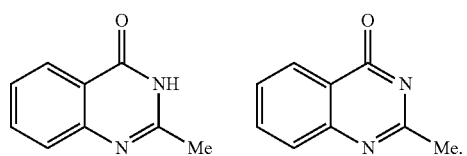

As another example, guanidines may exhibit the following isomeric forms in protic organic solution, also referred to as tautomers of each other:

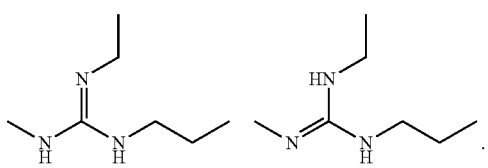

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

Throughout this disclosure, various publications, patents and published patent specifications are referenced by an identifying citation. Also within this disclosure are Arabic numerals referring to referenced citations, the full bibliographic details of which are provided in sections within the Examples. The disclosures of these publications, patents and published patent specifications are hereby incorporated by reference into the present disclosure to more fully describe the present technology.

The Present Technology

Mutations in myocilin are causative for ~3-10% (~3 million patients) of the early onset, heritable form of open-angle glaucoma, a leading cause of blindness worldwide.[30], [31], [32] Myocilin is a protein secreted to the trabecular meshwork (TM),[33], [34], [35], [36], [37] an extracellular matrix (ECM) located in the anterior eye segment. Though the specific function of myocilin in the ECM is not known,[32] the overall role of TM tissue is to regulate the outflow of nutrient-rich aqueous humor fluid.[33] Dysregulation of fluid outflow leads to ocular hypertension, currently the only known and clinically addressable risk factor for glaucoma.[38], [39] Myocilin pathogenicity arises from coding mutations localized within the ~30 kDa myocilin C-terminal olfactomedin (OLF) domain.[40] OLF-directed mutations compromise protein stability,[41], [42], [43] resulting in its aggregation and accumulation in the endoplasmic reticulum (ER) of TM cells,[44], [45], which induces ER stress[46], [47], [48], [50], [51], [52] and ultimately causes cell death.[44], [48] Loss of TM cells is proposed to lead to loss of homeostatic control of intraocular pressure,[53] and it initiates an accelerated path to vision loss and glaucoma. The ER-associated degradation (ERAD) cellular system should efficiently respond to the insult of protein misfolding and aggregation.[54] In the case of mutant myocilin, however, glucose regulated protein 94 (Grp94),[55], [56] the ER-resident heat shock protein 90 (Hsp90) molecular chaperone paralog, fails in its attempt to triage mutant myocilin for ERAD.[47] Grp94 and mutant myocilin co-aggregate and are retained in the ER[47], [57]. Cellular observations are recapitulated in vitro using an aggregation assay with purified proteins: Grp94 accelerates the rate at which the myocilin OLF domain forms thioflavin-T (ThT) positive amyloid aggregates, and Grp94 is recruited into the end-point aggregated material.[57] In cells, knockdown of Grp94 with siRNA or inhibition of Grp94 by pharmacologic intervention results in degradation of toxic mutant myocilin via autophagy, thus rescuing Grp94 from its co-aggregation fate.[47], [57]

The Hsp90 family is responsible for the maturation of nascent polypeptides and the rematuration of denatured proteins. Hsp90 has gained considerable interest as a therapeutic target because Hsp90-dependent proteins are directly associated with all ten hallmarks of cancer.[1] Therefore, inhibition of Hsp90 results in simultaneous disruption of multiple oncogenic pathways that are essential to cancer progression via a single molecular target. 17 small molecule Hsp90 inhibitors have progressed into clinical trials for the treatment of various forms of cancer.[2] Unfortunately, these inhibitors have produced various toxicities that have dampened enthusiasm for Hsp90 as a therapeutic target.[3] Present clinical candidates are pan-Hsp90 inhibitors that target all four Hsp90 isoforms with similar affinity which has been suggested to be the cause of some on-target toxicities.[4] Alternative approaches toward Hsp90 inhibition are needed to overcome these potential liabilities associated with pan-Hsp90 inhibition.

The Hsp90 protein family is composed of four isoforms: Hsp90α and Hsp90β reside in the cytosol, Trap1 is localized to the mitochondria, and Grp94 is found in the endoplasmic reticulum (as discussed above). Grp94 is responsible for the maturation and trafficking of proteins associated with cell signaling and motility.[6] Some Grp94-dependent proteins have been elucidated and include the Toll-like receptors, integrins, insulin-like growth factors I and II, LRP6, and mutant myocilin.[6-7] While Grp94 is essential during embryonic development, it is non-essential in developed organisms.[8] Therefore, Grp94 inhibition represents a non-toxic approach toward the treatment of some diseases (e.g., glaucoma). However, some disease states rely more heavily upon a functional ER chaperone system, such as multiple myeloma and hepatocellular carcinoma, where Grp94 knockouts decrease the viability of these cancers, highlighting Grp94 as a potential target for these cancers. The development of Hsp90 isoform-selective inhibitors is hindered by >85% identity within the N-terminal ATP-binding site of all four isoforms which poses a significant challenge to the rational design of Hsp90 isoform-selective inhibitors.[9]

The nucleotide binding site of Grp94 is the most unique among the four isoforms, due to a five amino acid insertion into its primary sequence, which results in secondary binding pockets that can be exploited for selective inhibition. The first Grp94-selective inhibitor was developed via incorporation of a cis-amide bioisostere into the radamide scaffold 1 (see Scheme A below) to predispose the side chain into the Grp94 exclusive pocket, ultimately leading to the development of BnIm 2, which manifested ~12-fold selectivity via a fluorescence polarization assay.[10] Subsequent structure-activity relationship studies on the benzyl side chain of 2 resulted in the development of 3, which exhibited improved affinity and selectivity for Grp94 as compared to 2.[11] Interestingly, substitutions at the 2-position of the benzyl side chain (3-5) manifested the greatest Grp94-selectivity.

Scheme A

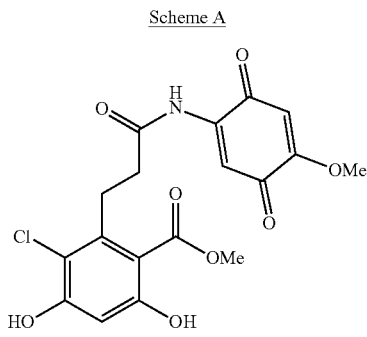

1
Radamide
pan-Hsp90 inhibitor

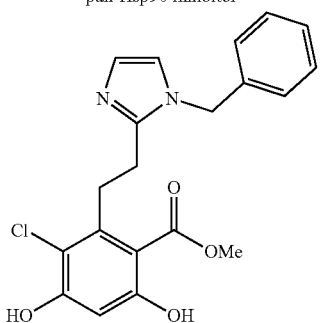

2
Bnim
App $K_d$ Grp94: 1.14 μM
12-fold Grp94 selective

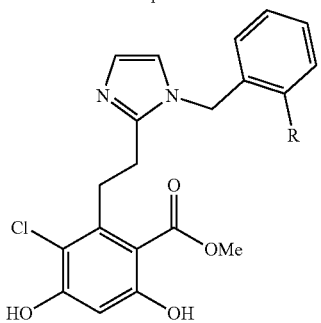

3 R = -OEt
KUNG29
App. $K_d$ Grp94: 0.20 μM
41-fold Grp94 selective

4 R = -OMe
App. $K_d$ Grp94: 1.3 μM
41-fold Grp94 selective

5 R = -Et
App. $K_d$ Grp94: 0.81 μM
48-fold Grp94 selective

The present technology provides compounds selective for the Grp94 isoform, as well as compositions including such compounds, that are useful for treatment of multiple myeloma, melanoma, lung cancer, hepatocellular carcinoma, breast cancer, prostate cancer, and/or glaucoma.

Thus, in an aspect, provided is a compound of Formula I

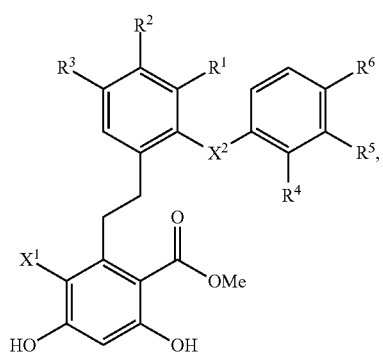

or a pharmaceutically acceptable salt thereof, wherein
$X^1$ is Cl of F;
$X^2$ is CH S or
$R^1$, $R^2$, $R^4$, $R^5$, and $R^6$ are each independently H, alkoxy, hydroxyl, thiol, or halo; and
$R^3$ is H, alkoxy, amino, hydroxyl, thiol, or halo.

As another example, the compound of Formula I is a compound of Formula II:

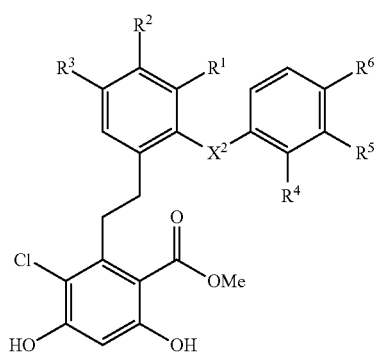

or a pharmaceutically acceptable salt thereof.

In any embodiment herein, it may be that when $X^2$ is O and $R^4$, $R^5$, and $R^6$ are each independently H, then $R^1$ and $R^2$ may each independently be H, alkoxy, or halo; and $R^3$ may be H, alkoxy, amino, or halo. In any embodiment herein, it may be that at least two of $R^1$, $R^2$, and $R^3$ are each independently H. In any embodiment herein, at least two of $R^4$, $R^5$, and $R^6$ may each independently be H. In any embodiment herein, it may be that at least one of $R^1$, $R^2$, and $R^3$ is hydroxyl, then at least one of $R^4$, $R^5$, and $R^6$ may not be H. In any embodiment herein, it may be that when one of $R^1$, $R^2$, and $R^3$ is hydroxyl and the remaining $R^1$, $R^2$, and $R^3$ each independently are H, then at least one of $R^4$, $R^5$, and $R^6$ may not be H. In some embodiments herein, $R^1$, $R^2$, and $R^3$ are each independently H.

In an aspect, provided is a compound of Formula III

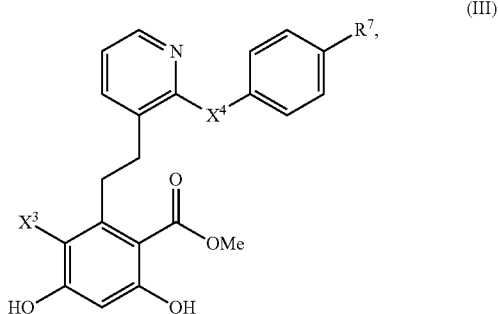

(III)

or a pharmaceutically acceptable salt thereof, wherein
$X^3$ is Cl or F;
$X^4$ is $CH_2$, O, S, or NH; and
$R^7$ is alkoxy, hydroxyl, thiol, or halo.

The present technology also provides compositions (e.g., pharmaceutical compositions) and medicaments comprising any of one of the embodiments of the compounds of Formula I, II or III (or a pharmaceutically acceptable salt of any thereof) disclosed herein and a pharmaceutically acceptable carrier or one or more excipients or fillers (collectively referred to as "pharmaceutically acceptable carrier" unless otherwise specified). The compositions may be used in the methods and treatments described herein. The pharmaceutical composition may include an effective amount of any of one of the embodiments of the compounds of the present technology disclosed herein. In any of the above embodiments, the effective amount may be determined in relation to a subject. "Effective amount" refers to the amount of a compound or composition required to produce a desired effect. One non-limiting example of an effective amount includes amounts or dosages that yield acceptable toxicity and bioavailability levels for therapeutic (pharmaceutical) use including, but not limited to, the treatment of e.g., multiple myeloma, melanoma, lung cancer, hepatocellular carcinoma, breast cancer, glaucoma (e.g. myocilin glaucoma), or prostate cancer. Any of the cancers may be metastatic. Another example of an effective amount includes amounts or dosages that are capable of reducing symptoms associated with e.g., multiple myeloma, melanoma, lung cancer, hepatocellular carcinoma, breast cancer, or prostate cancer, such as, for example, reduction in proliferation and/or metastasis of multiple myeloma, melanoma, lung cancer, hepatocellular carcinoma, breast cancer, or prostate cancer. The effective amount may be from about 0.01 µg to about 200 mg of the compound per gram of the composition, and preferably from about 0.1 µg to about 10 mg of the compound per gram of the composition. As used herein, a "subject" or "patient" is a mammal, such as a cat, dog, rodent or primate. Typically the subject or patient is a human, and, preferably, a human suffering from or suspected of suffering from multiple myeloma, melanoma, lung cancer, hepatocellular carcinoma, breast cancer, glaucoma (e.g. myocilin glaucoma), or prostate cancer. The term "subject" and "patient" can be used interchangeably.

In any of the embodiments of the present technology described herein, the pharmaceutical composition may be packaged in unit dosage form. The unit dosage form is effective in treating multiple myeloma, melanoma, lung cancer, hepatocellular carcinoma, breast cancer, glaucoma (e.g. myocilin glaucoma), or prostate cancer. Any of the cancers may be metastatic. Generally, a unit dosage including a compound of the present technology will vary depending on patient considerations. Such considerations include, for example, age, protocol, condition, sex, extent of disease, contraindications, concomitant therapies and the like. An exemplary unit dosage based on these considerations may also be adjusted or modified by a physician skilled in the art. For example, a unit dosage for a patient comprising a compound of the present technology may vary from $1 \times 10^{-4}$ g/kg to 1 g/kg, preferably, $1 \times 10^{-3}$ g/kg to 1.0 g/kg. Dosage of a compound of the present technology may also vary from 0.01 mg/kg to 100 mg/kg or, preferably, from 0.1 mg/kg to 10 mg/kg. Suitable unit dosage forms, include, but are not limited to powders, tablets, pills, capsules, lozenges, suppositories, patches, nasal sprays, injectibles, implantable sustained-release formulations, mucoadherent films, topical varnishes, lipid complexes, etc.

The pharmaceutical compositions may be prepared by mixing one or more compounds of Formulas I, II and III, pharmaceutically acceptable salts thereof, stereoisomers thereof, tautomers thereof, or solvates thereof, with pharmaceutically acceptable carriers, excipients, binders, diluents or the like to prevent and treat disorders associated with cancer (e.g., multiple myeloma, melanoma, lung cancer, hepatocellular carcinoma, breast cancer, or prostate cancer). The compounds and compositions described herein may be used to prepare formulations and medicaments that treat e.g., multiple myeloma, melanoma, lung cancer, hepatocellular carcinoma, breast cancer, glaucoma (e.g. myocilin glaucoma) or prostate cancer. Such compositions may be in the form of, for example, granules, powders, tablets, capsules, syrup, suppositories, injections, emulsions, elixirs, suspensions or solutions. The instant compositions may be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular, injections. The following dosage forms are given by way of example and should not be construed as limiting the instant present technology.

For oral, buccal, and sublingual administration, powders, suspensions, granules, tablets, pills, capsules, gelcaps, and caplets are acceptable as solid dosage forms. These can be prepared, for example, by mixing one or more compounds of the instant present technology, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations, compositions, and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aqueous and nonaqueous (e.g., in a fluorocarbon propellant) aerosols are typically used for delivery of compounds of the present technology by inhalation.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference. The instant compositions may also include, for example, micelles or liposomes, or some other encapsulated form.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Various assays and model systems can be readily employed to determine the therapeutic effectiveness of the treatment according to the present technology.

For the indicated condition, test subjects will exhibit a 10%, 20%, 30%, 50% or greater reduction, up to a 75-90%, or 95% or greater, reduction, in one or more symptom(s) caused by, or associated with, the disorder in the subject, compared to placebo-treated or other suitable control subjects.

In a related aspect, a method for inhibiting cell motility of a cancer cell is provided, the method comprising contacting the cancer cell with a compound disclosed herein. The cancer cell may be a metastatic multiple myeloma cancer cell, a metastatic melanoma cancer cell, a metastatic lung cancer cell, a metastatic hepatocellular carcinoma cell, a metastatic breast cancer cell, or a metastatic prostate cancer cell. The cancer considered herein for treatment is not limited. The cancer of any of the methods disclosed herein can be essentially any type of cancer. The method may include contacting the cell with an effective amount of the compound. The cancer cell may not be within a patient. The contacting me be in vivo, in vitro, or ex vivo. Some examples of applicable body parts containing cancer cells include the breasts, lungs, stomach, intestines, prostate, ovaries, cervix, pancreas, kidney, liver, skin, lymphs, bones, bladder, uterus, colon, rectum, and brain.

In a related aspect, a method of treating a patient or animal suffering from metastatic cancer is provided, the method comprising administration of an effective amount of a compound disclosed herein to the patient or animal suffering from the metastatic cancer. Administration of the effective amount of the compound to the patient or animal may treat the patient or animal suffering from the metastatic cancer. The metastatic cancer may be multiple myeloma, melanoma, lung cancer, hepatocellular carcinoma, breast cancer, or prostate cancer. The administration may include oral administration, parenteral administration, or nasal administration. The compounds described herein may be administered by injection into the bloodstream. In some embodiments, the compound may be administered locally, at the site where the target cells are present, i.e., in a specific tissue, organ, or fluid (e.g., blood, cerebrospinal fluid, etc.). Some examples of applicable body parts containing cancer cells include the breasts, lungs, stomach, intestines, prostate, ovaries, cervix, pancreas, kidney, liver, skin, lymphs, bones, bladder, uterus, colon, rectum, and brain. The cancer can also include the presence of one or more carcinomas.

In a related aspect, a method of inhibiting death of a cell exhibiting mutant myocilin is provided, the method comprising contacting the cell with a compound disclosed herein. The method may include contacting the cell with an effective amount of the compound. The contacting may inhibit the death of the cell in comparison to a cell exhibiting mutant myocilin that is not contacted with the compound.

In a related aspect, a method of treating a patient or animal suffering from glaucoma is provided, the method comprising administration of an effective amount of a compound disclosed herein. Administration of the effective amount of the compound to the patient or animal may treat the patient or animal suffering from the cancer or the glaucoma. The glaucoma may be myocilin glaucoma.

In different embodiments of any of the methods of treatment herein, an effective amount may be precisely, at least, above, up to, or less than, for example, 1 mg, 10 mg, 50 mg, 100 mg, 200 mg, 300 mg, 400 mg, 500 mg, 600 mg, 700 mg, 800 mg, 900 mg, 1000 mg, 1200 mg, or 1500 mg, or a dosage within a range bounded by any of the foregoing exemplary dosages. Furthermore, the composition can be administered in the indicated amount by any suitable schedule, e.g., once, twice, or three times a day or on alternate days for a total treatment time of one, two, three, four, or five days, or one, two, three, or four weeks, or one, two, three, four, five, or six months, or within a time frame therebetween. Alternatively, or in addition, the composition can be administered until a desired change in the disorder or condition is realized, or when a preventative effect is believed to be provided.

The examples herein are provided to illustrate advantages of the present technology and to further assist a person of ordinary skill in the art with preparing or using the compounds of the present technology or salts, pharmaceutical compositions, derivatives, prodrugs, or tautomeric forms thereof. The examples herein are also presented in order to more fully illustrate the preferred aspects of the present technology. The examples should in no way be construed as limiting the scope of the present technology, as defined by the appended claims. The examples can include or incorporate any of the variations, aspects or embodiments of the present technology described above. The variations, aspects or embodiments described above may also further each include or incorporate the variations of any or all other variations, aspects or embodiments of the present technology.

EXAMPLES

Example 1: Exemplary Synthetic Procedures and Characterization

Chemistry General $^1$H NMR were recorded at 400 (Bruker AVIIIHD 400 MHz NMR with a broadband X-channel detect gradient probe) or 500 MHz (Avance AVIII 500 MHz spectrometer with a dual carbon/proton cryoprobe), and $^{13}$C NMR were recorded at 125 MHz (Bruker AVII spectrometer equipped with a cryogenically cooled carbon observe probe); chemical shifts are reported in δ (ppm) relative to the internal standard (CDCl3, 7.26 ppm for $^1$H and 77.2 for $^{13}$C). HRMS spectra were recorded with a LCT Premier with ESI ionization. All biologically tested compounds were determined to be >95% pure TLC analysis was performed on glass backed silica gel plates and visualized by UV light. All solvents were reagent grade and used without further purification.

Referring to Scheme 1, below, synthesis of 6 and 7, proceeded via a Heck coupling between aryl bromide 8 and 2- or 3-benzylstyrene (9a and 9b, respectively), followed by hydrogenolysis of the benzyl ethers and concomitant reduction of the alkene. Aryl bromide 8 was synthesized from 1-bromo-3,5-dimethoxybenzene 10 in 6 steps, 28% overall yield, and required only one chromatographic separation. 10 was demethylated via pyridinium hydrochloride, which provided the free phenols after an acidic workup. The phenols were subsequently converted to the benzyl ethers 11 upon treatment with benzyl bromide and potassium carbonate. Silver-promoted formylation of 11 and Pinnick oxidation yielded benzoic acid 12.[13] Conversion of 12 to the corresponding methyl ester was achieved upon exposure to dimethyl sulfate. Regioselective chlorination was achieved upon reaction with sulfuryl chloride at −30° C., which provided the desired resorcinol, 8.[14] Synthesis of 9a and 9b commenced via a palladium-catalyzed cross coupling reaction between commercially available 2- and 3-formylphenyl boronic acid and benzyl bromide to provide the corresponding 2- and 3-benzylbenzaldehydes (13a and 13b, respectively). Subsequent Wittig olefination afforded the 2- and 3-benzylstyrenes (9a and 9b, respectively), which were then subjected to Heck olefination conditions with aryl bromide 8.[15] Hydrogenolysis of the benzyl ethers and reduction of the olefin under a hydrogen atmosphere provided 6 and 7.

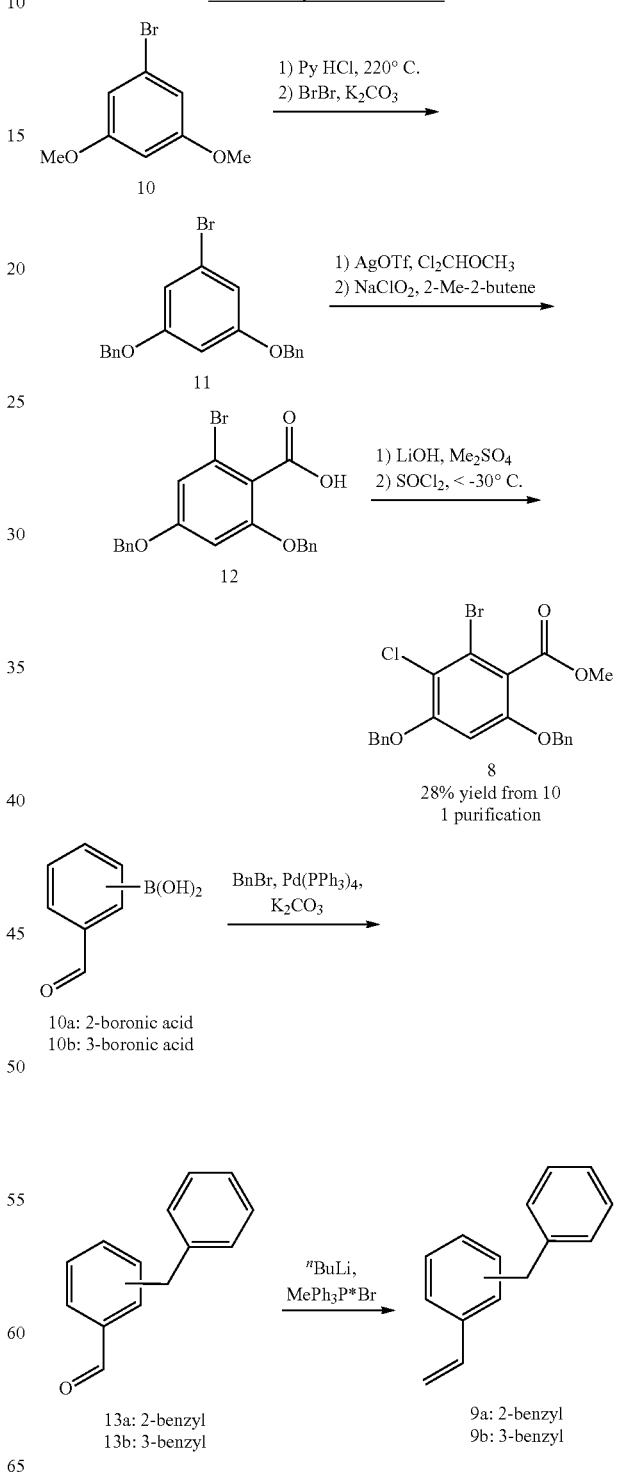

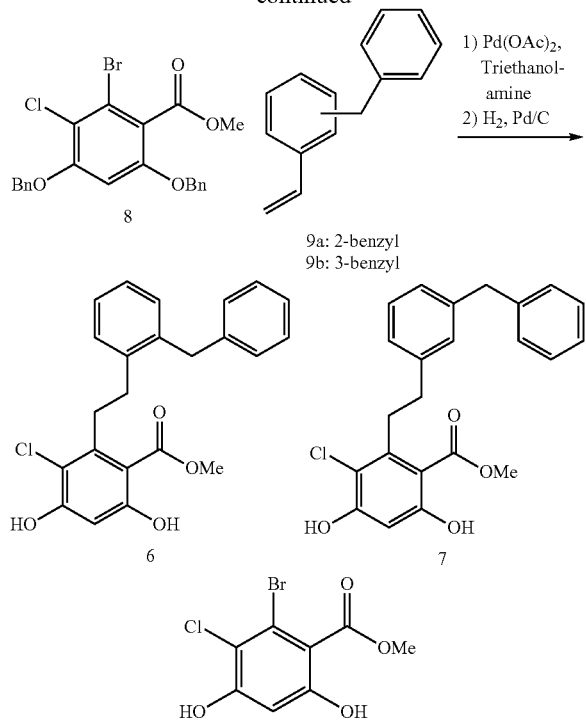

methyl 4,6-bis(benzyloxy)-2-bromo-3-chlorobenzoate (8). 1-bromo-3,5-dimethoxybenzene (5 g, 23 mmol, 1 eq.) was added to a round bottom flask containing pyridinium hydrochloride (20 g, 173 mmol, 7.5 eq.). The mixture was heated to 220° C. for 3 h and poured in water (100 mL), diluted with EtOAc (200 mL). The aqueous layer was made acidic via the addition of 3N HCl (100 mL). The aqueous layer was extracted with EtOAc (3×100 mL). The organic layers were combined, dried over anhydrous $Na_2SO_4$, and concentrated and used as obtained. The residue was diluted in DMF (50 mL) followed by the addition of $K_2CO_3$ (11 g) and BnBr (4 mL). The mixture was stirred at rt for 14 h at which point water (200 mL) and EtOAc (300 mL) were added. The organic layer was washed with water (5×150 mL), brine (1×100 mL), dried over anhydrous $Na_2SO_4$, and concentrated to provide 11 as a white amorphous solid which was used without further purification. 11 was dissolved in dry DCM (150 mL) followed by the addition of AgOTf (12.6 g). The mixture was cooled to −78° C. and 1,1-dichloromethylmethyl ether (4.4 mL) was added dropwise over 5 min. The reaction mixture was stirred at −78° C. for 30 min followed by removal from the cold bath and quenched with saturated $NaHCO_3$ (150 mL). The mixture was stirred for 1 h at rt the filtered through a pad of celite. The aqueous layer was extracted with DCM (2×100 mL). The organic layers were combined, dried over $Na_2SO_4$, and concentrated. The residue obtained was used without further purification. The residue was dissolved in a mixture of t-BuOH:2-methyl-2-butene-water (2:2:1) followed by the addition of $NaClO_2$ (2.4 g) and $NaH_2PO_4$ (4.7 g). The reaction was stirred at it for 14 h and quenched with saturated $NaH_2PO_4$ (100 mL). The aqueous layer was extracted with EtOAc (3×100 mL). The organic layers were combined, dried, and concentrated to provide crude 12, which was used without further purification. 12 was dissolved in THF (200 mL) followed by the addition of LiOH (0.7 g) and $Me_2SO_4$ (1.5 mL) and stirred at 50° C. for 8 h (no starting material remaining). Saturated $NH_4Cl$ (200 mL) was added to the reaction mixture and stirred at 50° C. for 1 h, then cooled to rt, and the aqueous layer was extracted with EtOAc (3×100 mL). The organic layers were combined, dried, and concentrated. The resultant residue was dissolved in THF (150 mL) and cooled to −40° C. followed by the addition of $SO_2Cl_2$ dropwise over 15 min (temperature maintained <−30° C. during addition). The reaction was stirred at −40° C. for 30 min and quenched with saturated $NH_4Cl$ and extracted with $Et_2O$ (3×100 mL). The organic layers were combined, dried, and concentrated. The residue was purified via flash chromatography ($SiO_2$, 15% EtOAc in Hexanes) to provide 8 was an off white amorphous solid (3 g, 28%). $^1H$ NMR (400 MHz, Chloroform-d) δ 7.38-7.34 (m, 7H), 7.32-7.28 (m, H), 6.51 (s, 1H), 5.08 (s, 2H), 5.02 (s, 2H), 3.91 (s, 3H). $^{13}C$ NMR (126 MHz, CDCl3) δ 166.3, 156.1, 155.0, 135.8, 135.6, 128.9 (2C), 128.8 (2C), 128.5, 128.4, 127.1 (2C), 127.0 (2C), 121.4, 121.0, 117.0, 99.6, 71.5, 71.3, 53.0. HRMS [M+H]$^+$ for $C_{22}H_{19}BrClO_4$ 461.0155. found 461.0143.

General Procedure for the Synthesis of 13a-13d, 13l-13q

As shown in Scheme 1 above and Scheme 2 herein, a microwave vial was charged with 2- or 3-formylphenyl boronic acids (10a-d, 1 eq.), tetrakis(triphenylphosphine) palladium(0) (0.025 eq.), benzyl bromide (13a-13d) or substituted benzyl bromide (13l-13q, shown in Scheme 3 below) (1 eq.) and sealed with a disposable Teflon lined cap. The tube was evacuated and purged with argon (3×) followed by the addition of THF (0.2 M) and 2M $K_2CO_3$ (3 eq.). The reaction mixture was heated to 95° C. for 12 h, cooled to rt, and diluted with $Et_2O$ (10 mL) and water (15 mL). The aqueous layer was extracted with $Et_2O$ (3×10 mL). The organic layers were combined, dried, and concentrated. The resulting residue was purified via flash chromatography ($SiO_2$, 1:9 EtOAc:Hexanes) to provide the desired benzaldehydes (13a-13d, 13l-13q).

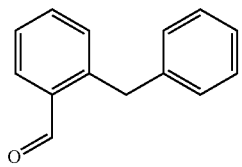

2-benzylbenzaldehyde (13a). Clear oil (220 mg, 67%). $^1H$ NMR (400 MHz, Chloroform-d) δ 10.26 (s, 1H), 7.87 (dd, J=7.7, 1.5 Hz, 1H), 7.53 (td, J=7.5, 1.5 Hz, 1H), 7.42 (t, J=7.5 Hz, 1H), 7.29-7.24 (m, 3H), 7.23-7.17 (m, 1H), 7.15 (d, J=7.6 Hz, 2H), 4.46 (s, 2H). $^{13}C$ NMR (126 MHz, CDCl3) δ 192.8, 143.4, 140.7, 134.3, 134.3, 132.4, 132.1, 129.2 (2C), 129.0 (2C), 127.4, 126.7, 38.4. HRMS (ESI) [M+H]$^-$ for $C_{14}H_{13}O$ 197.0966. found 197.0976.

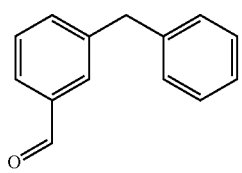 [SMILES: O=Cc1cccc(Cc2ccccc2)c1]

3-benzylbenzaldehyde (13b). Clear oil (165 mg, 50%) $^1H$ NMR (400 MHz, Chloroform-d) δ 9.98 (s, 1H), 8.01-7.91 (m, 1H), 7.72 (d, J=2.3 Hz, 1H), 7.49-7.36 (m, 2H), 7.31

(ddd, J=7.8, 6.5, 1.9 Hz, 2H), 7.20 (dd, J=7.7, 6.1 Hz, 3H), 4.06 (d, J=6.1 Hz, 2H). HRMS (ESI) [M+H]$^+$ for $C_{14}H_{13}O$ 197.0966. found 197.0963.

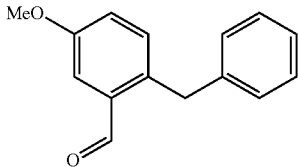

2-benzyl-5-methoxybenzaldehyde (13c). Clear oil (230 mg, 73%).$^1$H NMR (400 MHz, Chloroform-d) δ 10.22 (s, 1H), 7.37 (d, J=2.9 Hz, 1H), 7.27-7.21 (m, 2H), 7.17 (d, J=8.0 Hz, 2H), 7.11-7.04 (m, 3H), 4.34 (s, 2H), 3.83 (s, 3H).$^{13}$C NMR (126 MHz, CDCl3) δ 191.6, 158.4, 140.6, 135.3, 134.5, 132.8, 128.5 (2C), 128.4 (2C), 126.1, 120.8, 113.9, 55.4, 36.9. HRMS (ESI) [M+Na]$^+$ for $C_{15}H_{14}O_2Na$ 249.0892. found 249.0889.

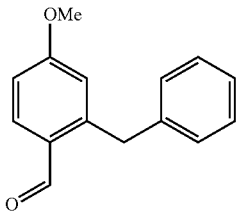 [SMILES: COc1ccc(C=O)c(Cc2ccccc2)c1]

2-benzyl-4-methoxybenzaldehyde (13d). Clear oil (470 mg, 75%).$^1$H NMR (400 MHz, Chloroform-d) δ 10.13 (s, 1H), 7.85 (d, J=8.5 Hz, 1H), 7.29 (d, J=7.3 Hz, 2H), 7.21 (dd, J=17.3, 7.4 Hz, 3H), 6.91 (dd, J=8.6, 2.5 Hz, 1H), 6.75 (d, J=2.5 Hz, 1H), 4.45 (s, 2H), 3.86 (s, 3H).$^{13}$C NMR (126 MHz, CDCl3) δ 191.0, 164.0, 145.7, 140.1, 135.1, 128.9, 128.7, 127.7, 126.4, 117.3, 111.9, 108.6, 100.8, 55.6, 38.3. HRMS (ESI) [M+H]$^+$ for $C_{15}H_{15}O_2$ 227.1072. found 227.1062.

2-(2-ethoxybenzyl)benzaldehyde (13l). Clear oil (275 mg, 43%)$^1$H NMR (400 MHz, Chloroform-d) δ 10.38 (s, 1H), 7.88 (dd, J=7.7, 1.5 Hz, 1H), 7.49 (td, J=7.5, 1.5 Hz, 1H), 7.42-7.33 (m, 1H), 7.31-7.25 (m, 2H), 7.18 (td, J=7.8, 1.8 Hz, 1H), 7.04-6.92 (m, 1H), 6.90-6.80 (m, 2H), 4.41 (s, 2H), 4.03 (q, J=7.0 Hz, 2H), 1.36 (t, J=7.0 Hz, 3H).$^{13}$C NMR (126 MHz, CDCl3) δ 192.9, 156.7, 144.0, 134.4, 134.2, 131.8, 130.5, 130.4, 129.3, 128.1, 127.0, 120.8, 111.5, 63.9, 32.2, 15.2. HRMS (ESI) [M+H]$^+$ for $C_{16}H_{17}O_2$ 241.1229. found 241.1226.

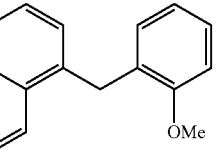

2-(2-methoxybenzyl)benzaldehyde (13m). clear oil (230 mg, 51%)$^1$H NMR (400 MHz, Chloroform-d) δ 10.36 (s, 1H), 7.88 (dd, J=7.7, 1.4 Hz, 1H), 7.53-7.46 (m, 1H), 7.37 (t, J=7.5 Hz, 1H), 7.25-7.16 (m, 2H), 6.94 (dd, J=7.4, 1.6 Hz, 1H), 6.91-6.82 (m, 2H), 4.40 (s, 2H), 3.81 (s, 3H).$^{13}$C NMR (126 MHz, CDCl3) δ 192.3, 156.8, 143.2, 133.9, 133.7, 131.2, 130.1, 129.9, 128.6, 127 6, 126.5, 120.5, 110.1, 55.1, 31.7. HRMS (ESI) [M+H]$^+$ for $C_{15}H_{15}O$ 227.1076. found 227.1072.

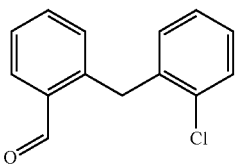 [SMILES: O=Cc1ccccc1Cc1ccccc1Cl]

2-(2-chlorobenzyl)benzaldehyde (13n). yellow oil (160 mg, 35%)$^1$H NMR (400 MHz, Chloroform-d) δ 10.23 (s, 1H), 7.89 (dd, J=7.7, 1.5 Hz, 1H), 7.53 (ddd, J=15.1, 8.1, 1.6 Hz, 2H), 7.46-7.38 (m, 2H), 7.20-7.10 (m, 3H), 7.02 (td, J=8.5, 8.0, 7.0 Hz, 1H), 6.94 (dd, J=7.2, 2.1 Hz, 1H), 4.56 (s, 2H).$^{13}$C NMR (126 MHz, CDCl3) δ 192.4, 141.4, 136.9, 133.9, 132.3, 130.9, 130.6, 129.4, 127.8, 127.0, 126.9, 119.7, 117.5, 35.6. HRMS (ESI) [M+H]$^+$ for $C_{14}H_{12}ClO$ 231.0577. found 231.0581.

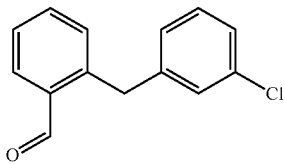 [SMILES: O=Cc1ccccc1Cc1cccc(Cl)c1]

2-(3-chlorobenzyl)benzaldehyde (13o). yellow oil (100 mg, 22%)$^1$H NMR (400 MHz, Chloroform-d) δ 10.19 (s, 1H), 7.86 (dd, J=7.6, 1.5 Hz, 1H), 7.55 (td, J=7.5, 1.6 Hz, 1H), 7.45 (td, J=7.6, 1.2 Hz, 1H), 7.30-7.24 (m, 1H), 7.23-7.15 (m, 2H), 7.12 (d, J=1.9 Hz, 1H), 7.07-7.01 (m, 1H), 4.43 (s, 2H).$^{13}$C NMR (126 MHz, CDCl3) δ 192.7, 142.4, 142.0, 134.5, 134.1, 134.0, 133.3, 131.9, 129.9, 129.0, 127.4, 127.2, 126.6, 37.9. HRMS (ESI) [M+H]$^+$ for $C_{14}H_{12}ClO$ 231.0577. found 231.0574.

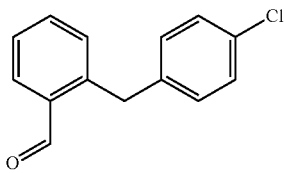 [SMILES: O=Cc1ccccc1Cc1ccc(Cl)cc1]

2-(4-chlorobenzyl)benzaldehyde (13p). yellow oil (145 mg, 31%)$^1$H NMR (400 MHz, Chloroform-d) δ 10.19 (s, 1H), 7.85 (dd, J=7.6, 1.5 Hz, 1H), 7.54 (td, J=7.5, 1.6 Hz, 1H), 7.45 (dd, J=7.5, 1.2 Hz, 1H), 7.26 (d, J=1.7 Hz, 1H), 7.25-7.23 (m, 2H), 7.08 (d, J=8.4 Hz, 2H), 4.42 (s, 2H).$^{13}$C NMR (126 MHz, CDCl3) δ 192.7, 142.4, 138.9, 134.1, 134.0, 133.3, 132.2, 131.8, 130.3 (2C), 128.8 (2C), 127.4, 37.7. HRMS (ESI) [M+Na]+ for $C_{14}H_{12}ClO$ 253.0396. found 253.0387.

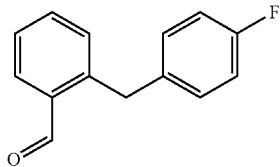 [SMILES: O=Cc1ccccc1Cc1ccc(F)cc1]

2-(4-fluorobenzyl)benzaldehyde (13q) yellow oil (320 mg, 75%) $^1$H NMR (400 MHz, Chloroform-d) δ 10.21 (s, 1H), 7.85 (dd, J=7.6, 1.5 Hz, 1H), 7.54 (td, J=7.5, 1.6 Hz, 1H), 7.44 (td, J=7.5, 1.2 Hz, 1H), 7.25 (d, J=8.3 Hz, 1H), 7.11 (dd, J=8.6, 5.5 Hz, 2H), 6.96 (t, J=8.7 Hz, 2H), 4.42 (s, 2H).$^{13}$C NMR (126 MHz, CDCl3) δ 192.7, 142.9, 134.1, 133.0, 131.9, 131.7, 131.2, 130.4, 130.3, 127.3, 122.1, 115.5, 115.4, 37.5. HRMS (ESI) [M+H]+ for $C_{14}H_{12}FO$ 215.0872. found 215.0880.

General Procedure for the Synthesis of 13e-13 h

As shown in Scheme 2 below, a microwave vial was charged with aryl bromides (14a-d, 1 eq.), potassium benzyltrifluoroborate (1.5 eq.), palladium (II) acetate (0.08 eq.), RuPhos (0.17 eq.), and $K_3PO_4$ (5.2 eq.). The tube was sealed with a disposable Teflon lined lid and evacuate and purged with argon (3×) followed by the addition of mixture of toluene:water (5:1, 0.1 M). The reaction mixture was heated to 115° C. for 16 h, cooled to rt, and diluted with water (10 mL) and EtOAc (20 mL). The aqueous layer was extracted with EtOAc (2×20 mL) and the organic layers were combined, dried, and concentrated. The resulting residue was purified via flash chromatography ($SiO_2$, 1:5 EtOAc:Hexanes) to provide the desired benzaldehydes (13e-13 h).

Scheme 2: Synthesis of 16-24

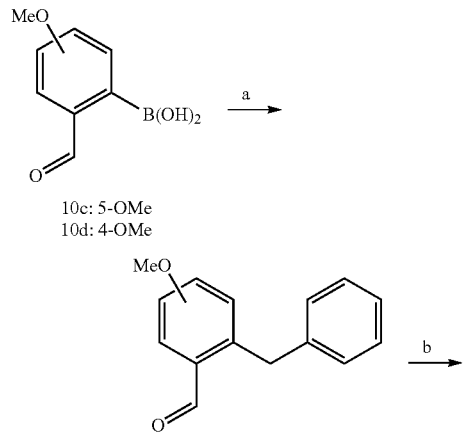

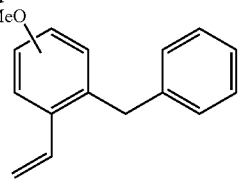

9c: 5-OMe
9d: 4-OMe

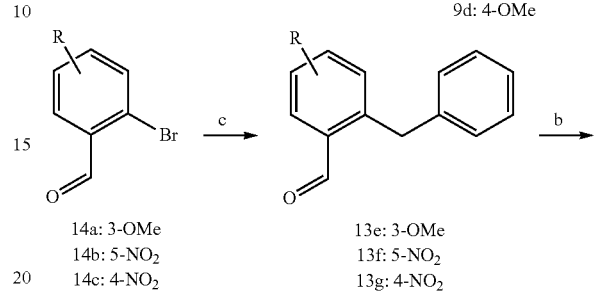

14a: 3-OMe
14b: 5-NO2
14c: 4-NO2

13e: 3-OMe
13f: 5-NO2
13g: 4-NO2

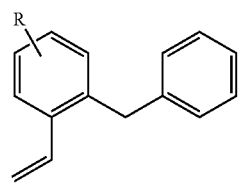

9e: 3-OMe
9f: 5-NO2
9g: 4-NO2

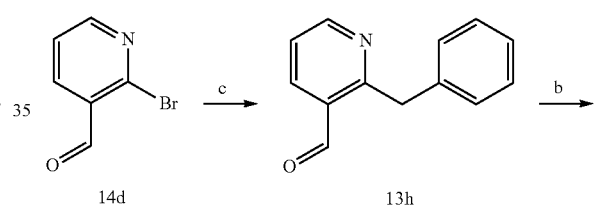

14d

13h

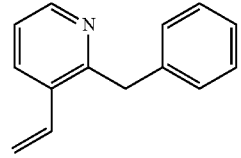

9h

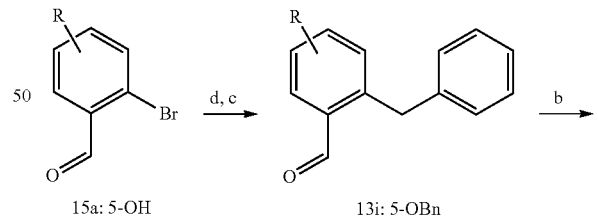

15a: 5-OH
15b: 4-OH
15c: 3-OH

13i: 5-OBn
13j: 4-OBn
13k: 3-OBn

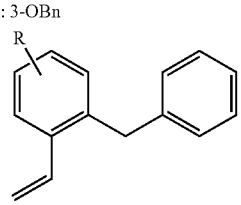

9i: 5-OBn
9j: 4-OBn
9k: 3-OBn

-continued

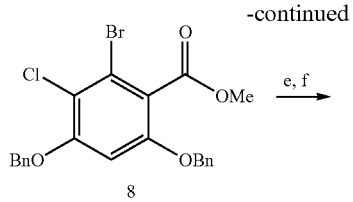

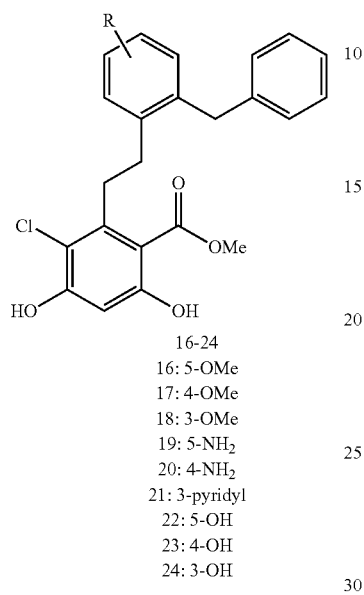

16-24
16: 5-OMe
17: 4-OMe
18: 3-OMe
19: 5-NH$_2$
20: 4-NH$_2$
21: 3-pyridyl
22: 5-OH
23: 4-OH
24: 3-OH Conditions: (a) Pd(PPh$_3$)$_4$, K$_2$CO$_3$; (b) MePh$_3$P$^+$Br$^-$, "BuLi; (c) Potassium benzyltrifluoroborate, Pd(OAc)$_2$, RuPhos, K$_3$PO$_4$; (d) BnBr, K$_2$CO$_3$; (e) 9c-9k, Pd(OAc)$_2$, triethanolamine; (f) H$_2$, Pd/C

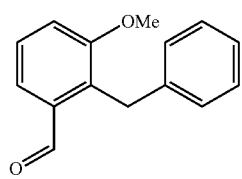 [SMILES: COc1cccc(C=O)c1Cc1ccccc1]

2-benzyl-3-methoxybenzaldehyde (13e). clear oil (110 mg, 70%) $^1$H NMR (400 MHz, Chloroform-d) δ 10.30 (s, 1H), 7.50 (d, J=7.7 Hz, 1H), 7.39 (t, J=7.9 Hz, 1H), 7.28-7.19 (m, 2H), 7.15 (d, J=7.1 Hz, 4H), 4.50 (s, 2H), 3.86 (s, 3H). $^{13}$C NMR (126 MHz, CDCl3) δ 192.3, 157.9, 140.5, 134.9, 131.5, 128.2, 128.2, 127.6, 125.8, 122.8, 121.3, 116.8, 115.9, 55.8, 29.4. HRMS (ESI) [M+Na]$^+$ for C$_{15}$H$_{15}$O$_2$ 249.0892. found 249.0890.

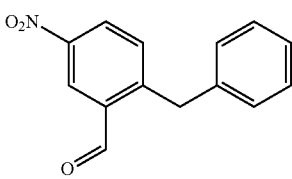 [SMILES: O=Cc1cc([N+](=O)[O-])ccc1Cc1ccccc1]

2-benzyl-5-nitrobenzaldehyde (13f). yellow oil (180 mg, 32%) $^1$H NMR (400 MHz, Chloroform-d) δ 10.31 (s, 1H), 8.71 (d, J=2.5 Hz, 1H), 8.34 (dd, J=8.4, 2.5 Hz, 1H), 7.46 (d, J=8.4 Hz, 1H), 7.34-7.28 (m, 2H), 7.27-7.21 (m, 1H), 7.13 (dd, J=6.9, 1.8 Hz, 2H), 4.54 (s, 2H). $^{13}$C NMR (126 MHz, CDCl3) δ 190.1, 150.0, 138.6, 134.7, 133.0, 129.1 (2C), 128.9 (2C), 127.9, 127.1 (2C), 126.7, 38.2. HRMS (ESI) [M+H]$^-$ for C$_{14}$H$_{12}$NO$_3$ 242.0817. found 242.0823

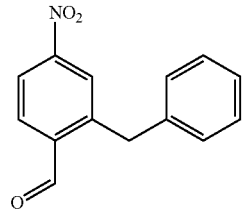 [SMILES: O=Cc1ccc([N+](=O)[O-])cc1Cc1ccccc1]

2-benzyl-4-nitrobenzaldehyde (13g). yellow oil (245 mg, 58%) $^1$H NMR (400 MHz, Chloroform-d) δ 10.37 (s, 1H), 8.23 (dd, J=8.5, 2.1 Hz, 1H), 8.13 (s, 1H), 8.05 (d, J=8.4 Hz, 1H), 7.32 (t, J=7.5 Hz, 2H), 7.26 (d, J=4.7 Hz, 2H), 7.14 (d, J=7.5 Hz, 2H), 4.53 (s, 2H). $^{13}$C NMR (126 MHz, CDCl3) δ 190.3, 150.4, 144.7, 138.4, 137.7, 132.3, 128.9, 128.6, 126.9, 126.3, 121.8, 37.7. HRMS (ESI) [M+H]$^+$ for C$_{14}$H$_{12}$NO$_3$ 242.0817. found 242.0825.

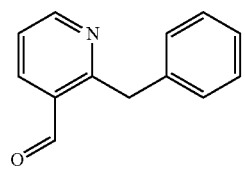 [SMILES: O=Cc1cccnc1Cc1ccccc1]

2-benzylnicolinaldehyde (13 h). clear oil (145 mg, 68%) $^1$H NMR (400 MHz, Chloroform-d) δ 10.34 (s, 1H), 8.77 (dd, J=4.8, 1.7 Hz, 1H), 8.14 (dt, J=7.9, 1.5 Hz, 1H), 7.37 (dd, J=7.8, 4.9 Hz, 1H), 7.31-7.16 (m, 5H), 4.60 (s, 2H). $^{13}$C NMR (126 MHz, CDCl3) δ 190.8, 162.1, 153.5, 138.8, 138.3, 129.3, 128.6 (2C), 128.5 (2C), 126.5, 122.2, 40.9. HRMS (ESI) [M+H]$^+$ for C$_{13}$H$_{12}$NO 198.0919. found 198.0928.

General Procedure for the Synthesis of 13i-13k.

As illustrated in Scheme 2 above, benzyl bromide (1.1 eq.) was added to a stirred solution of commercially available 15a-15c (1 eq.) and K$_2$CO$_3$ (2.5 eq.) in DMF (0.3 M). The reaction was stirred at rt for 13 h followed by the addition of water (30 mL) and EtOAc (40 mL). The organic layer was washed with water (5×30 mL) and brine (1×20 mL), dried, and concentrated. The resulting residue was passed through a filter column (SiO$_2$, 1:3 EtOAc:Hexanes) and used as obtained. The residue (1 eq.) was dissolved in toluene (5 mL) and transferred to a microwave vial that was charged with potassium benzyltrifluoroborate (1.5 eq.), palladium (II) acetate (0.08 eq.), RuPhos (0.17 eq.), and K$_3$PO$_4$ (5.2 eq.). The tube was sealed with a disposable Teflon lined lid and the solvent sparged with argon (10 min) followed by the addition of water (0.5 mL). The reaction mixture was heated to 115° C. for 16 h, cooled to rt, and diluted with water (10 mL) and EtOAc (20 mL). The aqueous layer was extracted with EtOAc (2×20 mL) and the organic layers were combined, dried, and concentrated. The resulting residue was purified via flash chromatography (SiO$_2$, 1:5 EtOAc:Hexanes) to provide the desired benzaldehydes (13i-13k).

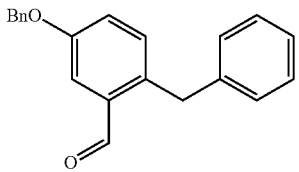

2-benzyl-5-(benzyloxy)benzaldehyde (13i). clear oil (195 mg, 32%)$^1$H NMR (400 MHz, Chloroform-d) δ 10.24 (d, J=1.6 Hz, 1H), 7.48 (q, J=1.9 Hz, 1H), 7.47-7.38 (m, 5H), 7.35 (td, J=6.8, 1.7 Hz, 1H), 7.31-7.25 (m, 1H), 7.19 (t, J=7.0 Hz, 3H), 7.16-7.11 (m, 2H), 5.11 (s, 2H), 4.38 (s, 2H).$^{13}$C NMR (126 MHz, CDCl3) δ 191.6, 157.6, 140.6, 136.3, 135.6, 134.5, 132.9, 130.0, 128.6, 128.6, 128.5, 128.1, 127.4, 126.1, 123.6, 122.1, 121.5, 115.1, 113.1, 70.1, 37.0. HRMS (ESI) [M+H]+ for $C_{21}H_{19}O_2$ 303.1385. found 303.1395.

2-benzyl-4-(benzyloxy)benzaldehyde (13j). clear oil (400 mg, 66%)$^1$H NMR (400 MHz, Chloroform-d) δ 10.11 (s, 1H), 7.82 (d, J=8.6 Hz, 1H), 7.43-7.33 (m, 5H), 7.31-7.27 (m, 2H), 7.23-7.17 (m, 1H), 7.17-7.13 (m, 2H), 6.96 (dd, J=8.6, 2.6 Hz, 1H), 6.80 (d, J=2.5 Hz, 1H), 5.09 (s, 2H), 4.42 (s, 2H).$^{13}$C NMR (126 MHz, CDCl3) δ 190.8, 162.8, 145.6, 139.8, 135.8, 134.9, 128.7 (2C), 128.6 (2C), 128.5 (2C), 128.2, 127.5, 127.5 (2C), 126.2, 117.7, 112.6, 70.0, 38.1. HRMS (ESI) [M+H]+ for $C_{21}H_{19}O_2$ 303.1385. found 303.1400.

2-benzyl-3-(benzyloxy)benzaldehyde (13k). clear oil (350 mg, 58%)$^1$H NMR (400 MHz, Chloroform-d) δ 10.32 (s, 1H), 7.54-7.47 (m, 2H), 7.37-7.31 (m, 3H), 7.29-7.25 (m, 2H), 723-7.20 (m, 2H), 7.19-7.10 (m, 4H), 5.10 (s, 2H), 4.55 (s, 2H).$^{13}$C NMR (126 MHz, CDCl3) δ 192.8, 157.5, 141.0, 136.9, 135.6, 132.5, 129.1, 128.9, 128.9, 128.7, 128.6, 128.4, 128.1, 127.9, 127.7, 127.4, 126.3, 123.6, 117.8, 71.0, 30.1. HRMS (ESI) [M+Na]+ for $C_{21}H_{18}O_2$ 325.1205. found 325.1205.

General Procedure for the Synthesis of 9a-9r.

"Butyl lithium (2.5 M in hexanes, 1.3 eq.) was added dropwise to a stirred solution of methytriphenylphosphonium bromide (1.5 eq.) in dry THF (0.1M) at 0° C. The mixture was stirred for 15 min before the addition of 13a-13r (1 eq. in 2 mL THF). The reaction was stirred at rt for 8 h at which point water was added dropwise and the aqueous layer was extracted with EtOAc (2×10 mL). The combined organic layers were dried, concentrated, and purified via flash chromatography (SiO2, 1:9 EtOAc:Hexanes) to provide the desired styrenes, 9a-9r.

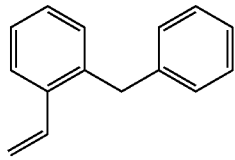

1-benzyl-2-vinylbenzene (9a). clear oil (197 mg, 90%)$^1$H NMR (400 MHz, Chloroform-d) δ 7.56-7.52 (m, 1H), 7.32-7.22 (m, 4H), 7.22-7.17 (m, 1H), 7.13 (d, J=7.5 Hz, 3H), 6.95 (dd, J=17.4, 11.0 Hz, 1H), 5.64 (d, J=17.2 Hz, 11H), 5.26 (dd, J=10.9, 1.6 Hz, 1H), 4.09 (s, 2H).$^{13}$C NMR (126 MHz, CDCl3) δ 141.0, 138.1, 137.4, 135.1, 130.8, 129.0 (2C), 128.8 (2C), 128.3, 127.1, 126.4, 126.3, 116.2, 39.4. HRMS (ESI) [M]+ for $C_{15}H_{14}$ 194.1096. found 194.1104.

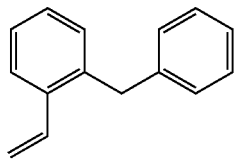

1-benzyl-3-vinylbenzene (9b). clear oil (142 mg, 87%)$^1$H NMR (400 MHz, Chloroform-d) δ 7.38-7.30 (m, 2H), 7.28 (d, J=7.5 Hz, 2H), 7.24 (d, J=2.5 Hz, 2H), 7.22-7.17 (m, 3H), 7.12-7.06 (m, 1H), 6.69 (dd, J=17.6, 10.9 Hz, 1H), 5.72 (d, J=176 Hz, 1H), 5.24 (s, 1H), 3.98 (s, 2H).$^{13}$C NMR (126 MHz, CDCl3) δ 137.2, 129.3 (2C), 129.0, 128.9, 128.8 (2C), 128.8, 128.7, 127.3, 126.5, 126.3, 124.4, 114.2, 42.3. HRMS (ESI) [M+H]+ for $C_{15}H_{14}$ 194.1096. found 194.1093.

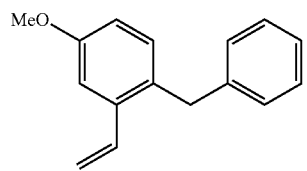

1-benzyl-4-methoxy-2-vinylbenzene (9c). clear oil (217 mg, 95%)$^1$H NMR (400 MHz, Chloroform-d) δ 7.30-7.22 (m, 3H), 7.17 (t, J=7.3 Hz, 1H), 7.14-7.03 (m, 4H), 6.90 (dd, J=17.3, 10.9 Hz, 1H), 6.80 (dd. J=8.4, 2.7 Hz, 1H), 5.63 (dd, J=17.3, 1.3 Hz, 1H), 5.24 (dd, J=10.9, 1.3 Hz, 1H), 4.01 (s, 2H), 3.83 (s, 3H).$^{13}$C NMR (126 MHz, CDCl3) δ 158.2, 140.9, 137.9, 134.6, 131.4, 130.1, 128.4 (2C), 128.3 (2C), 125.8, 115.7, 113.4, 110.9, 55.2, 38.0. MS (ESI) m/z [M+H]+ for $C_{16}H_{17}O$ 225.1279. found 225.1285.

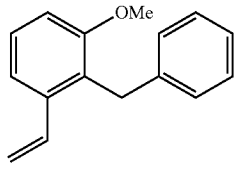 [SMILES: C=Cc1cccc(OC)c1Cc1ccccc1]

2-benzyl-1-methoxy-3-vinylbenzene (9e). clear oil (84 mg, 77%) ¹H NMR (400 MHz, Chloroform-d) δ 7.29-7.20 (m, 3H), 7.18 (d, J=1.3 Hz, 1H), 7.14 (t, J=7.0 Hz, 3H), 6.95 (dd, J=17.4, 11.0 Hz, 1H), 6.86 (d, J=8.1 Hz, 1H), 5.64 (dd, J=17.3, 1.5 Hz, 1H), 5.26 (dd, J=11.0, 1.5 Hz, 1H), 4.14 (s, 2H), 3.80 (d, J=1.2 Hz, 3H).¹³C NMR (126 MHz, CDCl3) δ 157.6, 140.8, 138.4, 134.8, 128.1, 128.1, 127.7, 127.1, 126.4, 125.4, 118.2, 116.1, 110.6, 109.7, 55.6, 31.0. HRMS (ESI) [M+Na]⁺ for $C_{16}H_{16}O$ 247.1094. found 247.1090.

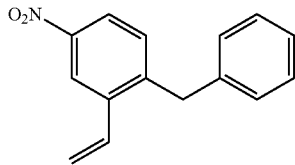 [SMILES: C=Cc1cc([N+](=O)[O-])ccc1Cc1ccccc1]

1-benzyl-4-nitro-2-vinylbenzene (9l). yellow oil (157 mg, 88%) ¹H NMR (400 MHz, Chloroform-d) δ 8.37 (d, J=2.4 Hz, 1H), 8.05 (dd, J=8.4, 2.5 Hz, 1H), 7.35-7.18 (m, 4H), 7.13-7.08 (m, 2H), 6.94 (dd, J=17.3, 11.0 Hz, 1H), 5.80 (dd, J=17.3, 0.9 Hz, 1H), 5.45 (dd, J=11.0, 0.9 Hz, 1H), 4.13 (s, 2H).¹³C NMR (126 MHz, CDCl3) δ 147.4, 145.5, 139.1, 138.9, 133.2, 131.6, 129.2 (2C), 129.1 (2C), 127.0, 122.7, 121.4, 119.3, 39.3. HRMS (ESI) m/z [M+H]⁺ for $C_{15}H_{14}NO_2$ 242.0817. found 242.0824.

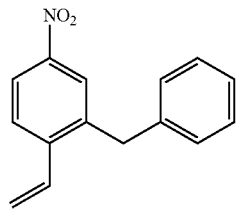 [SMILES: C=Cc1ccc([N+](=O)[O-])cc1Cc1ccccc1]

2-benzyl-4-nitro-1-vinylbenzene (9g). yellow oil (230 mg, 95%) ¹H NMR (400 MHz, Chloroform-d) δ 8.09 (dd, J=8.6, 2.3 Hz, 1H). 8.01 (d, J=2.3 Hz, 1H), 7.65 (d, J=8.6 Hz, 1H), 7.35-7.19 (m, 3H), 7.11 (d, J=7.4 Hz, 2H), 6.96 (dd, J=17.3, 11.0 Hz, 1H), 5.79 (d, J=17.4 Hz, 1H), 5.48 (d, J=11.0 Hz, 1H), 4.14 (s, 2H).¹³C NMR (126 MHz, CDCl3) δ 147.6, 143.9, 139.7, 139.2, 133.5, 129.2 (2C), 129.0 (2C), 127.2, 127.0, 125.8, 122.3, 120.3, 39.3. HRMS (ESI) m/z [M+H]⁺ for $C_{15}H_{14}NO_2$ 240.1025. found 240.1030.

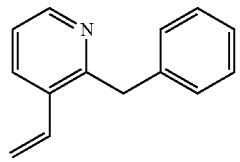

2-benzyl-3-vinylpyridine (9 h). yellow oil (97 mg, 68%) ¹H NMR (400 MHz, Chloroform-d) δ 8.50 (dd, J=4.8, 1.6 Hz, 1H), 7.77 (dd, J=7.8, 1.6 Hz, 1H), 7.34-7.13 (m, 6H), 6.94 (dd, J=17.4, 11.0 Hz, 1H), 5.64 (d, J=17.3 Hz, 1H), 5.35 (d, J=10.9 Hz, 1H), 4.27 (s, 2H).¹³C NMR (126 MHz, CDCl3) δ 157.3, 148.4, 139.2, 133.5, 133.0, 132.2, 128.5 (2C), 128.3 (2C), 126.0, 121.9, 117.5, 41.7. HRMS (ESI) [M+H]⁺ for $C_{14}H_{14}N$ 196.1126, found 196.1132.

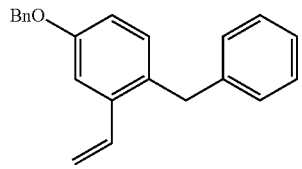 [SMILES: C=Cc1cc(OCc2ccccc2)ccc1Cc1ccccc1]

1-benzyl-4-(benzyloxy)-2-vinylbenzene (9i). clear oil (163 mg, 84%) ¹H NMR (400 MHz, Chloroform-d) δ 7.48 (d, J=8.6 Hz, 1H), 7.42-7.35 (m, 4H), 7.35-7.25 (m, 3H), 7.24-7.17 (m, 1H), 7.15-7.10 (m, 2H), 6.92-6.84 (m, 2H), 6.74 (d, J=2.6 Hz, 1H), 5.53 (dd, J=17.4, 1.4 Hz, 1H), 5.15 (dd, J=10.9, 1.4 Hz, 1H), 5.03 (s, 2H), 4.03 (s, 2H).¹³C NMR (126 MHz, CDCl3) δ 158.3, 140.2, 139.2, 136.8, 133.8, 129.8, 128.6 (2C), 128.5 (2C), 128.3 (2C), 127.8, 127.4 (2C), 126.9, 125.9, 116.5, 113.8, 112.9, 69.8, 39.0. HRMS (ESI) [M+Na]⁺ for $C_{22}H_{20}O$ 323.1412. found 323.1419.

2-benzyl-4-(benzyloxy)-1-vinylbenzene (9j). clear oil (372 mg, 94%) ¹H NMR (400 MHz, Chloroform-d) δ 7 48 (d, J=8.6 Hz, 1H), 7.43-7.35 (m, 4H), 7.34-7.30 (m, 1H), 7.29-7.23 (m, 3H), 7.23-7.16 (m, 1H), 7.15-7.10 (m, 2H), 6.96-6.83 (m, 2H), 6.74 (d, J=2.6 Hz, 1H), 5.53 (dd, J=17.4, 1.4 Hz, 1H), 5.15 (dd, J=10.9, 1.4 Hz, 1H), 5.03 (s, 2H), 4.03 (s, 2H).¹³C NMR (126 MHz, CDCl3) δ 158.9, 140.7, 139.7, 137.3, 134.4, 130.3, 129.1 (2C), 129.0 (2C), 128.8 (2C), 128.3, 127.9 (2C), 127.4, 126.4, 117.1, 114.3, 113.4, 70.3, 39.5. HRMS (ESI) [M+H]⁺ for $C_{22}H_{21}O$ 301.1592. found 301.1607.

2-benzyl-1-(benzyloxy)-3-vinylbenzene (9k). clear oil (322 mg, 93%) ¹H NMR (400 MHz, Chloroform-d) δ 7.44-7.29 (m, 2H), 7.27-7.20 (m, 2H), 7.18-7.09 (m, 4H), 7.07 (t, J=6.9 Hz, 3H), 6.91 (dd, J=17.3, 10.9 Hz, 1H), 6.81 (dd, J=7.0, 2.2 Hz, 1H), 5.56 (dd, J=17.3, 14 Hz, 1H), 5.19 (dd, J=11.0, 1.4 Hz, 1H), 4.97 (s, 2H), 4.10 (s, 2H).¹³C NMR (126 MHz, CDCl3) δ 156.9, 141.1, 138.9, 137.32, 135.1, 128.7, 128.7, 128.5, 128.5, 128.3, 127.8, 127.7, 127.4, 127.3, 127.2, 127.1, 125.7, 118.7, 116.5, 111.3, 70.3, 31.6. HRMS (ESI) [M+H]⁺ for $C_{22}H_{21}O$ 301.1592. found 301.1581.

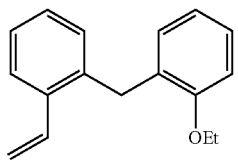 [SMILES: C=Cc1ccccc1Cc1ccccc1OCC]

1-ethoxy-2-(2-vinylbenzyl)benzene (9l). clear oil (249 mg, 91%) $^1$H NMR (400 MHz, Chloroform-d) δ 7.54 (dd, J=7.0, 2.2 Hz, 1H), 7.23-7.19 (m, 1H), 7.19-7.11 (m, 3H), 6.98 (dd, J=17.5, 11.1 Hz, 1H), 6.90-6.78 (m, 3H), 5.63 (dd, J=17.4, 1.5 Hz, 1H), 5.23 (dd, J=11.0, 1.5 Hz, 1H), 4.06 (dd, J=13.6, 6.6 Hz, 4H), 1.41 (t, J=7.0 Hz, 3H). $^{13}$C NMR (126 MHz, CDCl3) δ 156.4, 137.7, 137.0, 134.8, 130.4, 129.7, 129.1, 127.6, 127.0, 126.3, 125.4, 120.1, 115.1, 110.8, 63.4, 32.7, 14.8. HRMS (ESI) [M+Na]$^+$ for $C_{17}C_{18}O$ 261.1255. found 261.1257

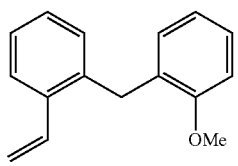 [SMILES: C=Cc1ccccc1Cc1ccccc1OC]

1-methoxy-2-(2-vinylbenzyl)benzene (9m). clear oil (197 mg, 86%) $^1$H NMR (400 MHz, Chloroform-d) δ 7.54 (dd, J=7.1, 1.9 Hz, 1H), 7.24-7.15 (m, 3H), 7.13-7.06 (m, 1H), 6.95 (dd, J=17.4, 11.0 Hz, 1H), 6.88 (d, J=8.2 Hz, 1H), 6.83 (d, J=4.6 Hz, 2H), 5.64 (dd, J=17.4, 1.4 Hz, 1H), 5.23 (dt, J=11.0, 1.2 Hz, 1H), 4.03 (s, 2H), 3.85 (d, J=1.0 Hz, 3H). $^{13}$C NMR (126 MHz, CDCl3) δ 157.5, 138.0, 137.5, 135.2, 130.8, 130.2, 129.3, 128.2, 127.6, 126.9, 126.0, 120.8, 115.7, 110.3, 55.7, 33.1. HRMS (ESI) [M+H]$^+$ for $C_{16}H_{17}O$ 225.1279. found 225.1280.

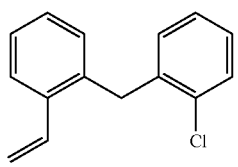 [SMILES: C=Cc1ccccc1Cc1ccccc1Cl]

1-chloro-2-(2-vinylbenzyl)benzene (9n). yellow oil (147 mg, 93%) $^1$H NMR (400 MHz, Chloroform-d) δ 7.56 (dd, J=7.5, 1.6 Hz, 1H), 7.40 (dd, J=7.5, 1.7 Hz, 1H), 7.30-7.20 (m, 2H), 7.14 (pd, J=7.4, 1.8 Hz, 2H), 7.05 (dd, J=7.5, 1.6 Hz, 1H), 6.91-6.81 (m, 2H), 5.65 (dd, J=17.3, 1.3 Hz, 1H), 5.26 (dd, J=11.0, 1.4 Hz, 1H), 4.15 (s, 2H). $^{13}$C NMR (126 MHz, CDCl3) δ 138.0, 137.1, 136.2, 134.3, 133.9, 130.3, 130.1, 129.2, 127.9, 127.4, 126.8, 126.7, 125.8, 115.9, 36.3. HRMS (ESI) [M]$^+$ for $C_{15}H_{13}Cl$ 228.0706. found 228.0712.

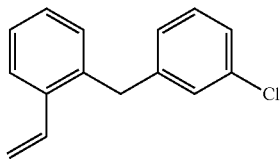 [SMILES: C=Cc1ccccc1Cc1cccc(Cl)c1]

1-(3-chlorobenzyl)-2-vinylbenzene (9o). yellow oil (78 mg, 79%) $^1$H NMR (400 MHz, Chloroform-d) δ 7 53 (dd, J=7.0, 2.1 Hz, 1H), 7.27-7.20 (m, 4H), 7.11 (dd, J=6.9, 2.1 Hz, 1H), 7.07-7.02 (m, 2H), 6.88 (dd, J=17.3, 10.9 Hz, 1H), 5.63 (dd, J=17.4, 1.4 Hz, 1H), 5.25 (dd, J=11.0, 1.3 Hz, 1H), 4.03 (s, 2H). 13C NMR (126 MHz, CDCl3) δ 142.6, 136.9, 136.7, 134.3, 134.1, 130.3, 129.5, 128.6, 127.9, 126.9, 126.7, 126.1, 126.0, 116.0, 38.5. HRMS (ESI) m/z [M]$^+$ for $C_{15}H_{13}Cl$ 228.0706. found 228.0697.

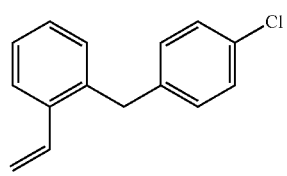 [SMILES: C=Cc1ccccc1Cc1ccc(Cl)cc1]

1-(4-chlorobenzyl)-2-vinylbenzene (9p). yellow oil (99 mg, 68%) $^1$H NMR (400 MHz, Chloroform-d) δ 7 54 (dd, J=7.0, 2.2 Hz, 1H), 7.30-7.23 (m, 2H), 7.24-7.15 (m, 2H), 7.13-7.10 (m, 2H), 7.02-6.97 (m, 1H), 6.89 (dd, J=17.3, 11.0 Hz, 1H), 5.64 (dd, J=17.3, 1.3 Hz, 1H), 5.27 (dd, J=11.0, 1.3 Hz, 1H), 4.04 (s, 2H). $^{13}$C NMR (126 MHz, CDCl3) δ 139.4, 137.6, 137.4, 134.8, 132.1, 130.8, 130.3 (2C), 128.9 (2C), 128.4, 127.4, 126.4, 116.5, 38.8. HRMS [M]$^+$ for $C_{15}H_{13}Cl$ 228.0706. found 228.0703.

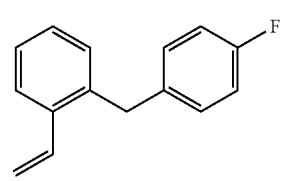 [SMILES: C=Cc1ccccc1Cc1ccc(F)cc1]

1-(4-fluorobenzyl)-2-vinylbenzene (9q). clear oil (291 mg, 92%) $^1$H NMR (400 MHz, Chloroform-d) δ 7.57-7.50 (m, 1H), 7.29-7.20 (m, 2H), 7.15-7.03 (m, 3H), 6.99-6.86 (m, 3H), 5.63 (dd, J=17.4, 1.4 Hz, 1H), 5.25 (dd, J=11.0, 1.4 Hz, 1H), 4.04 (s, 2H). $^{13}$C NMR (126 MHz, CDCl3) δ 138.0, 137.4, 136.6, 136.6, 134.9, 130.7, 130.4, 130.3, 128.4, 127.3, 126.4, 116.3, 115.7, 115.5, 38.6. HRMS (ESI) [M+H]$^+$ for $C_{15}H_{14}F$ 213.1080. found 213.1077.

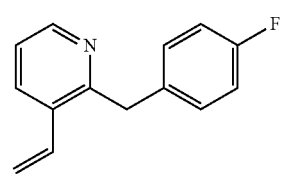 [SMILES: C=Cc1cccnc1Cc1ccc(F)cc1]

2-(4-fluorobenzyl)-3-vinylpyridine (9r). A microwave vial was charged with 14d (250 mg, 1.3 mmol, 1 eq.), 4-fluorobenzylboronicacid pinacol ester (317 mg, 1.3 mmol, 1 eq.), [1,1'-Bis(diphenylphosphino)ferrocene]dichloropalladium(II) (49 mg, 0.07 mmol, 0.05 eq.), and K$_3$PO$_4$ (560 mg, 4 mmol, 3 eq.) and capped with a Teflon lined lid. The vial was evacuated and purged with argon (3×) and then dioxane (15 mL) was added. The reaction mixture was heated to 90° C. for 14 h, cooled to rt, and diluted with EtOAc (40 mL) and water (15 mL). The aqueous layer was extracted with EtOAc (2×20 mL). The combined organic layers were dried, concentrated and purified via through a filter column (SiO$_2$, 1:2 EtOAc:Hexanes) and used as obtained. The residue was added to a stirred solution of n-butyl lithium (1.5 eq.) and methyltriphenylphosphonium bromide (1.3 eq.) at 0° C. The reaction was stirred for 8 h at rt and quenched with water (10 mL). The aqueous phase was extracted with EtOAc (2×15 mL). The combined organic layers were dried, concentrated, and purified via flash chromatography (SiO$_2$, 1:3 EtOAc:Hexanes) to provide 9r as a clear oil (73 mg, 26%).$^1$H NMR (400 MHz, Chloroform-d) δ 8.51-8.46 (m, 1H), 7.82-7.72 (m, 1H), 7.16 (ddd, J=15.5, 8.1, 5.1 Hz, 3H), 6.92 (dt, J=18.4, 9.7 Hz, 3H), 5.65 (d, J=17.3 Hz, 1H), 5.36 (d, J=11.0 Hz, 1H), 4.22 (s, 2H).$^{13}$C NMR (126 MHz, CDCl3) δ 162.8, 160.8, 157.5, 149.0, 135.3, 134.1, 133.4, 130.4, 130.3, 122.5, 118.3, 115.7, 115.5, 41.3. HRMS (ESI) [M+H]$^+$ for C$_{14}$H$_{13}$FN 214.1032. found 214.1036.

General Procedure for the Synthesis of 6-7

A microwave vial was charged with 8 (200 mg, 2 eq.), 9a-9r (1 eq.), and palladium (II) acetate (5 mg, 0.1 eq.). The tube was sealed with a Teflon lined lid, evacuated and purged with argon (3×). Triethanolamine (0.8 mL) was added and the reaction was stirred at 115° C. for 12 h. The reaction was cooled, partitioned between Et$_2$O (30 mL) and water (10 mL). The aqueous layer was extracted with Et$_2$O (3×20 mL). The organic layers were combined, dried, and concentrated. The residue was passed through a filter column (SiO$_2$, 1:1 EtOAc:Hexanes) and concentrated. The residue was dissolved in EtOAc (15 mL), evacuated and purged with argon (3×) before the addition of 10% Pd/C (25 mg). The reaction was then stirred under a hydrogen atmosphere (balloon) for 14 h. The reaction mixture was passed through a pad of celite and washed with DCM and concentrated. The residue was purified by flash chromatography (SiO$_2$, 1:2 EtOAc:Hexanes) to provide the desired compounds 6-7 and 16-31.

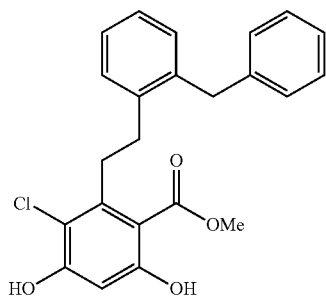 [SMILES: COC(=O)c1c(O)cc(O)c(Cl)c1CCc1ccccc1Cc1ccccc1]

methyl 2-(2-benzylphenethyl)-3-chloro-4,6-dihydroxybenzoate (6). White amorphous solid (45 mg, 52%).$^1$H NMR (400 MHz, Chloroform-d) δ 11.40 (s, 11H), 7.31-7.22 (m, 2H), 7.20 (q, J=4.5, 2.8 Hz, 4H), 7.11 (d, J=7.6 Hz, 3H), 6.58 (s, 1H), 6.05 (s, 1H), 4.11 (s, 2H), 3.91 (d. J=1.0 Hz, 3H), 3.42-3.34 (m, 2H), 2.91-2.80 (m, 2H).$^{13}$C NMR (126 MHz, CDCl3) δ 170.8, 163.1, 156.0, 142.6, 140.6, 139.7, 138.3, 130.4, 129.0, 128.6, 128.3, 126.6, 126.4, 125.9, 113.7, 106.6, 102.5, 52.5, 38.3, 33.9, 32.3. HRMS (ESI) [M]$^-$ for C$_{23}$H$_{21}$ClO$_4$ 396.1128. found 396.1122.

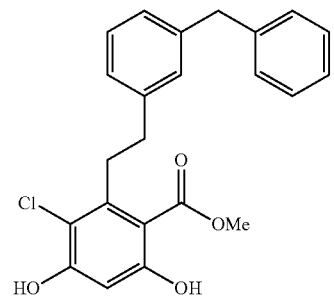 [SMILES: COC(=O)c1c(O)cc(O)c(Cl)c1CCc1cccc(Cc2ccccc2)c1]

methyl 2-(3-benzylphenethyl)-3-chloro-4,6-dihydroxybenzoate (7). White amorphous solid (57 mg, 66%)$^1$H NMR (400 MHz, Chloroform-d) δ 11.45 (s, 1H), 7.36-7.26 (m, 3H), 7.22 (t, J=7.5 Hz, 3H), 7.09 (t, J=8.1 Hz, 2H), 7.03 (s, 1H), 6.57 (s, 1H), 6.06 (s, 1H), 4.00 (s, 2H), 3.83 (s, 3H), 3.38-3.30 (m, 2H), 2.87-2.70 (m, 2H).$^{13}$C NMR (126 MHz, CDCl3) δ 170.9, 163.1, 156.1, 142.6, 141.7, 141.3, 140.9, 128.9 (2C), 128.7, 128.5, 128.4 (2C), 126.7, 126.0, 125.9, 113.6, 106.5, 102.4, 52.3, 41.8, 35.4, 35.0. HRMS (ESI) [M+H]$^+$ for C$_{23}$H$_{22}$ClO$_4$ 397.1207. found 397.1230.

Both 9c and 9d were synthesized using similar conditions to 9a and 9b outlined in Scheme 1. As shown in Scheme 2, the appropriate commercially available aryl bromides, 14a-d and 15a-c, were subjected to a palladium-cross coupling reaction with potassium benzyltrifluoroborate. RuPhos, and palladium (II) acetate to provide benzaldehydes 13e-k. Conversion of benzaldehydes 13e-k to the corresponding styrenes, 9c-k, was achieved via a Wittig reaction with methyltriphenylphosphonium bromide and n-butyllithium. The corresponding alkenes were then subjected to a Heck reaction with 8, followed by simultaneous cleavage of the benzyl ethers and reduction of the alkene to provide compounds 16-24. Under hydrogenation conditions, the nitro group was also reduced to the corresponding aniline (19 and 20) and hydrogenolysis of the benzyl ethers produced the free phenols, 22-24.

General Procedure for the Synthesis of 16-31

16-31 were prepared according to the general synthetic procedure for the synthesis of 6-7. In particular, synthesis of 31 was accomplished as shown below in Scheme 3 via a palladium-catalyzed cross coupling reaction between 14d and 4-fluorobenzylboronic acid pinacol ester (32) to provide benzaldehyde 13r which was then converted to the corresponding styrene 9r. A Heck coupling reaction between 9r and 8 followed by hydrogenolysis of the benzyl ethers and reduction of the alkene provided 31.

Scheme 3: Synthesis of 25-31

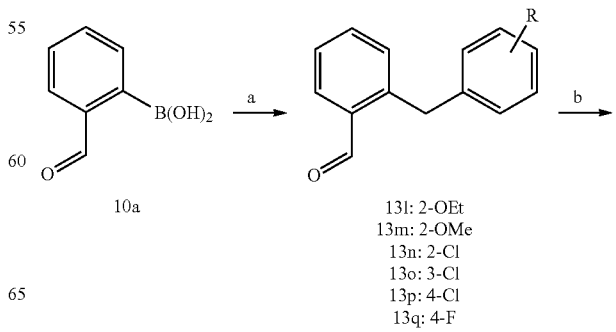

13l: 2-OEt
13m: 2-OMe
13n: 2-Cl
13o: 3-Cl
13p: 4-Cl
13q: 4-F

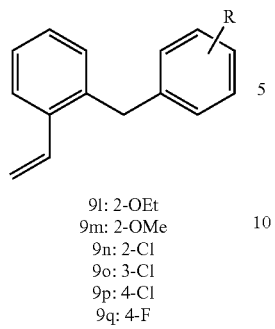

9l: 2-OEt
9m: 2-OMe
9n: 2-Cl
9o: 3-Cl
9p: 4-Cl
9q: 4-F

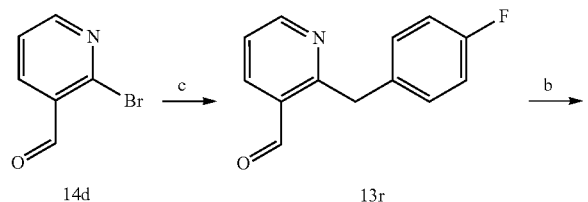

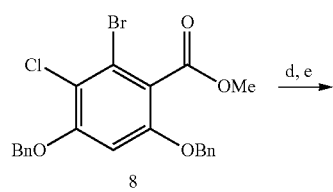

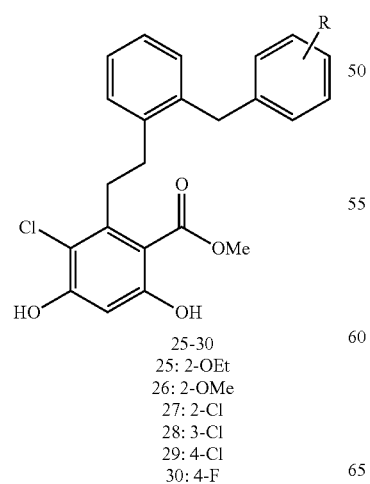

25-30
25: 2-OEt
26: 2-OMe
27: 2-Cl
28: 3-Cl
29: 4-Cl
30: 4-F

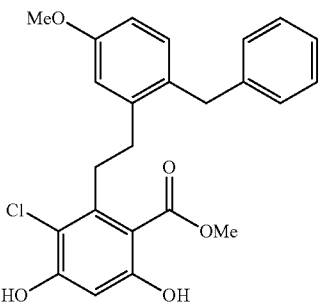 [SMILES: COC(=O)c1c(O)cc(O)c(Cl)c1CCc1cc(OC)ccc1Cc1ccccc1]

Conditions: (a) Pd(PPh$_3$)$_4$, K$_2$CO$_3$, benzyl bromides; (b) MePh$_3$P$^+$Br$^-$, $^n$BuLi; (c) Pd(dppf)Cl$_2$, K$_3$PO$_4$, 4-fluorobenzylboronic acid pinacol ester (32); (d) Pd(OAc)$_2$, 9l-9r, triethanolamine; (e) H$_2$, Pd/C

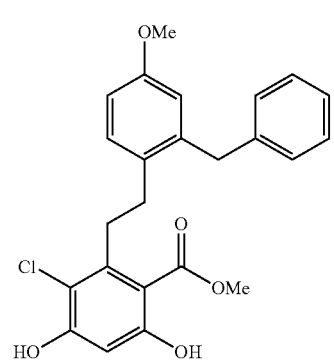 [SMILES: COC(=O)c1c(O)cc(O)c(Cl)c1CCc1ccc(OC)cc1Cc1ccccc1]

methyl 2-(2-benzyl-S-methoxyphenethyl)-3-chloro-4,6-dihydroxybenzoate (16). White amorphous solid (25 mg, 27%) $^1$H NMR (400 MHz, Chloroform-d) δ 11.40 (s, 1H). 7.24 (s. 2H), 7.17 (t, J=7.2 Hz, 1H), 7.09 (d, J=7.6 Hz, 2H), 7.03 (d, J=8.4 Hz, 1H), 6.84 (d, J=2.7 Hz, 11H), 6.74 (dd, J=8.3, 2.7 Hz, 1H), 6.57 (s, 1H), 6.05 (s, 1H), 4.04 (s, 2H), 3.91 (d, J=1.0 Hz, 3H), 3.81 (s, 3H), 3.41-3.33 (m, 2H), 2.85-2.74 (m, 2H).$^{13}$C NMR (126 MHz, CDCl3) δ 171.3, 163.5, 158.6, 156.5, 143.1, 141.5, 141.5, 131.9, 131.1, 129.0 (2C), 128.8 (2C), 126.3, 115.6, 114.2, 111.5, 107.1, 103.0, 55.6, 53.0, 38.1, 34.23, 33.0. HRMS (ESI) [M+Na]$^+$ for C$_{24}$H$_{23}$ClO$_5$Na 449.1132. found 449.1126.

methyl 2-(2-benzyl-4-methoxyphenethyl)-3-chloro-4,6-dihydroxybenzoate (17). White amorphous solid (83 mg, 90%) $^1$H NMR (400 MHz, Chloroform-d) δ 11.40 (s, 1H), 7.26 (d, J=1.2 Hz, 1H), 7.19 (d, J=8.2 Hz, 2H), 7.12 (d, J=7.5 Hz, 2H), 6.78 (d, J=8.5 Hz, 1H), 6.66 (s, 1H), 6.57 (s, 1H), 6.04 (s, 1H), 4.08 (s, 2H), 3.91 (s, 3H), 3.76 (s, 3H), 3.39-3.32 (m, 2H), 2.81 (d, J=8.7 Hz, 2H).$^{13}$C NMR (126 MHz, CDCl3) δ 163.5, 158.5, 156.5, 143.2, 140.9, 140.1, 132.4, 130.5, 129.1 (2C), 128.9 (2C), 126.5, 116.5 (2C), 114.2, 112.2, 107.1, 103.0, 55.6, 53.0, 39.0, 34.7, 32.2. HRMS (ESI) [M+Na]+ for $C_{24}H_{23}ClO_5$ 449.1132. found 449.1128.

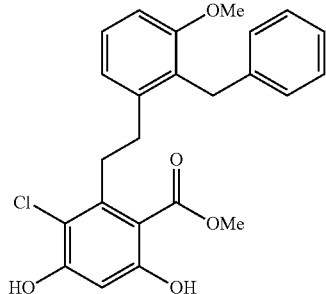 [SMILES: COC(=O)c1c(O)cc(O)c(Cl)c1CCc1cccc(OC)c1Cc1ccccc1]

methyl 2-(2-benzyl-3-methoxyphenethyl)-3-chloro-4,6-dihydroxybenzoate (18). White amorphous solid (57 mg, 64%)$^1$H NMR (400 MHz, Chloroform-d) δ 11.43 (d, J=11.6 Hz, 1H), 7.25-7.18 (m, 2H), 7.15-7.11 (m, 1H), 7.08 (d, J=7.6 Hz, 2H), 6.93 (d, J=7.6 Hz, 1H), 6.88-6.77 (m, 2H), 6.56 (d, J=1.1 Hz, 1H), 4.18 (s, 2H), 3.89 (s, 3H), 3.78 (s, 3H), 3.39-3.28 (m, 2H), 2.85 (dd, J=10.7, 6.0 Hz, 2H).$^{13}$C NMR (126 MHz, CDCl3) δ 171.3, 163.5, 156.5, 142.9, 134.1, 131.0, 130.7, 128.4, 127.6, 127.6, 127.1, 125.4, 124.5, 123.5, 114.3, 111.7, 111.3, 107.2, 103.0, 69.9, 56.65, 52.5, 35.0, 33.1. HRMS (ESI) [M]+ for $C_{24}H_{23}ClO_5$ 426.1234. found 426.1234.

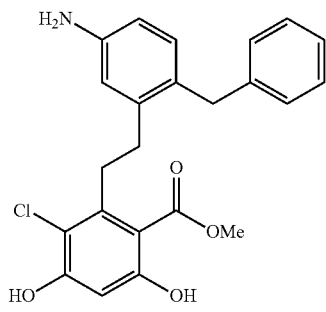 [SMILES: COC(=O)c1c(O)cc(O)c(Cl)c1CCc1cc(N)ccc1Cc1ccccc1]

methyl 2-(S-amino-2-benzylphenethyl)-3-chloro-4,6-dihydroxybenzoate (19). Tan amorphous solid (41 mg, 46%).$^1$H NMR (400 MHz, Chloroform-d) δ 11.40 (s, 1H), 7.31-7.25 (m, 2H), 7.23-7.17 (m, 1H), 7.15-7.10 (m, 3H), 6.71 (dd, J=8.2, 2.8 Hz, 1H), 6.57 (s, 1H), 6.54 (d, J=2.7 Hz, 1H), 6.07 (s, 1H), 4.05 (s, 2H), 3.91 (s, 3H), 3.41-3.30 (m, 2H), 2.84-2.73 (m, 2H).$^{13}$C NMR (126 MHz, CDCl3) δ 170.8, 163.0, 156.0, 153.8, 142.7, 140.2, 140.0, 131.9, 130.2, 128.7 (2C), 128.4 (2C), 126.0, 116.9, 113.4, 106.6, 102.5, 52.5, 38.3, 34.1, 31.7. HRMS (ESI) [M+H]+ for $C_{23}H_{23}ClNO_4$ 412.1316. found 412.1303.

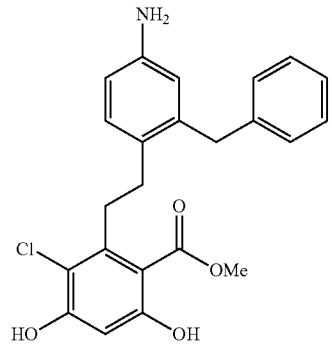 [SMILES: COC(=O)c1c(O)cc(O)c(Cl)c1CCc1ccc(N)cc1Cc1ccccc1]

methyl 2-(4-amino-2-benzylphenethyl)-3-chloro-4,6-dihydroxybenzoate (20). Tan amorphous solid (38 mg, 43%).$^1$H NMR (400 MHz, Chloroform-d) δ 7.25-7.19 (m, 2H), 7.17-7.13 (m, 1H), 7.09 (d, J=7.7 Hz, 2H), 7.05 (d, J=7.9 Hz, 1H), 6.56 (dd, J=8.2, 2.5 Hz, 1H), 6.41 (dd, J=4.9, 1.9 Hz, 2H), 4.00 (s, 2H), 3.86 (s, 3H), 3.34-3.22 (m, 2H), 2.75-2.67 (m, 2H), 2.63 (br s, 2H).$^{13}$C NMR (126 MHz, CDCl3) δ 171.5, 162.6, 157.9, 144.6, 143.6, 141.2, 139.8, 130.9, 130.4, 129.1, 129.1, 128.7, 128.7, 126.2, 117.7, 114.9, 114.2, 106.3, 102.4, 52.7, 38.7, 34.6, 32.1. HRMS (ESI) [M+H]+ for $C_{23}H_{23}ClNO_4$ 412.1316. found 412.1302.

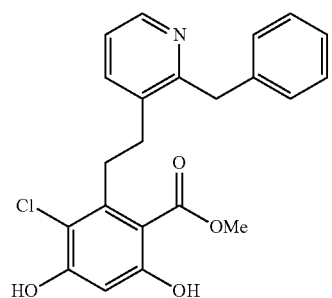 [SMILES: COC(=O)c1c(O)cc(O)c(Cl)c1CCc1cccnc1Cc1ccccc1]

methyl 2-(2-(2-benzylpyridin-3-yl)ethyl)-3-chloro-4,6-dihydroxybenzoate (21). White amorphous solid (81 mg, 94%).$^1$H NMR (400 MHz, Chloroform-d) δ 11.34 (s, 1H), 8.49 (d, J=4.9 Hz. 11H), 7.51 (d, J=7.7 Hz, 1H), 7.23 (d, J=7.2 Hz, 2H), 7.19-7.13 (m, 4H), 6.58 (d, J=1.1 Hz, 1H), 6.40 (s, 1H), 4.30 (s, 2H), 3.86 (d, J=1.0 Hz, 3H), 3.50-3.35 (m, 2H), 3.04-2.83 (m, 2H).$^{13}$C NMR (126 MHz, CDCl3) δ 170.8, 163.3, 158.5, 156.5, 147.5, 142.2, 139.5, 137.1, 135.1, 128.7 (2C), 128.6 (2C), 126.4, 122.1, 114.1, 106.7, 103.0, 52.7, 41.3, 33.4, 31.8. HRMS (ESI) [M+H]+ for $C_{22}H_{21}ClNO_4$ 398.1159. found 398.1154.

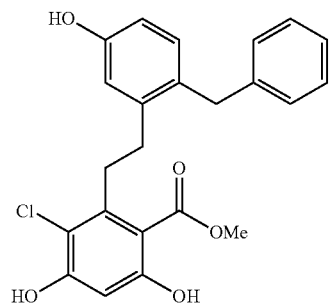 [SMILES: COC(=O)c1c(O)cc(O)c(Cl)c1CCc1cc(O)ccc1Cc1ccccc1]

methyl 2-(2-benzyl-5-hydroxyphenethyl)-3-chloro-4,6-dihydroxybenzoate (22). White amorphous solid (42 mg, 47%). $^1$H NMR (400 MHz, Chloroform-d) δ 11.37 (s, 1H), 7.24 (s, 2H), 7.18 (d, J=7.3 Hz, 1H), 7.09 (d, J=7.5 Hz, 2H), 6.97 (d, J=8.2 Hz, 1H), 6.79 (d, J=2.4 Hz, 1H), 6.66 (d, J=8.4 Hz, 1H), 6.58 (s, 1H), 6.04 (s, 1H), 4.02 (s, 2H), 3.90 (s, 3H), 3.40-3.32 (m, 2H), 2.86-2.73 (m, 2H). $^{13}$C NMR (126 MHz, CDCl3) δ 171.2, 163.5, 156.5, 154.5, 143.0, 141.8, 141.5, 132.0, 131.2, 129.0 (2C), 128.8 (2C), 126.4, 116.2, 113.7, 107.1, 103.0, 53.0, 38.1, 34.1, 32.8. HRMS (ESI) [M+H]$^+$ for $C_{23}H_{22}ClO_5$ 413.1156. found 413.1150.

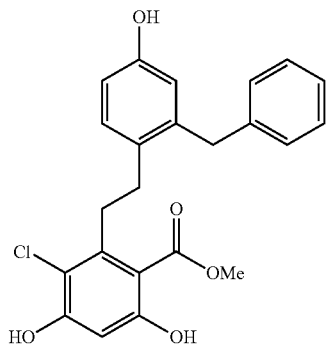 [SMILES: COC(=O)c1c(O)cc(O)c(Cl)c1CCc1ccc(O)cc1Cc1ccccc1]

methyl 2-(2-benzyl-4-hydroxyphenethyl)-3-chloro-4,6-dihydroxybenzoate (23). White amorphous solid (38 mg, 42%). $^1$H NMR (400 MHz, Chloroform-d) δ 11.40 (s, 1H), 7.27 (d. J=8.4 Hz, 2H), 7.22-7.17 (m, 1H), 7.16-7.11 (m, 3H), 6.71 (dd, J=8.2, 2.8 Hz, 1H), 6.57 (s, 1H), 6.54 (d, J=2.7 Hz, 1H), 6.07 (s, 1H), 4.05 (s, 2H), 3.91 (s, 3H), 3.40-3.32 (m, 2H), 2.87-2.73 (m, 2H). $^{13}$C NMR (126 MHz, CDCl3) δ 171.3, 163.5, 156.5, 154.4, 143.2, 140.7, 140.5, 132.4, 130.7, 129.2 (2C), 128.9 (2C), 126.6, 117.4, 113.9, 107.1, 103.0, 53.0, 38.8, 34.6, 32.2. HRMS (ESI) [M+H]$^+$ for $C_{23}H_{22}ClO_5$ 413.1156. found 413.1175.

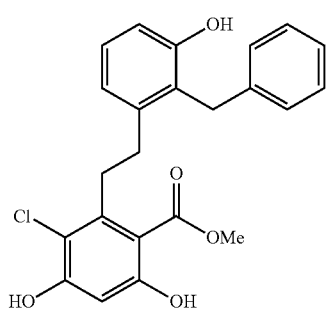 [SMILES: COC(=O)c1c(O)cc(O)c(Cl)c1CCc1cccc(O)c1Cc1ccccc1]

methyl 2-(2-benzyl-3-hydroxyphenethyl)-3-chloro-4,6-dihydroxybenzoate (24). White amorphous solid (25 mg, 28%) $^1$H NMR (400 MHz, Chloroform-d) δ 11.40 (s, 1H), 7.24 (d, J=0.9 Hz, 2H), 7.18 (d, J=7.9 Hz, 1H), 7.14 (dd, J=7.9, 1.5 Hz, 3H), 6.95-6.91 (m, 1H), 6.74 (d, J=1.2 Hz, 1H), 6.56 (s, 1H), 6.03 (s, 1H), 4.62 (s, 1H), 4.19 (s, 2H), 3.89 (s, 3H), 3.39-3.26 (m, 2H), 2.93-2.79 (m, 2H). $^{13}$C NMR (126 MHz, CDCl3) δ 171.1, 163.3, 156.3, 154.4, 142.8, 142.0, 139.9, 128.8 (2C), 128.1 (2C), 127.7, 126.4, 124.9, 122.0, 114.0, 114.0, 106.8, 102.8, 52.7, 34.4, 33.0, 31.5. HRMS (ESI) [M]$^+$ for $C_{23}H_{21}ClO_5$ 412.1078. found 412.1073.

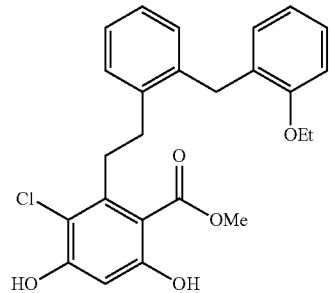 [SMILES: CCOc1ccccc1Cc1ccccc1CCc1c(Cl)c(O)cc(O)c1C(=O)OC]

methyl 3-chloro-2-(2-(2-ethoxybenzyl)phenethyl)-4,6-dihydroxybenzoate (25). Tan amorphous solid (61 mg, 64%). $^1$H NMR (400 MHz, Chloroform-d) δ 11.46 (s, 1H), 7.29 (dd, J=7.6, 1.6 Hz, 2H), 7.22 (td, J=7.4, 1.6 Hz, 1H), 7.17 (td, J=7.7, 2.2 Hz, 2H), 7.09 (dd, J=7.5, 1.5 Hz, 1H). 6.90-6.80 (m, 3H), 6.57 (s, 1H), 6.04 (d, J=1.2 Hz, 1H), 4.09 (s, 2H), 4.03 (q, J=7.0 Hz, 2H), 3.93 (s, 3H), 3.40-3.30 (m, 2H), 2.94-2.72 (m, 2H), 1.35 (t, J=7.0 Hz, 3H). $^{13}$C NMR (126 MHz, CDCl3) δ 171.0, 163.1, 156.5, 156.0, 142.9, 139.9, 138.3, 130.2, 129.6, 129.2, 128.9, 127.1, 126.3, 126.3, 120.1, 113.8, 110.7, 106.5, 102.4, 63.3, 52.5, 34.0, 32.5, 32.4, 14.8. HRMS (ESI) [M+H]$^+$ for $C_{25}H_{26}ClO_5$ 441.1469. found 441.1449.

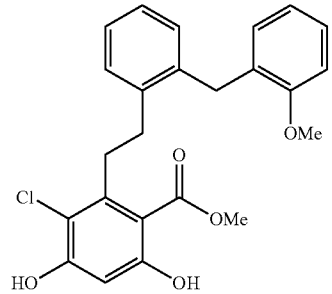 [SMILES: COC(=O)c1c(O)cc(O)c(Cl)c1CCc1ccccc1Cc1ccccc1OC]

methyl 3-chloro-4,6-dihydroxy-2-(2-(2-methoxybenzyl)phenethyl)benzoate (26). White amorphous solid (52 mg, 56%). $^1$H NMR (400 MHz, Chloroform-d) δ 11.50 (s, 11H), 7.31 (d, J=7.5 Hz, 1H), 7.25 (d, J=6.0 Hz, 1H), 7.20 (q, J=8.3, 7.3 Hz, 2H), 7.09 (d, J=7.5 Hz, 1H), 6.89 (d, J=8.2 Hz, 1H), 6.86-6.81 (m, 2H), 6.58 (s, 1H), 6.12 (s, 1H), 4.10 (s, 2H), 3.95 (s, 3H), 3.83 (s, 3H), 3.45-3.29 (m, 2H), 2.97-2.69 (m, 2H). $^{13}$C NMR (126 MHz, CDCl3) δ 171.5, 163.5, 157.6, 156.6, 143.3, 140.4, 138.6, 130.7, 130.0, 129.6, 129.5, 127.7, 126.8, 126.8, 120.8, 114.3, 110.3, 107.0, 102.9, 55.6, 52.9, 34.5, 32.9, 32.7. HRMS (ESI) [M-Na]$^+$ for $C_{24}H_{23}ClO_5$ 449.1132. found 449.1124.

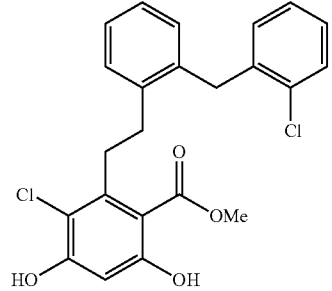 [SMILES: COC(=O)c1c(O)cc(O)c(Cl)c1CCc1ccccc1Cc1ccccc1Cl]

methyl 3-chloro-2-(2-(2-chlorobenzyl)phenethyl)-4,6-dihydroxybenzoate (27). Clear oil (27 mg, 29%). $^1$H NMR (400 MHz, Chloroform-d) δ 11.41 (s, 1H), 7.40 (dd, J=7.6, 1.7 Hz, 1H), 7.33 (dd, J=7.6, 1.6 Hz, 1H), 7.30-7.24 (m, 1H), 7.22-7.09 (m, 3H), 7.01 (dd, J=7.6, 1.3 Hz, 1H), 6.88-6.80 (m, 1H), 6.57 (s, 1H), 6.06 (s, 1H), 4.20 (s, 2H), 3.96 (s, 3H), 3.41-3.30 (m, 2H), 2.91-2.72 (m, 2H). $^{13}$C NMR (126 MHz, CDCl3) δ 170.8, 163.0, 156.1, 142.5, 140.0, 138.3, 136.7, 134.1, 130.1, 130.1, 129.2, 129.2, 127.5, 126.8, 126.7, 126.6, 113.8, 106.5, 102.5, 52.5, 36.0, 334.0, 32.4. HRMS (ESI) [M+H]+ for $C_{23}H_{21}Cl_2O_4$ 431.0817. found 431.0836

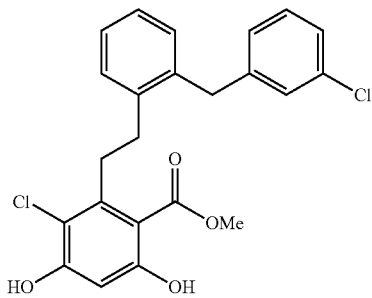 [SMILES: COC(=O)c1c(O)cc(O)c(Cl)c1CCc1ccccc1Cc1cccc(Cl)c1]

methyl 3-chloro-2-(2-(3-chlorobenzyl)phenethyl)-4,6-dihydroxybenzoate (28). Clear oil (35 mg, 37%). $^1$H NMR (400 MHz, Chloroform-d) δ 11.38 (s, 1H), 7.28 (dd, J=3.0, 1.8 Hz, 1H), 7.25-7.21 (m, 1H), 7.20-7.16 (m, 2H), 7.10 (dd, J=7.4, 1.5 Hz, 1H), 7.07 (dt, J=1.8, 1.0 Hz, 1H), 7.02-6.97 (m, 1H), 6.58 (s, 1H), 6.08 (d, J=5.2 Hz, 2H), 4.08 (s, 2H), 3.93 (s, 3H), 3.43-3.31 (m, 2H), 2.91-2.74 (m, 2H). $^{13}$C NMR (126 MHz, CDCl3) δ 170.7, 163.0, 156.1, 142.7, 142.5, 139.6, 137.4, 134.2, 130.5, 129.6, 129.1, 128.6, 126.9, 126.7, 126.6, 126.2, 113.7, 106.6, 102.6, 52.5, 38.0, 33.8, 32.3. HRMS (ESI) [M+H]+ for $C_{23}H_{20}Cl_2O_4$ 431.0817. found 431.0835.

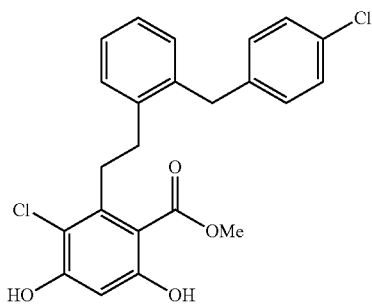 [SMILES: COC(=O)c1c(O)cc(O)c(Cl)c1CCc1ccccc1Cc1ccc(Cl)cc1]

methyl 3-chloro-2-(2-(4-chlorobenzyl)phenethyl)-4,6-dihydroxybenzoate (29). Clear oil (25 mg, 27%) $^1$H NMR (400 MHz, Chloroform-d) δ 11.37 (s, 1H), 7.30-7.26 (m, 2H), 7.23 (d, J=8.4 Hz, 2H), 7.21-7.16 (m, 1H), 7.16-7.07 (m, 2H), 7.07-7.00 (m, 2H), 6.58 (s, 1H), 6.07 (s, 1H), 4.07 (s, 2H), 3.92 (s, 3H), 3.44-3.34 (m, 2H), 2.90-2.76 (m, 2H). $^{13}$C NMR (126 MHz, CDCl3) δ 170.7, 163.0, 156.0, 142.5, 139.6, 139.1, 137.8, 130.4, 129.8, 129.1, 129.0, 128.6, 128.4, 128.3, 126.8, 126.5, 125.9, 106.6, 102.6, 52.5, 37.7, 33.9, 32.3. HRMS (ESI) [M+H]+ for $C_{23}H_{21}Cl_2O_4$ 431.0817. found 431.0814.

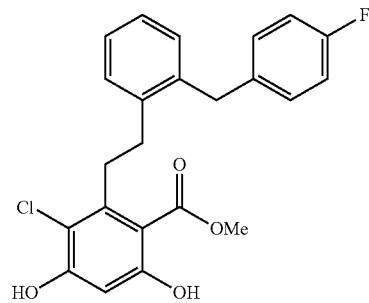 [SMILES: COC(=O)c1c(O)cc(O)c(Cl)c1CCc1ccccc1Cc1ccc(F)cc1]

methyl 3-chloro-2-(2-(4-fluorobenzyl)phenethyl)-4,6-dihydroxybenzoate (30). White amorphous solid (44 mg, 49%). $^1$H NMR (400 MHz, Chloroform-d) δ 11.38 (s, 1H), 7.29 (dd, J=7.5, 1.9 Hz, 1H), 7.24-7.16 (m, 2H), 7.13-7.02 (m, 3H), 6.99-6.92 (m, 2H), 6.58 (s, 1H), 6.07 (s, 1H), 4.07 (s, 2H), 3.92 (s, 3H), 3.41-3.35 (m, 2H), 2.90-2.78 (m, 2H). $^{13}$C NMR (126 MHz, CDCl3) δ 170.7, 163.0, 162.2 (d, J=244.0 Hz), 156.0, 142.5, 139.6, 138.2, 136.2, 136.2, 130.3, 129.9, 129.1, 126.7, 126.5, 115.2, 115.0, 113.7, 106.6, 102.5, 52.5, 37.5, 33.8, 32.3. HRMS (ESI) [M+H]+ for $C_{23}H_{21}ClFO_4$ 415.1112. found 415.1103.

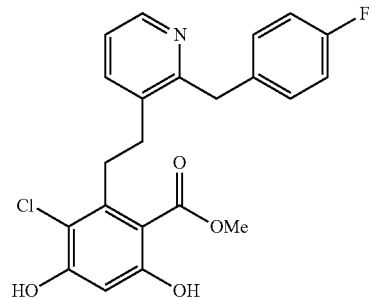 [SMILES: COC(=O)c1c(O)cc(O)c(Cl)c1CCc1cccnc1Cc1ccc(F)cc1]

methyl 3-chloro-2-(2-(2-(4-fluorobenzyl)pyridin-3-yl)ethyl)-4,6-dihydroxybenzoate (31). Clear oil (37 mg, 41%). $^1$H NMR (400 MHz, Chloroform-d) δ 8.42 (t, J=4.2 Hz, 1H), 7.54 (dd, J=7.6, 1.6 Hz, 1H), 7.17 (dd, J=7.7, 4.9 Hz, 1H), 7.09 (t, J=6.6 Hz, 2H), 6.90 (td, J=8.6, 2.0 Hz, 2H), 6.47 (d, J=3.9 Hz, 1H), 4.24 (s, 2H), 3.86 (s, 3H), 3.42-3.29 (m, 2H), 2.92-2.77 (m, 2H). $^{13}$C NMR (126 MHz, CDCl3) δ 170.6, 163.2, 162.6 (d, J=244 Hz), 156.7, 142.0, 130.1 (2C), 130.1 (2C), 122.3, 115.5 (2C), 115.4 (2C), 114.2, 106.7, 103.1 (2C), 52.7, 33.4, 31.7, 29.9. HRMS (ESI) [M+H]+ for $C_{22}H_{20}ClFNO_4$ 416.1065. found 416.1050.

General Procedure for the Synthesis of Diaryl Ether Compounds

A general procedure for the synthesis of diaryl ether compounds of the present technology is provided in Scheme 4 below and is notably similar to generation of other compounds of the present technology. See also Rao, H.; Ma, X.; Liu, Q.; Li, X.; Cao, S.; Li, C. Metal-free oxidative coupling: xanthone formation via direct annulation of 2-aryloxybenzaldehyde using tetrabutylammonium bromide as a promoter in aqueous medium *Adv. Syn & Cat.* 2013, 355, 2191-2196, incorporated herein by reference.

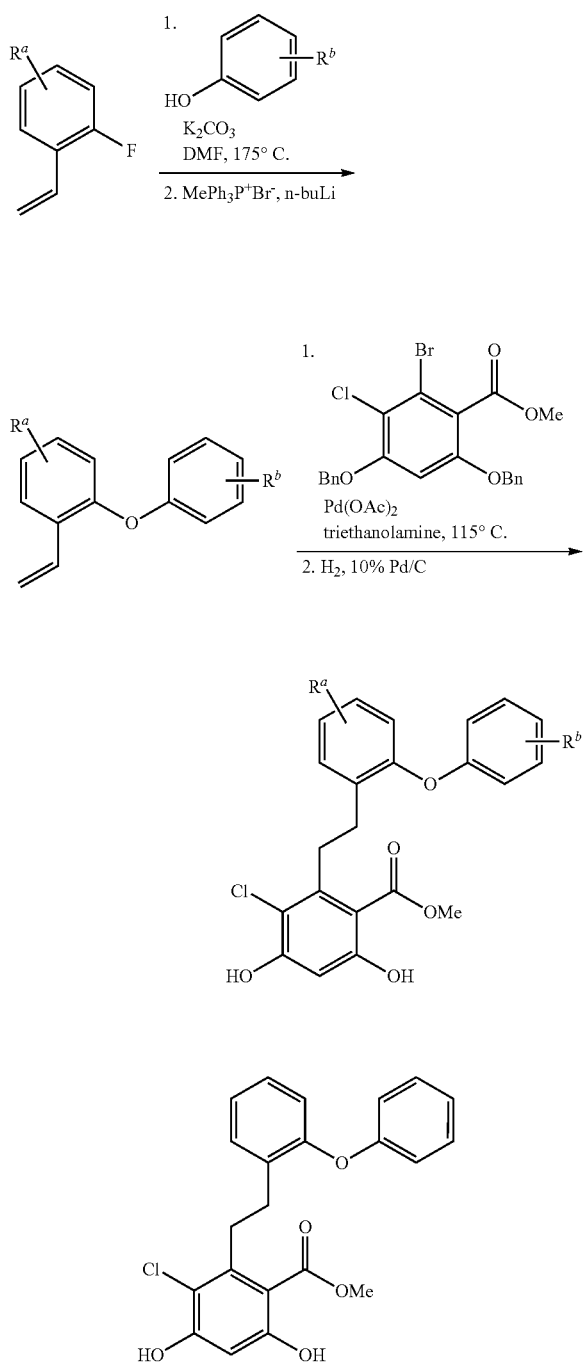

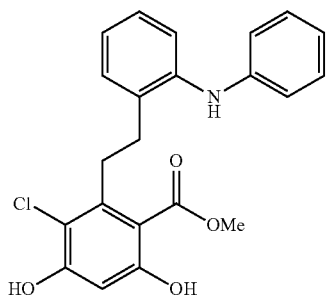 [SMILES: COC(=O)c1c(O)cc(O)c(Cl)c1CCc1ccccc1Nc1ccccc1]

methyl 3-chloro-4,6-dihydroxy-2-(2-phenoxyphenethyl)benzoate (33). White amorphous solid, 65 mg (38%). $^1$H NMR (400 MHz, Chloroform-d) δ 11.43 (s, 1H), 7.35-7.28 (m, 3H), 7.20 (td, J=7.7, 1.8 Hz, 1H), 7.12 (dd, J=7.4, 1.3 Hz, 1H), 7.07 (ddt, J=8.6, 7.3, 1.3 Hz, 1H), 6.97-6.93 (m, 2H), 6.90 (dd, J=8.1, 1.3 Hz, 1H), 6.55 (s, 1H), 6.04 (s, 1H), 3.89 (s, 3H), 3.51-3.38 (m, 2H), 2.98-2.87 (m, 2H). $^{13}$C NMR (126 MHz, CDCl3) δ 171.1, 163.1, 157.9, 156.1, 154.7, 142.8, 133.0, 130.6, 129.8 (2C), 127.7, 123.9, 122.8, 119.5, 117.9 (2C), 114.0, 106.8, 102.5, 52.5, 33.8, 30.0.

methyl 3-chloro-4,6-dihydroxy-2-(2-(phenylamino)phenethyl)benzoate (34). Compound 34 was prepared via analogous protocols to those described herein for other compounds. Yellow oil, 66 mg (38%). $^1$H NMR (400 MHz, Chloroform-d) δ 10.92 (s, 1H), 7.33 (dd, J=8.0, 1.2 Hz, 1H), 7.29-7.26 (m, 1H), 7.25-7.22 (m, 2H), 7.19 (td, J=7.7, 1.7 Hz, 1H), 7.02-6.96 (m, 3H), 6.89 (ddt, J=8.4, 7.2, 1.6 Hz, 1H), 6.58 (s, 1H), 6.09 (s, 1H), 5.92 (s, 1H), 3.96 (s, 3H), 3.45-3.33 (m, 2H), 2.95-2.75 (m, 2H). $^{13}$C NMR (126 MHz, CDCl3) δ 169.9, 162.5, 156.2, 144.2, 142.8, 140.9, 131.5, 130.2, 129.3 (2C), 127.3, 122.1, 120.4, 119.5, 117.1 (2C), 106.9, 103.0, 102.8, 52.6, 33.3, 31.4.

Example 2: Affinity and Selectivity Studies

Experimental Procedures

Fluorescence Polarization. The assay was performed in 96-well black, flat-bottom plates with a final volume of 100 μL. 25 μL of assay buffer (20 mM HEPES, pH 7.3, 50 mM KCl, 5 mM $MgCl_2$, 20 mM $Na_2MoO_4$, 2 mM DTT, 0.1 mg/mL BGG, and 0.01% NP-40) were added, followed by 25 μL of assay buffer containing 6 nM FITC-GDA (fluorescent tracer, stock in DMSO, diluted in assay buffer) and 50 μL of assay buffer containing 10 nM of either Grp94 or Hsp90α were added to each well. For each plate, wells containing buffer only (background), tracer in buffer only (low polarization control) and protein, tracer, and 1% DMSO (final concentration, high polarization control) were included. Compounds were then added with a final concentration of DMSO=1%. Plates were incubated at 4° C. with rocking for 24 h. Polarization values (in mP units) were measured at 37° C. with an excitation filter at 485 nm and an emission filter at 528 nm. Polarization values were correlated to % tracer bound and compound concentrations. The concentration at which the tracer was 50% displaced by compound of interested were calculated and reported as apparent Kd's.

Cell Culture. MDA-MB-231, PC3-MM2, SK-MEL-28, and A549 cells were grown in a water jacketed incubator at 37° C. with 5% $CO_2$ in DMEM (MDA-MB-231 and PC3-MM2), EMEM (SK-MEL-28) or F-12K (A549) media supplemented with 10% FBS and 1% penicillin/streptomycin.

Anti-proliferation. cells were counted via Trypan blue exclusion and seeded in 96-well plates at 2000 cells/0.1 mL/well then returned to the incubator for 24 h. Compounds or vehicle were administered in DMSO (1% DMSO final concentration) and the plates were placed back in the incubator. After 72 h, the % viable cells were determined using the MTS/PMS cell proliferation kit (Promega) per the manufacturer's instructions. Cells treated with vehicle were normalized to 100% viable and compound treated wells were adjusted accordingly. $GI_{50}$ values were calculated via GraphPad Prism and reported as the average of 2 or more independent experiments f SEM.

Wound Healing Scratch Assay. Cells were counted via Trypan blue exclusion and seeded in 12-well plates at 200,000 cells/mL/well and returned to the incubator for 24 h. Scratches were made with a 0.1-10 µL pipette tip, then cells were washed with PBS and fresh media was added. Compound or DMSO control were then added (0.25% DMSO final concentration) and 0 h pictures taken with a camera-mounted Olympus IX-71 microscope (10× objective). Plates were returned to the incubator until 24 h pictures were taken. Images were processed and % migration determined via ImageJ. All experiments were performed in quadruplicate.

Western Blot Analysis. Cells were counted via Trypan blue exclusion and were seeded at 100,000 cells/mL in 10 cm dishes and placed back in the incubator for 24 h. Compounds or vehicle were dosed (0.25% DMSO final concentration) and incubated together for 24 h. Cells were harvested in cold PBS and lysed using MPER (Thermo Scientific) supplemented with protease inhibitors (Roche) according the manufacturer's instructions. Cell lysates were obtained by centrifugation at 15,000 rpm for 10 min at 4° C. Protein concentrations were determined using the Pierce BCA assay kit following the manufacturer's instructions. Equal amounts of protein were separated via gel electrophoresis under reducing conditions (10% acrylamide gels) then transferred to PVDF membranes and immunoblotted with the corresponding primary antibodies. Membranes were then incubated with the correct HRP-labeled secondary antibody, developed with a chemiluminescent substrate, and visualized.

Results and Discussion

Compounds 6 and 7 were evaluated via a fluorescence polarization assay to determine Grp94 affinity and selectivity.[16] As seen in Table 1, 6 manifested an apparent $K_d$ of 0.63 µM along with 32-fold selectivity for Grp94 over Hsp900a, which represented ~2-fold improvement over 2. Alternatively, 7 exhibited a significant reduction in both affinity and selectivity (apparent $K_d$=10.4 µM and >10-fold selective) for Grp94. Without being bound by theory, ti appears reduction of the angle between the resorcinol moiety and the benzyl side chain was beneficial for Grp94 affinity and selectivity.

TABLE 1

Evaluation of 6 and 7 via a fluorescence polarization assay against Grp94 and Hsp90α.

| Compound | Apparent $K_d$ Grp94 (µM) | Apparent $K_d$ Hsp90α (µM) | Fold Selective for Grp94 |
|---|---|---|---|
| 6 | 0.63 ± 0.03 | 20.7 ± 0.5 | 32 |
| 7 | 10.4 ± 0.2 | >100[a] | >10 |

[a]100 µM was the highest concentration tested. Apparent $K_d$ values are the average of two independent experiments ± SEM.

Data obtained via fluorescence polarization with compounds 16-24 (Table 2) showed that incorporation of hydrogen bond acceptors (16-18) did not significantly improve affinity (apparent $K_d$'s=0.45-0.73 µM). However, hydrogen bond donors (19, 20, 22-24) did improve Grp94 affinity and resulted in compounds that manifested an apparent $K_d$ value between 0.24-0.54 µM. However, both hydrogen bond acceptors and donors produced a significant loss in Grp94 selectivity. Of these, 18 manifested the highest selectivity (19-fold), which was considerably less than compound 6 which was 32-fold selective. Replacement of the phenyl ring with a pyridine linker (21) resulted in a substantial increase in Grp94 affinity (apparent $K_d$=0.18 µM) as compared to 6, however this substitution also produced high affinity for Hsp90α (0.16 µM) and resulted in no selectivity between these two isoforms.

TABLE 2

Evaluation of 16-24 via a fluorescence polarization assay against Grp94 and Hsp90α

| Compound | Apparent $K_d$ Grp94 (µM) | Apparent $K_d$ Hsp90α (µM) | Fold Selective for Grp94 |
|---|---|---|---|
| 16 | 0.45 ± 0.04 | 2.2 ± 0.2 | 5 |
| 17 | 0.68 ± 0.04 | 2.6 ± 0.6 | 4 |
| 18 | 0.73 ± 0.1 | 13.7 ± 1.4 | 19 |
| 19 | 0.28 ± 0.04 | 1.0 ± 0.1 | 4 |
| 20 | 0.24 ± 0.04 | 0.34 ± 0.07 | n/a |
| 21 | 0.18 ± 0.01 | 0.16 ± 0.02 | n/a |
| 22 | 0.30 ± 0.03 | 2.1 ± 0.1 | 7 |
| 23 | 0.33 ± 0.01 | 0.92 ± 0.03 | 3 |
| 24 | 0.54 ± 0.02 | 2.0 ± 0.2 | 4 |

Note: Apparent $K_d$ values are the average of two independent experiments + SEM.

Incorporation of 2-ethoxy- and 2-methoxybenzyl side chains onto the phenyl-linked analogue was pursued to further increase Grp94 selectivity. Upon their preparation, 25 and 26 were evaluated and shown to manifest a significant loss in affinity (apparent $K_d$=6.1 µM and 7.8 µM, respectively, Table 3) compared to 3 and 4. Without being bound by theory, the loss in affinity exhibited by 25 (compared to 3) suggests the phenyl linker does not bind in an overlapping manner similar to the original imidazole-linked inhibitors. Therefore, a chloride scan was performed to identify an optimal side chain for the phenyl-linked analogues. 27-29 were evaluated for Grp94 affinity and selectivity via fluorescence polarization and as shown in Table 3, 27 and 29 manifested >18- and >24-fold selectivity for Grp94. However, this gain in selectivity was accompanied by ~10-fold reduction in Grp94 affinity as compared to 6. Due to the size difference between the hydrogen of 6 and the chloride of 29, a fluoride was incorporated into the 4-position of the side chain to reduce detrimental steric interactions. Gratifyingly, 30 produced an apparent $K_d$ of 0.54 µM and was 73-fold selective for Grp94. Without being bound by theory, the smaller fluoride substitution (compared to the chloride of 29) appears to minimize steric interactions with the hydrophobic pocket and produce increased Grp94 affinity as compared to 6.

Due to the high selectivity of the 4-fluorobenzyl side chain, it too was incorporated into the highest affinity linker in an effort to combine the high affinity and selectivity of 21 with 30 in the form of 31. Evaluation of 31 against Grp94 and Hsp90a via fluorescence polarization gave apparent $K_d$ values of 0.36 µM and 0.46 µM, respectively. Ultimately, the 4-fluoro side chain produced ~2-fold loss in Grp94 affinity (compared to 21) and a loss of selectivity.

TABLE 3

Evaluation of 25-31 via a fluorescence polarization assay against Grp94 and Hsp90α.

| Compound | Apparent $K_d$ Grp94 (µM) | Apparent $K_d$ Hsp90g (µM) | Fold Selective for Grp94 |
|---|---|---|---|
| 25 | 6.1 ± 0.3 | >100[a] | >16 |
| 26 | 7.8 ± 0.4 | >100[a] | >13 |
| 27 | 5.5 ± 0.1 | >100[a] | >18 |
| 28 | 11.9 ± 1.8 | 44.6 ± 2.0 | 4 |

TABLE 3-continued

Evaluation of 25-31 via a fluorescence polarization assay against Grp94 and Hsp90α.

| Compound | Apparent $K_d$ Grp94 (μM) | Apparent $K_d$ Hsp90g (μM) | Fold Selective for Grp94 |
|---|---|---|---|
| 29 | 4.2 ± 0.7 | >100[a] | 24 |
| 30 | 0.54 ± 0.05 | 39.2 ± 2.7 | 73 |
| 31 | 0.36 ± 0.02 | 0.46 ± 0.03 | n/a |

[a] 100 μM was the highest concentration tested. Apparent $K_d$ values are the average of two independent experiments ± SEM.

Additional compounds and their associated fluorescence polarization assay results against Grp94 and Hsp90a ("Alpha") are provided below:

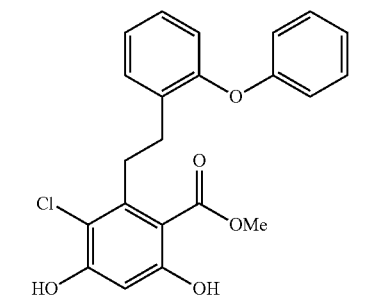

Grp94: 0.45 μM
Alpha: 19.7 μM
Selectivity: 43

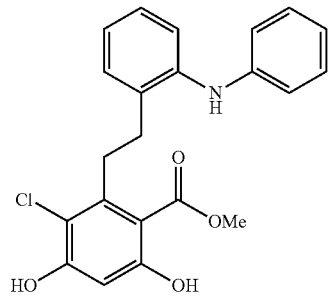

Grp94: 0.45 μM
Alpha: 19.7 μM
Selectivity: 8

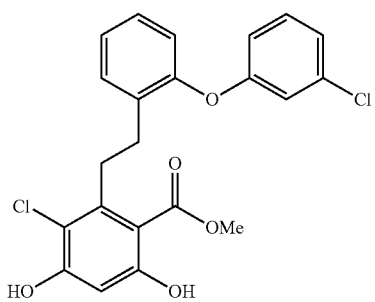

Grp94: 2.1 μM
Alpha: >100 μM
Selectivity: >48 x

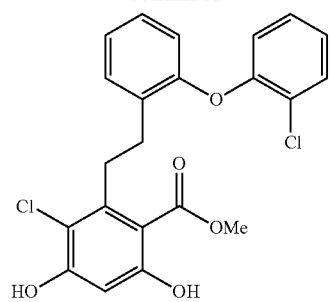

Grp94: 2.3 μM
Alpha: >100 μM
Selectivity: >44 x

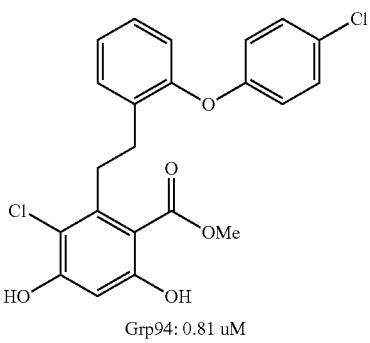

Grp94: 0.81 uM
Alpha: >100 uM
Selectivity: >123 x

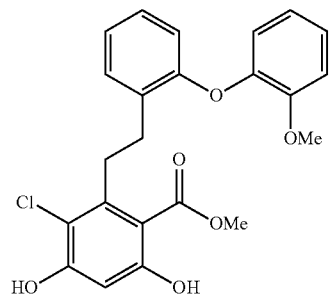

Grp94: 2.9 uM
Alpha: 41.9 uM
Selectivity: 14 x

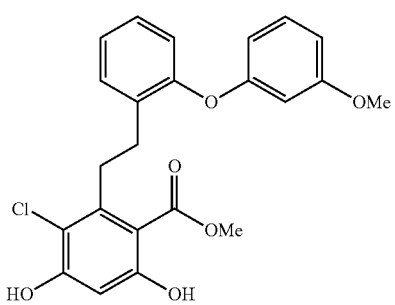

Grp94: 1.8 uM
Alpha: >100 uM
Selectivity: >56 x

-continued
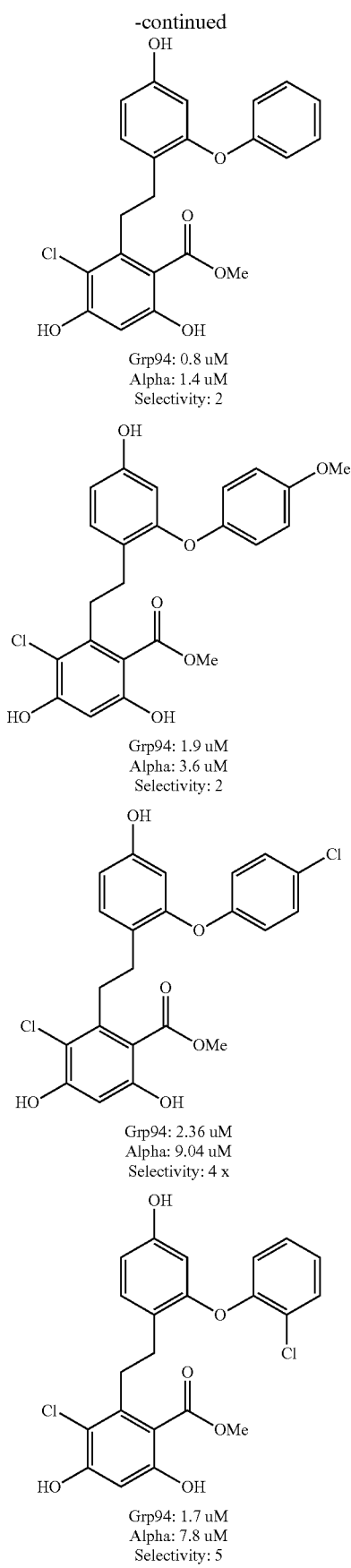
Grp94: 0.8 uM
Alpha: 1.4 uM
Selectivity: 2
Grp94: 1.9 uM
Alpha: 3.6 uM
Selectivity: 2
Grp94: 2.36 uM
Alpha: 9.04 uM
Selectivity: 4 x
Grp94: 1.7 uM
Alpha: 7.8 uM
Selectivity: 5
-continued
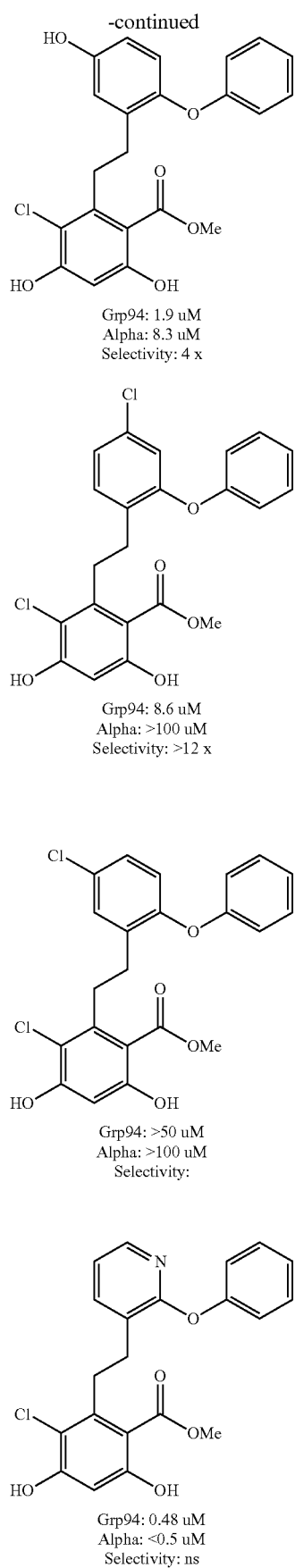
Grp94: 1.9 uM
Alpha: 8.3 uM
Selectivity: 4 x
Grp94: 8.6 uM
Alpha: >100 uM
Selectivity: >12 x
Grp94: >50 uM
Alpha: >100 uM
Selectivity:
Grp94: 0.48 uM
Alpha: <0.5 uM
Selectivity: ns

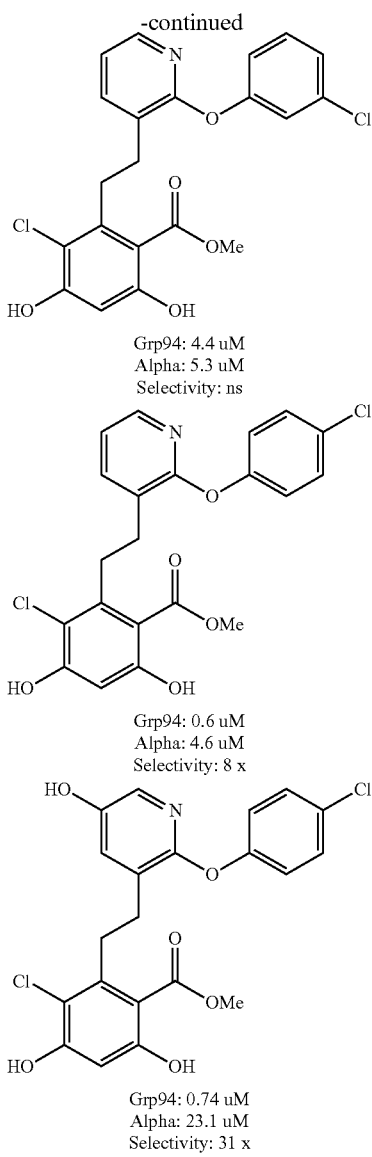

Grp94: 4.4 uM
Alpha: 5.3 uM
Selectivity: ns

Grp94: 0.6 uM
Alpha: 4.6 uM
Selectivity: 8 x

Grp94: 0.74 uM
Alpha: 23.1 uM
Selectivity: 31 x

Cell Study Against Metastatic Cancer Lines 30 was used for further evaluation in a cellular model of metastatic cancer. Grp94 overexpression is seen in metastatic cancer cells compared to less aggressive cancers.[16-17] Integrins are dependent upon Grp94 for their maturation and trafficking to the cell surface and interact with the extracellular matrix to provide a mechanism for oncogenic cell migration away from the primary tumor site to form metastatic lesions.[19]

Figure 3:
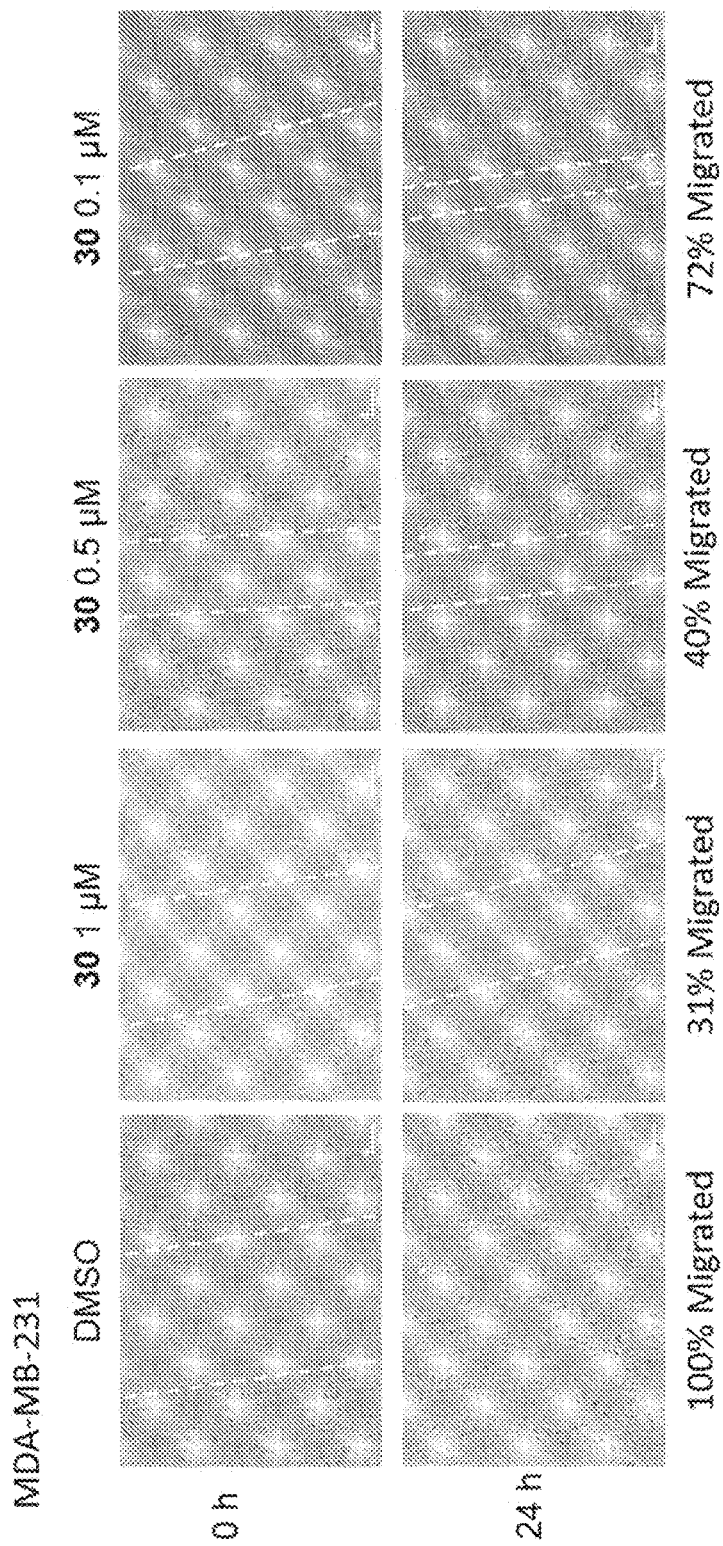
FIG. 3: Representative images of a wound healing scratch assay in MDA-MB-231 cancer cell line after 24 h treatment with 30 or vehicle (0.25% final concentration of DMSO), according to the working examples. Scale bar=100 μm.
Figure 4:
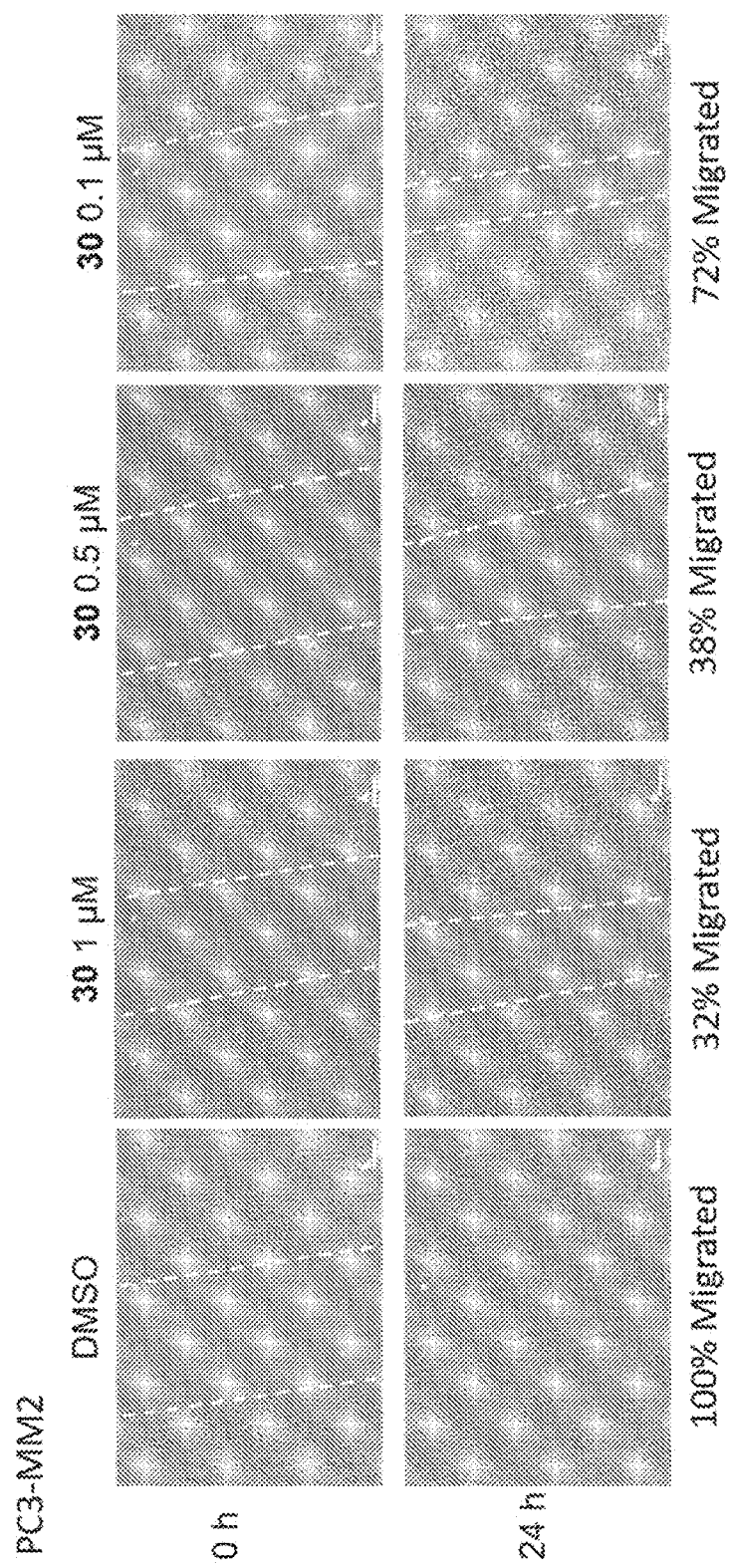
FIG. 4: Representative images of a wound healing scratch assay in PC3-MM2 cancer cell line after 24 h treatment with 30 or vehicle (0.25% final concentration of DMSO), according to the working examples. Scale bar=100 μm.

Evaluation of 30 in a wound healing scratch assay was used to determine the potential of Grp94 inhibitors against different cancers. Grp94-selective inhibition was effective at reducing the migratory capabilities of metastatic breast (MDA-MB-231) and prostate (PC3-MM2) cell lines. Against these cell lines, treatment with 30 produced 38-40% migration (~60% inhibition) at 500 nM after 24 h and exhibited good effects at lower concentrations (FIG. 1, FIG. 3 and FIG. 4). This anti-migratory effect was observed at concentrations much lower than the $GI_{50}$ manifested by 30 against these cell lines (Table 5), which together demonstrate that Grp94-selective inhibition results in an anti-migratory effect that is not due to decreased proliferation.

Figure 5:
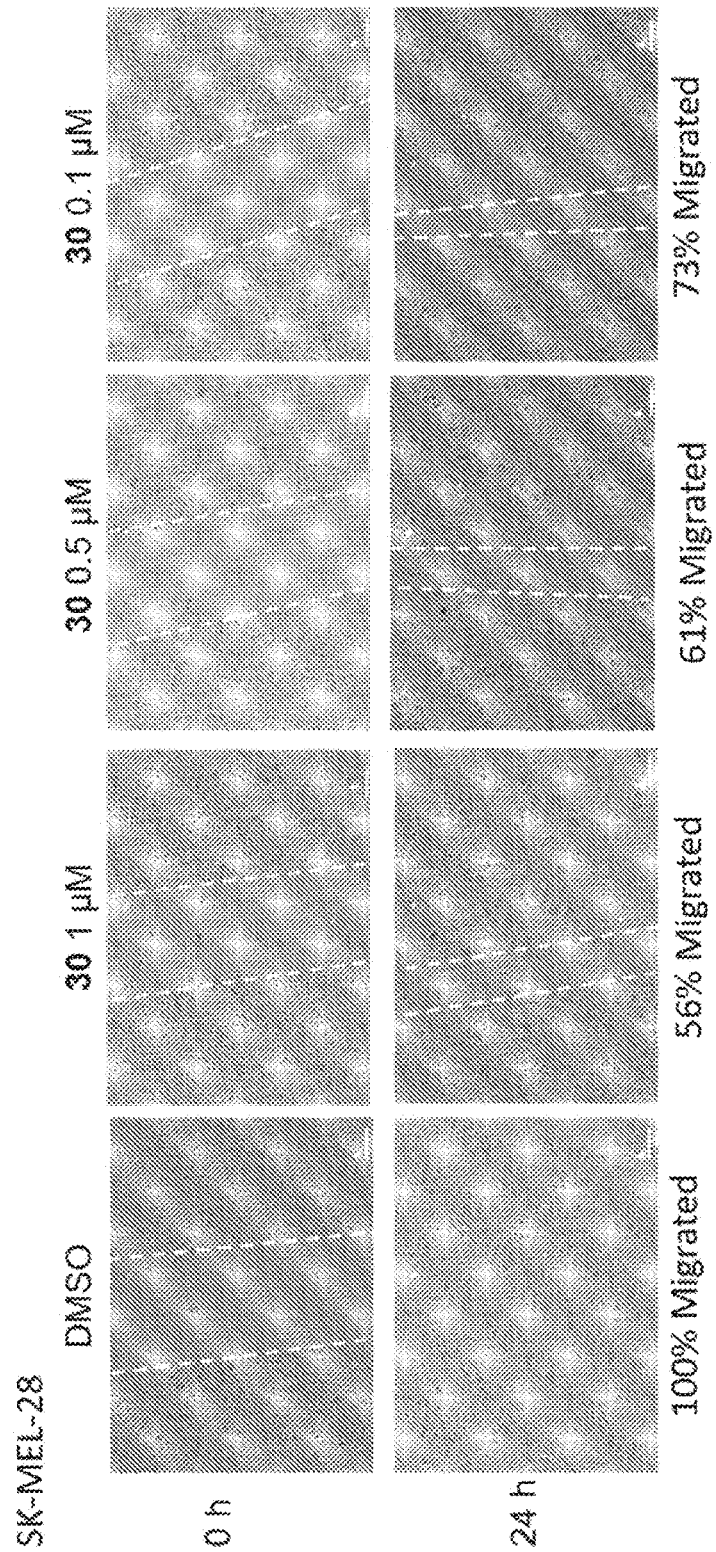
FIG. 5: Representative images of a wound healing scratch assay in SK-MEL-28 cancer cell line after 24 h treatment with 30 or vehicle (0.25% final concentration of DMSO), according to the working examples. Scale bar=100 μm.

Based on these results, 30 was evaluated in a melanoma cell line to determine whether Grp94-selective inhibition could provide therapeutic value in reducing the migration of other aggressive cancers. Metastatic melanoma (SK-MEL-28) cells demonstrated a susceptibility to Grp94 inhibition after 24 h (FIG. 1 and FIG. 5).

TABLE 5

| $GI_{50}$ of cancer cell lines | |
| --- | --- |
| Cell Line | $GI_{50}$ (μM) |
| MDA-MB-231 | 22.4 ± 1.9 |
| PC3-MM2 | 18.3 ± 2.3 |
| SK-MEL-28 | 16.6 ± 1.2 |
| A549 | 16.7 ± 1.1 |

$GI_{50}$ were determined using the MTS/PMS assay. Values are the average of two independent experiments ± SEM.

Figure 2:
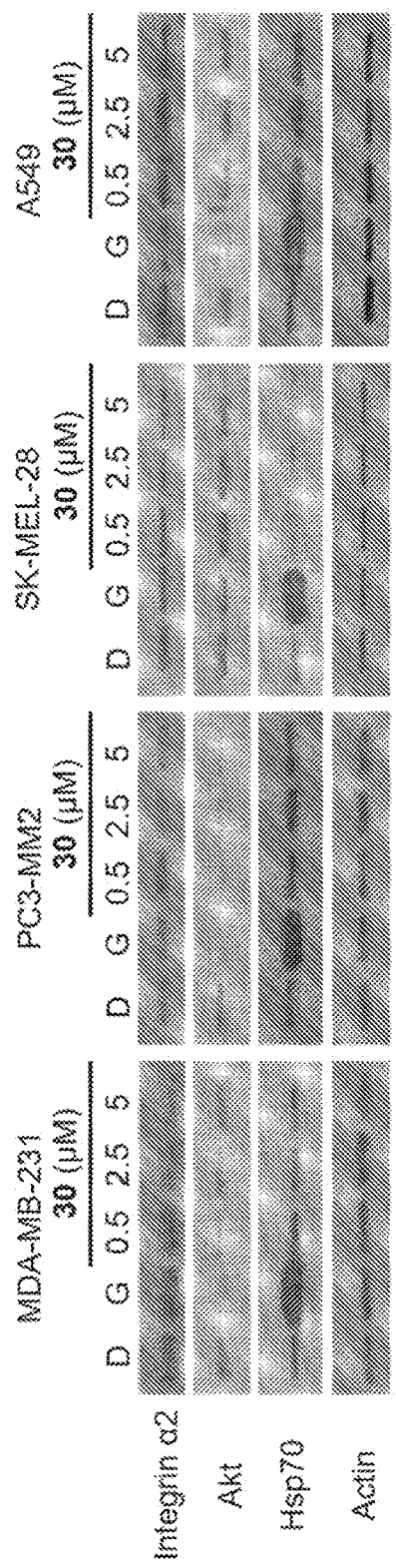
FIG. 2: Western blot analysis for the Grp94-dependent client protein Integrin α2, the cytosolic Hsp90-dependent client protein Akt, Hsp70, and loading control actin after treatment with 30 at indicated concentrations for 24 h (0.1% DMSO final concentration), according to the working examples. D=DMSO, G=geldanamycin, a natural product, pan-Hsp90 inhibitor (0.5 μM).
Figure 6:
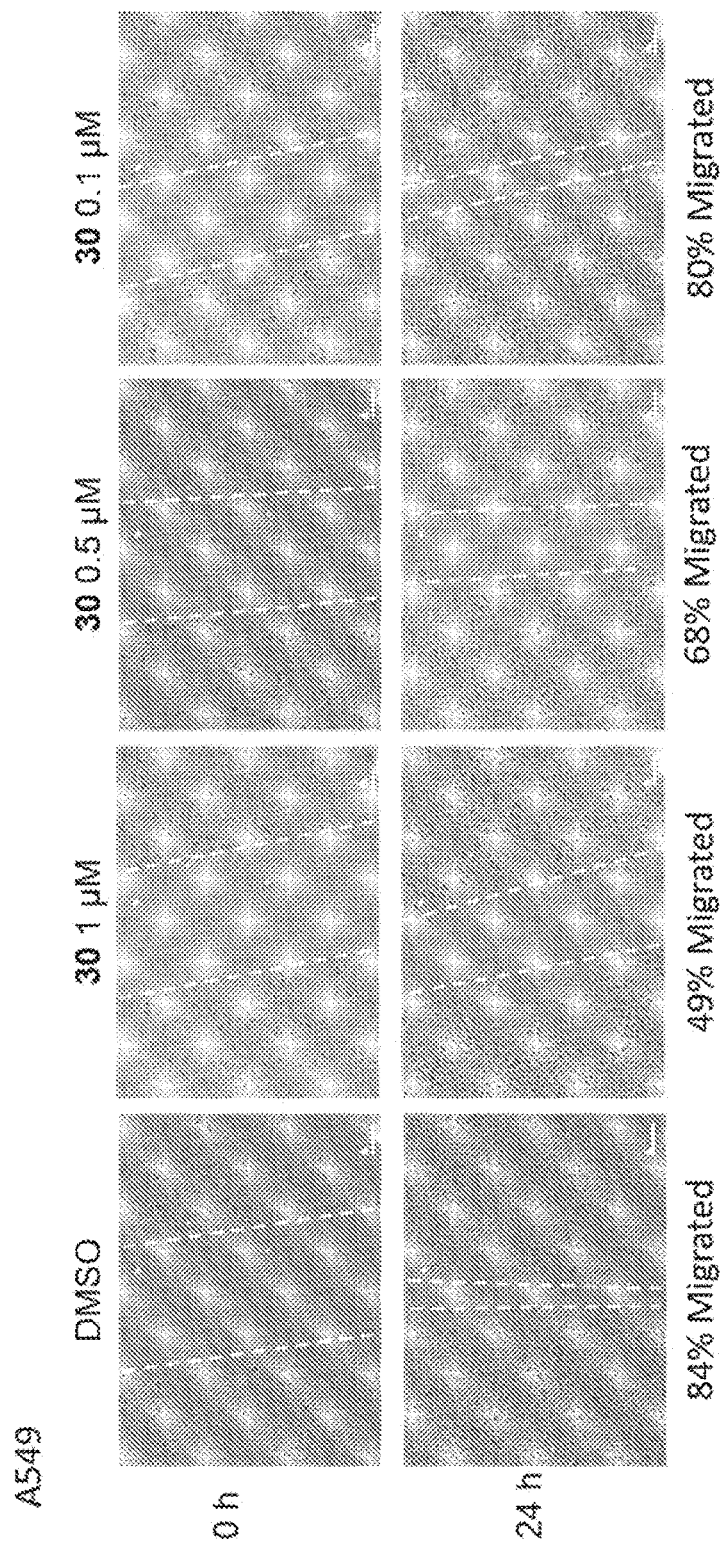
FIG. 6: Representative images of a wound healing scratch assay in A549 cancer cell line after 24 h treatment with 30 or vehicle (0.25% final concentration of DMSO), according to the working examples. Scale bar=100 μm.

Grp94-selective inhibition with 30 was evaluated against a non-metastatic lung cancer cell line (A549) and demonstrated an anti-migratory effect at 500 nM, however this effect was reduced when compared to the highly metastatic breast, prostate, and melanoma cancers above due to the non-aggressive nature of the A549 cell line (FIG. 1 and FIG. 6). There is overexpression of Grp94 in aggressive cancers. The integrin α2 subunit is dependent upon Grp94 for its maturation and trafficking to the cell surface.[18b] Integrin α2 is found as a heterodimer with the β1 integrin subunit and is responsible for binding collagen in the extracellular matrix, which promotes cancer metastasis and invasion.[21] Increased expression of integrin α2β1 has been reported, in both primary and metastatic tissue samples of melanoma from patients.[22] Treatment with 30 resulted in degradation of the integrin α2 subunit at 2.5 μM in the metastatic cancer cell lines (MDA-MB-231, PC3-MM2, SK-MEL-28, FIG. 2). When treated with 30, the non-metastatic cancer cell line (A549) exhibited the degradation of integrin α2, however, this effect was not observed until 5 μM, which correlated with the diminished anti-migratory activity exhibited against this cell line. Treatment with 30 did not induce the degradation of Akt, a cytosolic Hsp90-dependent protein, nor did it result in the induction of Hsp70 This is in contrast to the natural product and pan-Hsp90 inhibitor geldanamycin (G, FIG. 2), which induced the degradation of Akt and increased the levels of Hsp70 in all cell lines. These data demonstrate that 30 selectively targets Grp94 and induces the degradation of Grp94-specific client proteins without decreasing the levels of proteins that depend upon the cytosolic Hsp90 isoforms.

As illustrated above, the present technology provides Grp94 inhibitors that reduce the migration/metastasis of many aggressive cancers.

REFERENCES

[1] aD. Hanahan, R. A. Weinberg, *Cell* 2011, 144, 646-674; bY. Miyata, H. Nakamoto, L. Neckers, *Curr. Pharm. Des.* 2013, 19, 347-365.

[2] aJ. Travers. S. Sharp, P. Workman, *Drug Discov. Today* 2012, 17, 242-252; bA. Khandelwal, V. M. Crowley, B. S. Blagg, *Med. Res. Rev.* 2016, 36, 92-118.

[3] aL. Neckers, P. Workman, *Clin. Cancer Res.* 2012, 18, 64-76; bM. Taipale, D. F. Jarosz, S. Lindquist, *Nat. Rev. Mol. Cell Biol.* 2010, 11, 515-528.

[4] J. T. Ernst, M. Liu, H. Zuccola, T. Neubert, K. Beaumont, A. Turnbull, A. Kallel, B. Vought, D. Stamos, *Bioorg. Med. Chem. Lett.* 2014, 24, 204-208.

[5] D. T. Gewirth, *Curr. Top. Med. Chem.* 2016, 16, 2779-2791.

[6] M. Marzec, D. Eletto, Y. Argon, *Biochim. Biophys. Acta* 2012, 1823, 774-787.

[7] aY. Hua, S. White-Gilbertson, J. Kellner, S. Rachidi, S Z. Usimani, G. Chiosis, R. Depinho, Z. Li, B. Liu, *Clin. Cancer Res.* 2013, 19, 6242-6251; bA. R. Stothert, A. Suntharalingam, D. J. Huard, S. N. Fontaine, V. M. Crowley, S. Mishra, B. S. Blagg, R. L. Lieberman, C. A. Dickey, *Hum. Mol. Genet.* 2014, 23, 6470-6480.

[8] F. Randow, B. Seed, *Nat. Cell Biol.* 2001, 3, 891-896.

[9] aB. Chen, W. H. Piel, L. Gui, E. Bruford, A. Monteiro, *Genomics* 2005, 86, 627-637; bT. Taldone, P. D. Patel, M. Patel, H. J. Patel, C. E. Evans, A. Rodina, S. Ochiana, S. K. Shah, M. Uddin, D. Gewirth, G. Chiosis, *J. Med Chem.* 2013, 56, 6803-6818; cH. Y. Song, J. D. Dunbar, Y. X. Zhang, D. Guo, D. B. Donner, *J. Biol. Chem.* 1995, 270, 3574-3581.

[10] A. S. Duerfeldt, L. B. Peterson, J. C. Maynard, C. L. Ng, D. Eletto, O. Ostrovsky, H. E. Shinogle, D. S. Moore, Y. Argon, C. V. Nicchitta, B. S. Blagg, *J. Am. Chem. Soc.* 2012, 134, 9796-9804.

[11] V. M. Crowley, A. Khandelwal, S. Mishra, A. R. Stothert, D. J. Huard, J. Zhao, A. Muth, A. S. Duerfeldt, J. L. Kizziah, R. L. Lieberman, C. A. Dickey, B. S. Blagg, *J. Med Chem.* 2016, 59, 3471-3488.

[12] R. M. Immormino, L. E. t. Metzger, P. N. Reardon, D. E. Dollins, B. S. Blagg, D. T. Gewirth, *J. Mol. Biol.* 2009, 388, 1033-1042.

[13] K. Ohsawa, M. Yoshida, T. Doi, *J. Org. Chem.* 2013, 78, 3438-3444.

[14] B. L. Dutton. R. R. Kitson, S. Parry-Morris, S. M. Roe, C. Prodromou, C. J. Moody, *Organic & biomolecular chemistry* 2014, 12, 1328-1340.

[15] H. J. W. Li, L., *Eur. J. Org. Chem.* 2006, 2006, 5099-5102.

[16] T. Hu, N. Xie, C. Qin, J. Wang, Y. You, *Tumour Biol.* 2015, 36, 9357-9364.

[17] N. Dejeans, C. Glorieux, S. Guenin, R. Beck, B. Sid, R. Rousseau, B. Bisig, P. Delvenne, P. Buc Calderon, J. Verrax, *Free Radic. Biol. Med* 2012, 52, 993-1002.

[18] aA. Muth, V. Crowley, A. Khandelwal, S. Mishra, J. Zhao, J. Hall, B. S. Blagg, *Bioorg. Med Chem.* 2014, 22, 4083-4098; bS. Ghosh, H. E. Shinogle, N. A. Galeva, R. T. Dobrowsky, B. S. Blagg, *J. Biol. Chem.* 2016, 291, 8309-8323; cS. J. Mishra, S. Ghosh, A. R. Stothert, C. A. Dickey, B. S. Blagg, *ACS Chem. Biol.* 2017, 12, 244-253.

[19] aB H. Luo, C. V. Carman, T. A. Springer, *Annu. Rev. Immunol.* 2007, 25, 619-647; bS. Wu, F. Hong, D. Gewirth, B. Guo, B. Liu, Z. Li, *J. Biol. Chem.* 2012, 287, 6735-6742.

[20] aL. Guo, F. Zhang, Y. Cai, T. Liu, *Pathol. Res. Pract.* 2009, 205, 847-853; bA. Gogali, K. Charalabopoulos, S. Constantopoulos, *Exp. Oncol.* 2004, 26, 106-110.

[21] aD. Naci, K. Vuori, F. Aoudjit, *Semin. Cancer Biol.* 2015, 35, 145-153; bM. Haidari, W. Zhang, A. Caivano, Z. Chen, L. Ganjehei, A. Mortazavi, C. Stroud, D. G. Woodside, J. T. Willerson, R. A. Dixon, *J. Biol. Chem.* 2012, 287, 32981-32992.

[22] D. Schadendoif, C. Gawlik, U. Haney, H. Ostmeier, L. Suter, B. M. Czarnetzki, *J. Pathol.* 1993, 170, 429-434.

[23] D. E. Dollins, J. J. Warren, R. M. Immormino, D. T. Gewirth, *Mol Cell* 2007, 28, 41-56.

[24] W. Minor, M. Cymborowski, Z. Otwinowski, M. Chruszcz, *Acta Crystallogr D* 2006, 62, 859-866.

[25] W. Kabsch, *Acta Crystallogr D* 2010, 66, 125-132.

[26] P. R. Evans, G. N. Murshudov, *Acta Crystallogr D* 2013, 69, 1204-1214.

[27] A. J. Mccoy, R. W. Grosse-Kunstleve, P. D. Adams, M. D. Winn, L. C. Storoni, R. J. Read, *J. Appl Crystallogr* 2007, 40, 658-674.

[28] P. Emsley, B. Lohkamp, W. G. Scott, K. Cowtan, *Acta Crystallogr D* 2010, 66, 486-501.

[29] P. D. Adams, P. V. Afonine, G. Bunkoczi, V. B. Chen, I. W. Davis, N. Echols, J. J. Headd, L. W. Hung, G. J. Kapral, R. W. Grosse-Kunstleve, A. J. McCoy, N. W. Moriarty, R. Oeffner, R. J. Read, D. C. Richardson, J. S. Richardson, T. C. Terwilliger, P. H. Zwart, *Acta Crystallogr D* 2010, 66, 213-221.

[30] Quigley, H. A., and Broman, A. T. (2006) The number of people with glaucoma worldwide in 2010 and 2020. *Br. J. Ophthalmol.* 90, 262-267.

[31] Stone, E. M., Fingert, J. H., Alward, W. L., Nguyen, T. D., Polansky, J. R., Sunden, S. L., Nishimura, D., Clark, A. F., Nystuen, A., Nichols, B. E., Mackey, D. A., Ritch, R., Kalenak, J. W., Craven, E. R., and Sheffield, V. C. (1997) Identification of a gene that causes primary open angle glaucoma. *Science* 275, 668-670.

[32] Resch, Z. T., and Fautsch, M. P. (2009) Glaucoma-associated myocilin: a better understanding but much more to learn. *Exp. Eye Res.* 88, 704-712.

[33] Kwon, Y. H., Fingert, J. H., Kuehn, M. H., and Alward, W. L. (2009) Primary open-angle glaucoma. *N. Engl. J. Med.* 360, 1113-1124.

[34] Hardy, K. M., Hoffman, E. A., Gonzalez, P., McKay, B. S., and Stamer, W. D. (2005) Extracellular trafficking of myocilin in human trabecular meshwork cells. *J. Biol. Chem.* 280, 28917-28926.

[35] Filla, M. S., Liu, X., Nguyen, T. D., Polansky, J. R., Brandt, C. R., Kaufman, P L, and Peters, D M. (2002) In vitro localization of TIGR/MYOC in trabecular meshwork extracellular matrix and binding to fibronectin. *Invest. Ophthalmol. Vis. Sci.* 43, 151-161.

[36] Tawara, A., Okada, Y., Kubota, T., Suzuki, Y., Taniguchi, F., Shirato, S., Nguyen, T. D., and Ohnishi, Y. (2000) Immunohistochemical localization of MYOC/TIGR protein in the trabecular tissue of normal and glaucomatous eyes. *Curr. Eye Res.* 21, 934-943.

[37] Wentz-Hunter, K., Kubota, R., Shen, X., and Yue, B. Y. (2004) Extracellular myocilin affects activity of human trabecular meshwork cells. *J. Cell. Physiol.* 200, 45-52.

[38] Alward, W. L. (1998) Medical management of glaucoma. *N. Engl. J. Med.* 339, 1298-1307.

[39] Donegan, R. K., and Lieberman, R. L. (2016) Discovery of molecular therapeutics for glaucoma: challenges, successes, and promising directions. *J. Med Chem.* 59, 788-809

[40] Hewitt, A. W., Mackey, D. A., and Craig, J. E. (2008) Myocilin allele-specific glaucoma phenotype database. *Hum. Mutat.* 29, 207-211.

[41] Burns, J. N., Orwig, S. D., Harris, J. L., Watkins, J. D., Vollrath, D, and Lieberman, R. L. (2010) Rescue of glaucoma-causing mutant myocilin thermal stability by chemical chaperones. *ACS Chem. Biol.* 5, 477-487.

[42] Burns, J. N., Turnage, K. C., Walker, C. A., and Lieberman, R. L. (2011) The stability of myocilin olfactomedin domain variants provides new insight into glaucoma as a protein misfolding disorder. *Biochemistry* 50, 5824-5833.

[43] Donegan, R. K., Hill, S. E., Freeman, D. M., Nguyen, E., Orwig, S. D., Turnage, K. C., and Lieberman, R. L. (2015) Structural basis for misfolding in myocilin-associated glaucoma. *Hum. Mol. Genet.* 24, 2111-2124.

[44] Liu, Y., and Vollrath, D. (2004) Reversal of mutant myocilin non-secretion and cell killing: implications for glaucoma. Hum Mol. Genet. 13, 1193-1204.

[45] Jacobson, N., Andrews, M., Shepard, A. R., Nishimura, D., Searby, C., Fingert, J H., Hageman, G., Mullins, R., Davidson, B. L., Kwon, Y. H., Alward, W. L., Stone, E. M., Clark, A. F., and Sheffield, V. C. (2001) Non-secretion of mutant proteins of the glaucoma gene myocilin in cultured trabecular meshwork cells and in aqueous humor. Hum. Mol. Genet. 10, 117-125.

[46] Joe, M. K., Sohn, S., Hur, W., Moon, Y., Choi, Y. R., and Kee, C. (2003) Accumulation of mutant myocilins in ER leads to ER stress and potential cytotoxicity in human trabecular meshwork cells. Biochem. Biophys. Res. Commun. 312, 592-600.

[47] Suntharalingam, A., Abisambra, J. F., O'Leary, J. C, 3rd, Koren, J., 3rd, Zhang, B., Joe, M. K., Blair, L. J., Hill, S. E., Jinwal, U. K. Cockman, M., Duerfeldt, A. S., Tomarev, S., Blagg, B. S., Lieberman, R. L., and Dickey, C. A. (2012) Glucose-regulated protein 94 triage of mutant myocilin through endoplasmic reticulum-associated degradation subverts a more efficient autophagic clearance mechanism. J. Biol. Chem. 287, 40661-40669.

[48] Yam, G. H., Gaplovska-Kvsela, K., Zuber, C., and Roth, J. (2007) Aggregated myocilin induces russell bodies and causes apoptosis: implications for the pathogenesis of myocilin-caused primary open-angle glaucoma. Am. J. Pathol. 170, 100-109.

[49] Zode, G. S., Kuehn, M. H., Nishimura, D. Y., Searby, C. C., Mohan, K., Grozdanic, S. D., Bugge, K., Anderson, M. G., Clark, A. F., Stone, E. M., and Sheffield, V. C. (2011) Reduction of ER stress via a chemical chaperone prevents disease phenotypes in a mouse model of primary open angle glaucoma. J. Clin. Invest 121, 3542-3553.

[50] Kanagavalli, J., Pandaranavaka, P. J., Krishnadas, S. R., Krishnaswamy, S., and Sundaresan, P. (2007) In vitro and in vivo study on the secretion of the Gly367Arg mutant myocilin protein. Mol. Vis. 13, 1161-1168.

[51] Wang, L., Zhuo, Y., Liu, B., Huang, S., Hou. F., and Ge, J. (2007) Pro370Leu mutant myocilin disturbs the endoplasm reticulum stress response and mitochondrial membrane potential in human trabecular meshwork cells. Mol. Vis. 13, 618-625.

[52] Anholt, R. R., and Carbone, M. A. (2013) A molecular mechanism for glaucoma: endoplasmic reticulum stress and the unfolded protein response. Trends Mol. Med. 19, 586-593.

[53] Acott, T. S., Kelley, M. J., Keller, K. E., Vranka, J. A., Abu-Hassan, D. W., Li, X., Aga, M., and Bradley, J. M. (2014) Intraocular pressure homeostasis: maintaining balance in a high-pressure environment. J. Ocul. Pharmacol. Ther. 30, 94-101.

[54] Meusser, B., Hirsch, C., Jarosch, E., and Sommer, T. (2005) ERAD: the long road to destruction. Nat. Cell Biol. 7, 766-772.

[55] Marzec, M., Eletto, D., and Argon, Y. (2012) GRP94: an HSP90-like protein specialized for protein folding and quality control in the endoplasmic reticulum. Biochim. Biophys. Acta, Mol. Cell Res. 1823, 774-787.

[56] Eletto, D., Dersh, D., and Argon, Y. (2010) GRP94 in ER quality control and stress responses. Semin. Cell Dev. Biol. 21, 479-485.

[57] Stothert, A. R., Suntharalingam, A., Huard, D. J., Fontaine. S. N., Crowley, V. M., Mishra, S., Blagg, B. S., Lieberman, R. L., and Dickey, C. A. (2014) Exploiting the interaction between Grp94 and aggregated myocilin to treat glaucoma Hum. Mol. Genet. 23, 6470-6480.

[58] Crowley, V. M., Khandelwal, A., Mishra, S., Stothert, A. R., Huard, D. J. E., Zhao, J. B., Muth, A., Duerfeldt, A. S., Kizziah, J. L., Lieberman, R. L., Dickey, C. A., and Blagg, B. S. J. (2016) Development of glucose regulated protein 94-selective inhibitors based on the BnIm and radamide scaffold. J. Med. Chem. 59, 3471-3488.

[59] Stothert, A. R., Fontaine, S. N., Sabbagh, J. J., and Dickey, C. A. (2016) Targeting the ER-autophagy system in the trabecular meshwork to treat glaucoma. Exp. Eye Res. 144, 38-45.

[60] Chen. B., Piel, W. H., Gui, L., Bruford, E., and Monteiro, A. (2005) The HSP90 family of genes in the human genome: insights into their divergence and evolution. Genomics 86, 627-637.

[61] Maynard, J C., Pham, T., Zheng, T., Jockheck-Clark, A., Rankin, H. B., Newgard, C. B., Spana, E. P., and Nicchitta, C. V. (2010) Gp93, the Drosophila GRP94 ortholog, is required for gut epithelial homeostasis and nutrient assimilation-coupled growth control. Dev. Biol. 339, 295-306.

[62] Gewirth, D. T. (2016) Paralog specific Hsp90 inhibitors—a brief history and a bright future. Curr. Top. Med. Chem. 16, 2779-2791.

[63] Dollins, D. E., Warren, J. J., Immormino, R. M., and Gewirth, D. T. (2007) Structures of GRP94-nucleotide complexes reveal mechanistic differences between the hsp90 chaperones. Mol. Cell 28, 41-56.

[64] Soldano, K L., Jivan, A., Nicchitta, C. V., and Gewirth, D. T. (2003) Structure of the N-terminal domain of GRP94—Basis for ligand specificity and regulation. J. Biol. Chem. 278, 48330-48338.

[65] Joe, M. K., Kee, C., and Tomarev, S. 1 (2012) Myocilin interacts with syntrophins and is member of dystrophin-associated protein complex. J. Biol. Chem. 287, 13216-13227.

[66] Lackie, R. E., Maciejewski, A., Ostapchenko, V. G., Marques-Lopes, J., Choy, W. Y., Duennwald, M. L., Prado, V. F., and Prado, M. A. M. (2017) The Hsp70/Hsp90 chaperone machinery in neurodegenerative diseases. Front. Neurosci. 11, 254

[67] Joe, M. K., and Tomarev, S. I. (2010) Expression of myocilin mutants sensitizes cells to oxidative stress-induced apoptosis: implication for glaucoma pathogenesis. Am. J. Pathol. 176, 2880-2890.

[68] Orwig, S. D., Chi, P. V., Du, Y., Hill, S. E., Cavitt, M. A., Suntharalingam, A., Turnage, K. C., Dickey, C. A., France, S., Fu, H., and Lieberman, R. L. (2014) Ligands for glaucoma-associated myocilin discovered by a generic binding assay. ACS Chem. Biol 9, 517-525.

[69] Hill, S. E., Donegan, R. K., and Lieberman, R. L. (2014) The glaucoma-associated olfactomedin domain of myocilin forms polymorphic fibrils that are constrained by partial unfolding and peptide sequence. J. Mol. Biol. 426, 921-935.

[70] Zhang, J. H., Chung, T. D. Y., and Oldenburg, K. R. (1999) A simple statistical parameter for use in evaluation and validation of high throughput screening assays. J. Biomol. Screening 4, 67-73.

[71] Curtis. A. S. G., Forrester, J. V., Mcinnes, C., and Lawrie, F. (1983) Adhesion of cells to polystyrene surfaces. J. Cell Biol. 97, 1500-1506.

[72] Clevenger, R. C., and Blagg, B. S. J. (2004) Design, synthesis, and evaluation of a radicicol and geldanamycin chimera, radamide. Org. Lett. 6, 4459-4462.

[73] Duerfeldt, A. S., Peterson, L. B., Maynard, J. C., Ng, C. L., Eletto, D., Ostrovsky, O., Shinogle, H. E., Moore, D.

S., Argon, Y., Nicchitta, C. V., and Blagg, B. S. J. (2012) Development of a Grp94 inhibitor. *J. Am. Chem. Soc.* 134, 9796-9804.

[74] Ratzke, C., Mickler, M., Hellenkamp, B., Buchner, J., and Hugel, T. (2010) Dynamics of heat shock protein 90 C-terminal dimerization is an important part of its conformational cycle. *Proc. Natl. Acad. Sci. U.S.A.* 107, 16101-16106.

[75] Stothert, A. R., Suntharalingam, A., Tang, X., Crowley, V. M., Mishra, S. J., Webster, J. M., Nordhues, B. A., Huard, D. J. E., Passaglia, C., Lieberman, R. L., Blagg, B. S. J., Blair, L. J., Koren, J. I., and Dickey, C. A. (2017) Isoform-selective Hsp90 inhibition rescues model of hereditary open-angle glaucoma. *Sci. Rep.* 7, 17951.

[76] Cohen, F. E., and Kelly, J. W. (2003) Therapeutic approaches to protein-misfolding diseases. *Nature* 426, 905-909.

[77] Buller, C., Johnson, D. H., and Tschumper, R. C. (1990) Human trabecular meshwork phagocytosis. Observations in an organ culture system. *Invest. Ophthalmol. Vis. Sci.* 31, 2156-2163.

[78] Crowley, V. M., Huard, D. J. E., Lieberman, R. L., and Blagg, B. S. J. (2017) Second generation Grp94-selective inhibitors provide opportunities for the inhibition of metastatic cancer. *Chem.—Eur. J.* 23, 15775-15782.

[79] Khandelwal, A., Kent, C. N., Balch, M., Peng, S., Mishra, S. J., Deng, J., Day, V. W., Liu, W., Subramanian, C., Cohen, M., Holzbeierlein, J. M., Matts, R., and Blagg, B. S. J. (2018) Structure guided design of the first Hsp90b N-terminal isoform-selective inhibitor. *Nat. Commun.* 9, 425.

[80] Anyika, M, McMullen, M., Forsberg, L. K., Dobrowsky, R. T., and Blagg, B. S. (2016) Development of noviomimetics as C-terminal Hsp90 inhibitors. *ACS Med. Chem. Lett.* 7, 67-71.

[81] Kusuma, B. R., Zhang, L., Sundstrom, T., Peterson, L. B., Dobrowsky, R. T., and Blagg, B. S. (2012) Synthesis and evaluation of novologues as C-terminal Hsp90 inhibitors with cytoprotective activity against sensory neuron glucotoxicity. *J. Med. Chem.* 55, 5797-5812.

[82] Burlison, J. A., Avila, C., Vielhauer, G., Lubbers, D. J., Holzbeierlein, J., and Blagg, B. S. J. (2008) Development of novobiocin analogues that manifest anti-proliferative activity against several cancer cell lines. *J. Org. Chem.* 73, 2130-2137.

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such claims:

A. A compound of Formula I

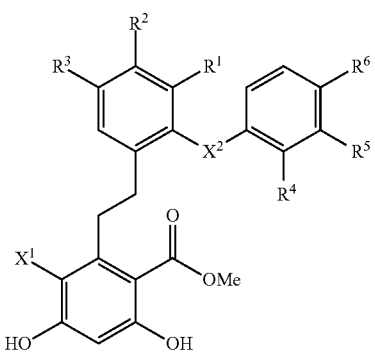

or a pharmaceutically acceptable salt thereof, wherein
$X^1$ is Cl or F;
$X^2$ is $CH_2$, O, S, or NH;
$R^1$, $R^2$, $R^4$, $R^5$, and $R^6$ are each independently H, alkoxy, hydroxyl, thiol, or halo; and
$R^3$ is H, alkoxy, amino, hydroxyl, thiol, or halo.

B. The compound of Paragraph A, wherein the compound is of Formula II:

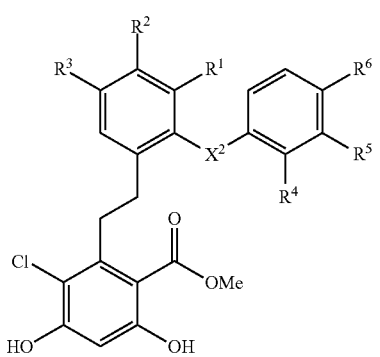

or a pharmaceutically acceptable salt thereof.

C. The compound of Paragraph A or Paragraph B, wherein when $X^2$ is O and $R^4$, $R^5$, and $R^6$ are each independently H, then
$R^1$ and $R^2$ are each independently H, alkoxy, or halo; and
$R^3$ is H, alkoxy, amino, or halo.

D. The compound of any one of Paragraphs A-C, wherein at least two of $R^1$, $R^2$, and $R^3$ are each independently H.

E. The compound of any one of Paragraphs A-D, wherein at least two of $R^4$, $R^5$, and $R^6$ are each independently H.

F. The compound of any one of Paragraphs A-E, wherein when at least one of $R^1$, $R^2$, and $R^3$ is hydroxyl, then at least one of $R^4$, $R^5$, and $R^6$ is not H.

G. The compound of any one of Paragraphs A-F, wherein when one of $R^1$, $R^2$, and $R^3$ is hydroxyl and the remaining $R^1$, $R^2$, and $R^3$ each independently H, then at least one of $R^4$, $R^5$, and $R^6$ is not H.

H. The compound of any one of Paragraphs A-F, wherein $R^1$, $R^2$, and $R^3$ are each independently H.

I. A compound of Formula III

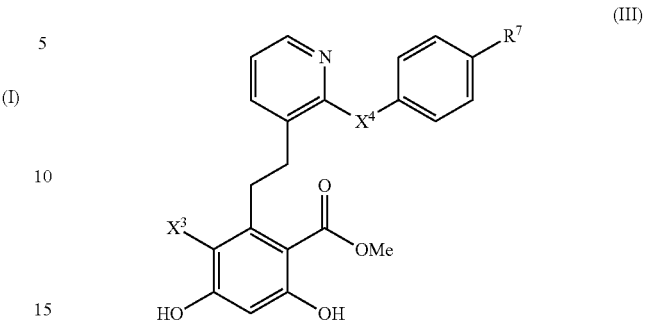

or a pharmaceutically acceptable salt thereof, wherein
$X^3$ is Cl or F;
$X^4$ is $CH_2$, O, S, or NH; and
$R^7$ is alkoxy, hydroxyl, thiol, or halo.

J. A composition comprising a compound of any one of Paragraphs A-I and a pharmaceutically acceptable carrier.

K. A pharmaceutical composition for treating metastatic cancer, the composition comprising an effective amount of the compound of any one of Paragraphs A-I and a pharmaceutically acceptable excipient.

L. The pharmaceutical composition of Paragraph K, wherein the cancer is multiple myeloma, melanoma, lung cancer, hepatocellular carcinoma, breast cancer, or prostate cancer.

M. The pharmaceutical composition of Paragraph K or Paragraph L, wherein the pharmaceutical composition is packaged in unit dosage form.

N. A method for inhibiting cell motility of a cancer cell, the method comprising contacting the cancer cell with a compound of any one of Paragraphs A-I.

O. The method of Paragraph N, wherein the cancer cell is a metastatic multiple myeloma cancer cell, a metastatic melanoma cancer cell, a metastatic lung cancer cell, a metastatic hepatocellular carcinoma cell, a metastatic breast cancer cell, or a metastatic prostate cancer cell.

P. The method of Paragraph N or Paragraph O, wherein the method comprises contacting the cell with an effective amount of the compound.

Q. The method of any one of Paragraphs N-P, wherein the cancer cell is not within a patient.

R. A method of treating a patient or animal suffering from metastatic cancer, the method comprising administration of an effective amount of a compound of any one of Paragraphs A-I to the patient or animal suffering from the metastatic cancer.

S. The method of Paragraph R, wherein administration of the effective amount of the compound to the patient or animal treats the patient or animal suffering from the metastatic cancer.

T. The method of Paragraph R or Paragraph S, wherein the metastatic cancer is multiple myeloma, melanoma, lung cancer, hepatocellular carcinoma, breast cancer, or prostate cancer.

U. The method of any one of Paragraphs R-T, wherein the administration comprises oral administration, parenteral administration, or nasal administration.

V. A pharmaceutical composition for treating glaucoma, the composition comprising an effective amount of the compound of any one of Paragraphs A-I and a pharmaceutically acceptable excipient.

W. The pharmaceutical composition of Paragraph V, wherein the glaucoma is myocilin glaucoma.

X. The pharmaceutical composition of Paragraph V or Paragraph W, wherein the pharmaceutical composition is packaged in unit dosage form.

Y. A method of inhibiting death of a cell exhibiting mutant myocilin, the method comprising contacting the cell with a compound of any one of Paragraphs A-I.

Z. The method of Paragraph Y, wherein the method comprises contacting the cell with an effective amount of the compound.

AA. The method of Paragraph Y or Paragraph Z, wherein the contacting inhibits the death of the cell in comparison to a cell exhibiting mutant myocilin that is not contacted with the compound.

BA. A method of treating a patient or animal suffering from glaucoma, the method comprising administration of an effective amount of a compound of any one of Paragraphs A-I to the patient or animal suffering from the glaucoma.

CA. The method of Paragraph BA, wherein administration of the effective amount of the compound to the patient or animal treats the patient or animal suffering from the cancer or the glaucoma.

DA. The method of Paragraph BA or Paragraph CA, wherein the glaucoma is myocilin glaucoma.

Other embodiments are set forth in the following claims, along with the full scope of equivalents to which such claims are entitled.

What is claimed:
1. A compound of Formula I

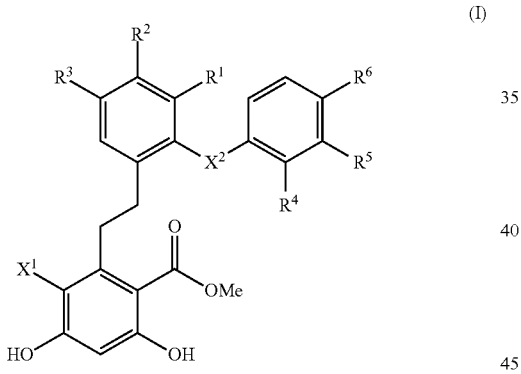

or a pharmaceutically acceptable salt thereof, wherein
$X^1$ is Cl or F;
$X^2$ is $CH_2$ or O;
$R^1$, $R^2$, $R^4$, $R^5$, and $R^6$ are each independently H, alkoxy, hydroxyl, thiol, or halo; and
$R^3$ is H, alkoxy, amino, hydroxyl, thiol, or halo.

2. The compound of claim 1, wherein the compound is

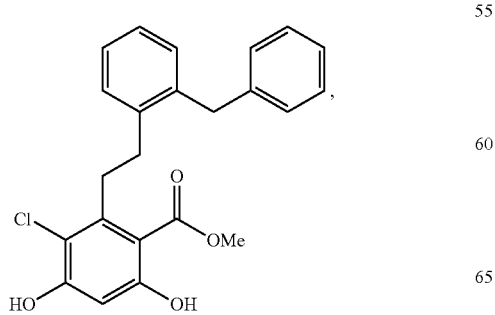

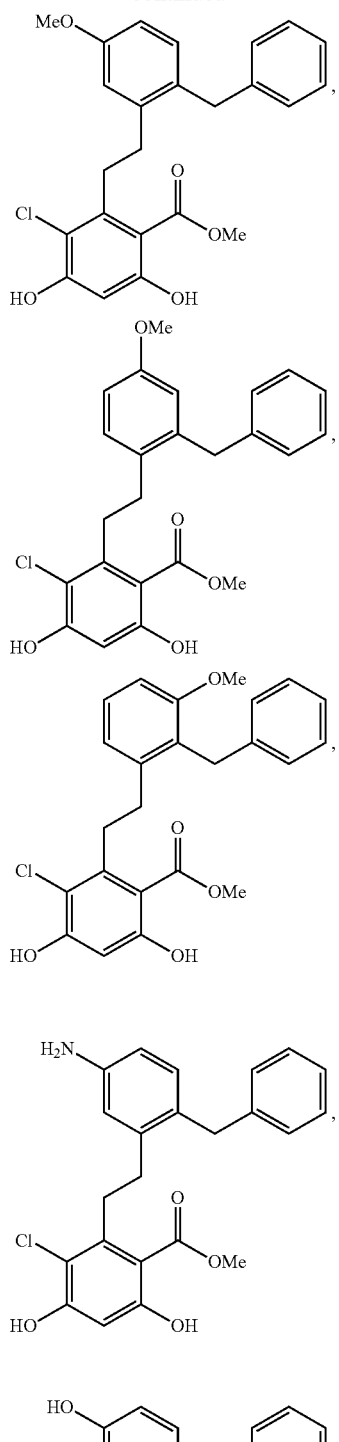

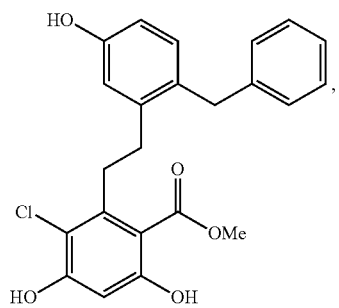

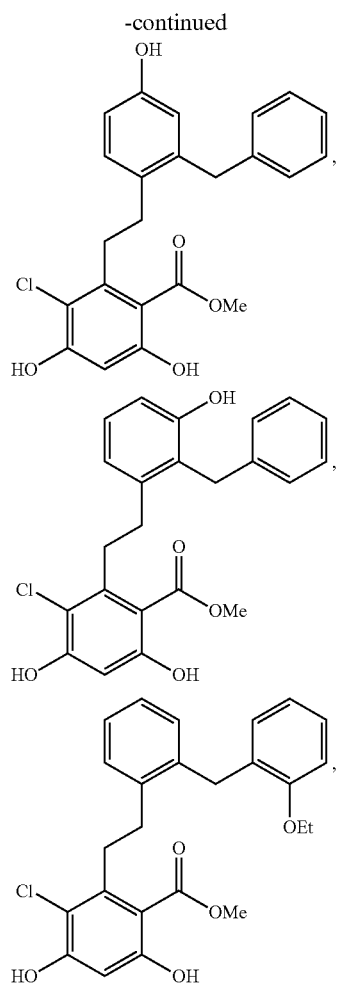
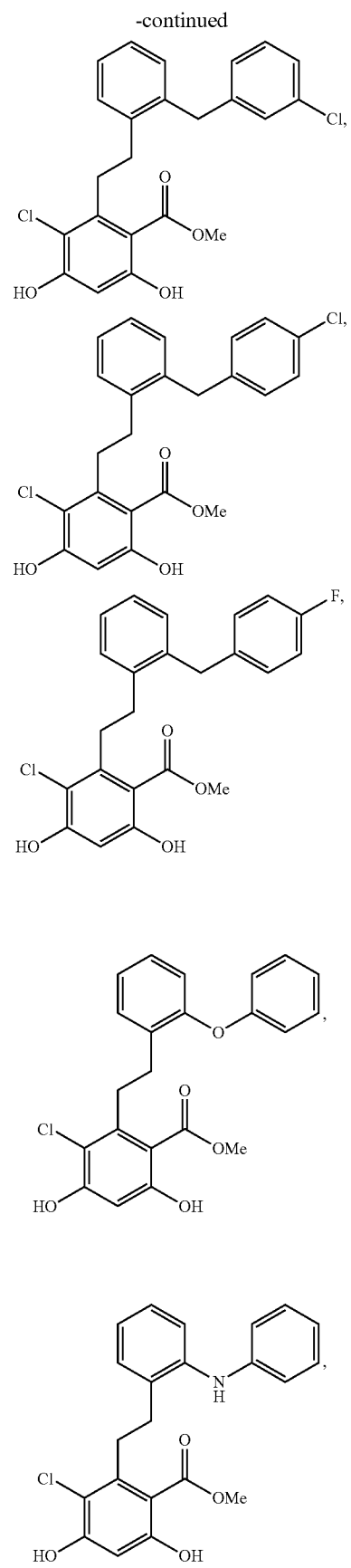

67
-continued
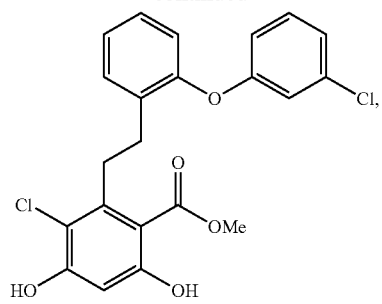
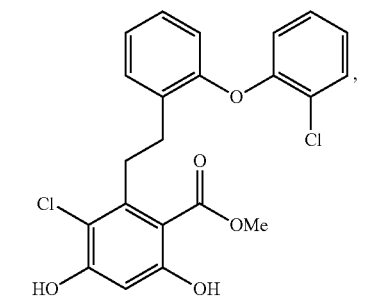
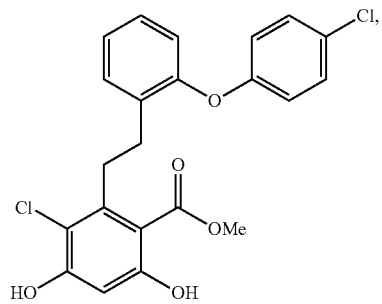
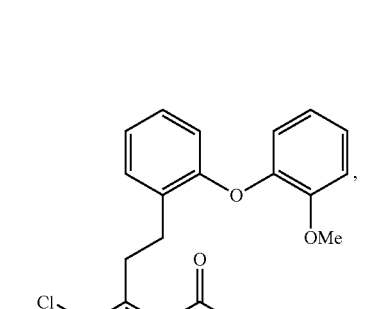
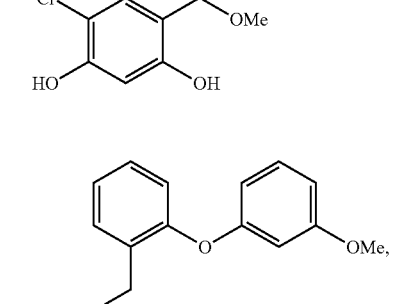
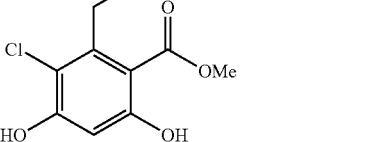
68
-continued
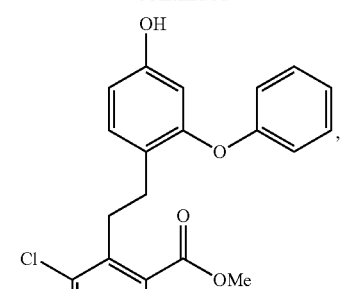
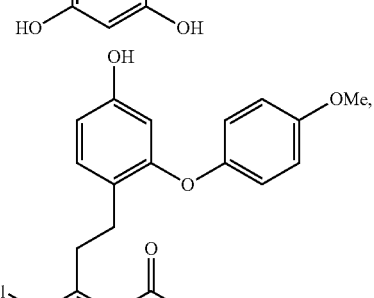
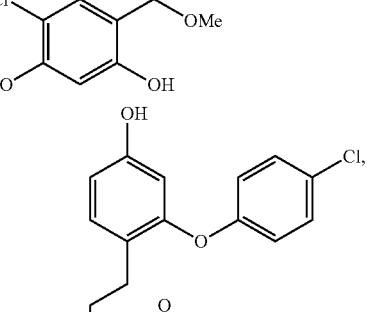
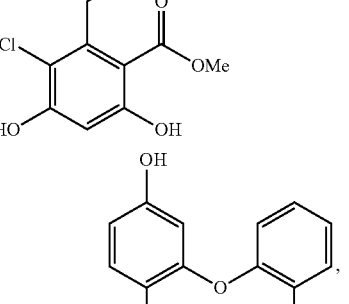
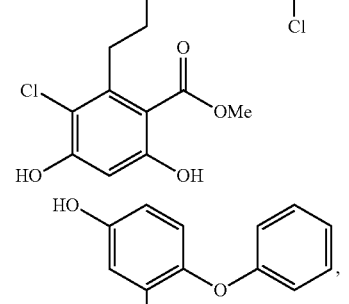
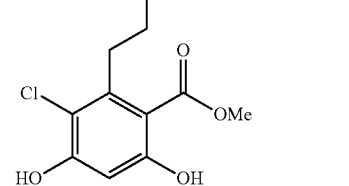

-continued

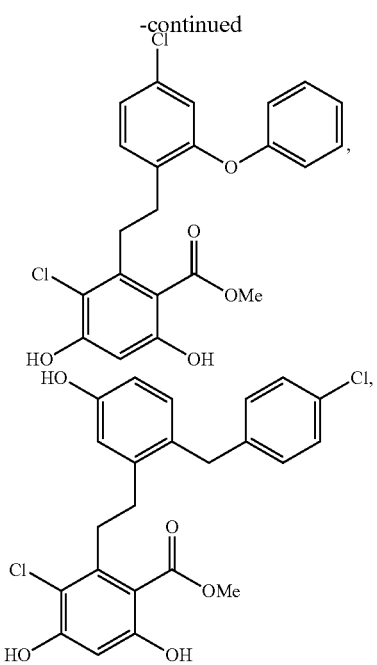

or a pharmaceutically acceptable salt thereof.

3. A compound of Formula III

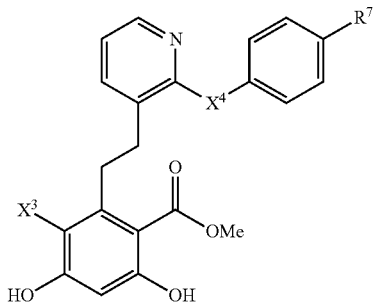

or a pharmaceutically acceptable salt thereof, wherein
$X^3$ is Cl or F;
$X^4$ is $CH_2$ or O; and
$R^7$ is alkoxy, hydroxyl, or halo.

4. A composition comprising a compound of claim 1 and a pharmaceutically acceptable carrier.

5. A pharmaceutical composition for treating metastatic cancer, the composition comprising an effective amount of the compound of claim 1 and a pharmaceutically acceptable excipient.

6. A method for inhibiting cell motility of a cancer cell, the method comprising contacting the cancer cell with a compound of claim 1.

7. A method of treating a patient or animal suffering from metastatic cancer, the method comprising administration of an effective amount of a compound of claim 1 to the patient or animal suffering from the metastatic cancer, wherein the metastatic cancer is selected from multiple myeloma, melanoma, lung cancer, hepatocellular carcinoma, breast cancer, or prostate cancer.

8. A pharmaceutical composition for treating glaucoma, the composition comprising an effective amount of the compound of claim 1 and a pharmaceutically acceptable excipient.

9. A method of inhibiting death of a cell exhibiting mutant myocilin, the method comprising contacting the cell with a compound of claim 1.

10. A method of treating a patient or animal suffering from glaucoma, the method comprising administration of an effective amount of a compound of claim 1 to the patient or animal suffering from the glaucoma.

11. A composition comprising a compound of claim 2 and a pharmaceutically acceptable carrier.

12. A pharmaceutical composition for treating metastatic cancer, the composition comprising an effective amount of the compound of claim 2 and a pharmaceutically acceptable excipient.

13. A method for inhibiting cell motility of a cancer cell, the method comprising contacting the cancer cell with a compound of claim 2.

14. A method of treating a patient or animal suffering from metastatic cancer, the method comprising administration of an effective amount of a compound of claim 2 to the patient or animal suffering from the metastatic cancer, wherein the metastatic cancer is selected from multiple myeloma, melanoma, lung cancer, hepatocellular carcinoma, breast cancer, or prostate cancer.

15. A pharmaceutical composition for treating glaucoma, the composition comprising an effective amount of the compound of claim 2 and a pharmaceutically acceptable excipient.

16. A method of inhibiting death of a cell exhibiting mutant myocilin, the method comprising contacting the cell with a compound of claim 2.

17. A method of treating a patient or animal suffering from glaucoma, the method comprising administration of an effective amount of a compound of claim 2 to the patient or animal suffering from the glaucoma.

18. A composition comprising a compound of claim 3 and a pharmaceutically acceptable carrier.

19. A pharmaceutical composition for treating metastatic cancer, the composition comprising an effective amount of the compound of claim 3 and a pharmaceutically acceptable excipient.

20. A method for inhibiting cell motility of a cancer cell, the method comprising contacting the cancer cell with a compound of claim 3.

21. A method of treating a patient or animal suffering from metastatic cancer, the method comprising administration of an effective amount of a compound of claim 3 to the patient or animal suffering from the metastatic cancer, wherein the metastatic cancer is selected from multiple myeloma, melanoma, lung cancer, hepatocellular carcinoma, breast cancer, or prostate cancer.

22. A pharmaceutical composition for treating glaucoma, the composition comprising an effective amount of the compound of claim 3 and a pharmaceutically acceptable excipient.

23. A method of inhibiting death of a cell exhibiting mutant myocilin, the method comprising contacting the cell with a compound of claim 3.

24. A method of treating a patient or animal suffering from glaucoma, the method comprising administration of an effective amount of a compound of claim 3 to the patient or animal suffering from the glaucoma.

* * * * *